United States Patent [19]
Cai et al.

[11] Patent Number: 5,620,978
[45] Date of Patent: Apr. 15, 1997

[54] 8-AZA, 6-AZA AND 6,8-DIAZA-1,4-DIHYDROQUINOXALINE-2,3-DIONES AND THE USE THEREOF AS ANTAGONISTS FOR THE GLYCINE/NMDA RECEPTOR

[75] Inventors: Sui X. Cai, Irvine, Calif.; John F. W. Keana, Eugene, Oreg.; Eckard Weber, Laguna Beach, Calif.

[73] Assignees: State of Oregon, acting by and through The Oregon State Board of Higher Education, acting for and on behalf of The Oregon Health Sciences University and The University of Oregon, Eugene Oregon, Eugene, Oreg.; The Regents of the University of California, Oakland, Calif.; ACEA Pharmaceuticals, Inc., Irvine, Calif.

[21] Appl. No.: 368,163

[22] Filed: Jan. 3, 1995

Related U.S. Application Data

[63] Continuation-in-part of Ser. No. 289,366, Aug. 11, 1994, abandoned, which is a continuation-in-part of Ser. No. 176,278, Jan. 3, 1994, abandoned.

[51] Int. Cl.$^6$ ............................ A61K 31/495; A61K 31/50
[52] U.S. Cl. ............................ 514/249; 544/350; 544/257; 514/252
[58] Field of Search ............................ 544/350; 514/249

[56] References Cited

U.S. PATENT DOCUMENTS

| | | | |
|---|---|---|---|
| 5,055,465 | 10/1991 | Davey | 514/228.2 |
| 5,283,244 | 2/1994 | Sakamoto et al. | 514/249 |
| 5,424,311 | 3/1995 | Billhardt-Troughton et al. | 514/248 |

FOREIGN PATENT DOCUMENTS

| | | |
|---|---|---|
| 0008864 | 3/1980 | European Pat. Off. . |
| 0039920 | 11/1981 | European Pat. Off. . |
| 0283162 | 9/1988 | European Pat. Off. . |
| 0290819 | 11/1988 | European Pat. Off. . |
| 0320136 | 6/1989 | European Pat. Off. . |
| 0347146 | 12/1989 | European Pat. Off. . |
| 0374534 | 6/1990 | European Pat. Off. . |
| 4-178385 | 6/1992 | Japan ........................... 544/350 |
| WO91/13878 | 9/1991 | WIPO . |
| WO92/07847 | 5/1992 | WIPO . |
| WO94/00124 | 1/1994 | WIPO . |

OTHER PUBLICATIONS

Bigge, C.F. and Boxer, P.A., "Neuronal Cell Death and Strategies for Neuroprotection," *Ann. Rep. Med. Chem.* 29:13–22 (1994).

Kaye, I.A., "Some Substituted Pyrido(2,3)pyrazines," *J. Med. Chem.* 7:240–241 (1964).

Kessler et al., "A Glycine Site Associated with N-Methyl-D-Aspartic Acid Receptors: Characterization and Identification of a New Class of Antagonists," *J. Neurochem.* 52(4):1319–1328 (1989).

Kulagowski et al., "3'-(Arylmethyl)- and 3'-(Aryloxy)-3-phenyl-4-hydroxyquinolin-2(1H)-ones: Orally Active Antagonists of the Glycine Site on the NMDA Receptor," *J. Med. Chem.* 37:1402–1405 (1994).

Leeson, P.D., "Glycine-Site N-Methyl-D-Aspartate Receptor Antagonists," in: *Drug Design for Neuroscience* Kozikowski, A.P., Ed., Raven Press, pp. 339–381 (1993).

Leeson, P.D. and Iverson, L.L., "The Glycine Site on the NMDA Receptor: Structure-Activity Relationships and Therapeutic Potential," *J. Med. Chem.* 37(24):4053–4067.

Monn, J.A. and Schoepp, D.D., "Recent Progress in Excitatory Amino Acid Research," *Annual Reports in Medicinal Chemistry* 29:53–64 (1994).

Sakamoto et al., "Preparation of diketopiperazines as glutamate receptor antagonists," *Chem. Abstracts* 117:695 Abstracts No. 251367d (1992).

Winterfeld, K. and Wildersohn, M., "2,3-Dichlor- und 2,3,7-Trichlor-5-aza-chinoxalin," *Archiv der Pharmazie* 303(1):44–48 (1970).

Albert, A., et al., "Pteridine Studies. VIII. Degradation of Pteridine. Methylation of the Hydroxypteridines and Degradation of the Products," *Chem. Abstr.* 51(2):1977b (1960).

Albert, A., et al., "Pteridine Studies. X. Pteridines With More Than One Hydroxy or Amino Group," *Chem. Abstr.* 51(2):6654c (1960).

Albert, A., et al., "Pteridine Studies. Part XXXV. The Structure of the Hydrated Dimer Formed by the Action of Dilute Acid on 4-Methylpteridine," *J. Chem. Soc.* (C):1181–1187 (1968).

(List continued on next page.)

*Primary Examiner*—Mukund J. Shah
*Assistant Examiner*—Matthew V. Grumbling
*Attorney, Agent, or Firm*—Sterne, Kessler, Goldstein & Fox P.L.L.C.

[57] ABSTRACT

Disclosed is a method of treating or preventing neuronal loss associated with stroke, ischemia, CNS trauma or hypoglycemia. The method comprises administering to an animal a compound of the formula:

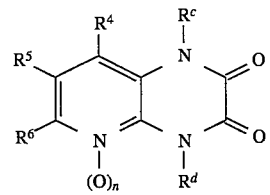

or a pharmaceutically acceptable salt thereof; wherein n is zero or 1; $R^4$, $R^5$, $R^6$ are independently hydrogen, nitro, amino, halo, haloalkyl, cyano, alkyl, cycloalkyl, alkenyl, alkynyl, azido, acylamino, alkylsulfonyl, aryl, substituted aryl, heteroaryl, alkoxy, trialkylsilyl-substituted alkoxy, aryloxy, substituted aryloxy, heteroaryloxy, a heterocyclic group, a heterocyclicoxy group, aralkoxy, or haloalkoxy; and $R^c$ and $R^d$ are defined in the specification. These compounds have high binding to the glycine site of the NMDA receptor.

10 Claims, 5 Drawing Sheets

OTHER PUBLICATIONS

Boutte, D., et al., "Étude des Mono et Dihydroxy–pyrido–[2.3–b] et [3.4–b] Pyrazines et Synthèse de la Dioxo–1.4 Tétrahydro–1.2.3.4 Pyrido–[2'.3':5.6] Pyrazino–[2.3–d] Pyridazine," *C.R. Acad. Sc. Paris, Ser. C.* 273(23:1645–1648 (1971).

Clark, J., et al., "Heterocyclic Studies. Part VIII. 2–Phenylpteridine and Some Related Compounds," *J. Chem. Soc.* (C):1408–1412 (1969).

Clark, J., and Murdoch, P.N.T., "Heterocyclic Studies. Part X. 4–Phenylpteridine and Some Methyl Derivatives," *J. Chem. Soc.* (C):1883–1886 (1968).

Gottlieb, R., and Pfleiderer, W., "Synthese und Elektrochemisches Verhalten von 6,7–Dioxotetrahydropteridinen und 2,3–Dioxotetrahydropyrido–pyrazinen," *Chem. Ber.* 111(5):1763–1779 (1978).

McFarlane, M.D., and Smith, D.M., "A New Route to N–Hydroxyquinoxaline–2,3–Diones and Some Aza–Analogues," *Tetrahedron Lett.* 28(50):6363–6366 (1987).

Pfleiderer, W., and Lohrmann, R., "Pteridines. XV. Synthesis of 2–Amino–4–alkoxy–7–oxodihydropteridines," *Chem. Abstr.* 56(5):4752b (1962).

Weinstock, J., and Dunoff, R.Y., "Pteridines. IX. Some Pteridine Isomers of Triamterene," *J. Med. Chem.* 11(3):565–568 (1968).

Boast, C. A. et al., "The N–methyl–D–aspartate antagonists CGS 19755 and CPP reduce ischemic brain damage in gerbils," *Brain Res.* 442:345–348 (1988).

Brady, K. T. et al., "Stereoisomers of N–Allylnormetazocine: Phencyclidine–Like Behavioral Effects in Squirrel Monkeys and Rats," *Science* 215:178–180 (1982).

Burton, D. E. et al., "Halogeno–O–phenylenediamines and Derived Heterocycles. Part I. Reductive Fission of Benzotriazoles to O–Phenylenediamines," *J. Chem. Soc.* (C):1268–1280 (1968).

Choi, D. W. et al., "Glutamate Neurotoxicity in Cortical Cell Culture," *J. Neurosci.* 7(2):357–368 (1987).

Church, J. et al., "Ketamine and MK–801 as Neuroprotective Agents in Cerebral Ischemia/Hypoxia," in: *Sigma and Phenycylidine–Like Compounds as Molecular Probes in Biology*, Domino, E. F. et al., eds., NPP Books: Ann Arbor pp. 747–756 (1988).

Colllins, R. C., "Selective Vulnerability of Brain: New Insights from the Excitatory Synapse," *Metabolic Brain Dis.* 1(4):231–240 (1986).

Collins, R. C. et al., "Selective Vulnerability of the Brain: New Insights into the Pathophysiology of Stroke," *Ann. Internal Med.* 110:992–1000 (1989).

Daines, R. A. et al., "Trisubstituted Pyridine Leukotriene $B_4$ Receptor Antagonists: Synthesis and Structure–Activity Relationships," *J. Med. Chem.* 36(22):3321–3332 (Nov. 1993).

Decker, T. and M.–L. Lohmann–Matthes, "A quick and simple method for the quantitation of lactate dehydrogenase release in measurements of cellular cytotoxicity and tumor necrosis factor (TNF) activity," *J. Immunol. Meth.* 15:61–69 (1988).

Dickenson, A. H. and E. Aydar, "Antagonism at the glycine site on the NMDA receptor reduces spinal nociception in the rat," *Neurosci. Lett.* 121:263–266 (1991).

Dubuisson, D. and S. G. Dennis, "The Formalin Test: A Quantitative Study of the Analgesic Effects of Morphine, Meperidine, and Brain Stem Stimulation in Rats and Cats," *Pain* 4:161–174 (1977).

Fletcher, E. J. et al., "Involvement of Glycine in Excitatory Neurotransmission," in: *Glycine Neurotransmission*, Ottersen, O. P. et al., eds., John Wiley and Sons, Ltd: Somerset, New Jersey (1990).

Fletcher, E. J. and D. Lodge, "Glycine reverses antagonism of N–methyl–D–aspartate (NMDA) by 1–hydroxy–3–aminopyrrolidone–2 (HA–966) but not by D–2–amino–5–phophonovalerate (D–AP5) on rat cortical slices," *Eur. J. Pharm.* 151:161–162 (1988).

Gill, R. et al., "Systemic Administration of MK–801 Protects Against Ischemia–Induced Hippocampal Neurodegeneration in the Gerbil," *J. Neurosci.* 7(10):3343–3349 (1987).

Globus, M. Y.–T. et al., "Comparative Effects of Transient Global Ischemia on Extracellular Levels of Glutamate, Glycine, and γ–Aminobutyric Acid in Vulnerable and Nonvulnerable Brain Regions in the Rat," *J. Neurochem.* 57(2):470–478 (1991).

Gray, N. M. et al., "Novel Indole–2–carboxylates as Ligands for the Strychnine–Insensitive N–Methyl–D–aspartate–Linked Glycine Receptor," *J. Med. Chem.* 34:1283–1292 (1991).

Haley, J. E. et al., et al., "Evidence for spinal N–Methyl–D–aspartate receptor involvement in prolonged chemical nociception in the rat," *Brain Res.* 518:218–226 (1990).

Huettner, J. E. and B. P. Bean, "Block of N–methyl–D–aspartate–activated current by the anticonvulsant MK–801: Selective binding to open channels," *Proc. Natl. Acad. Sci.* 85:1307–1311 (1988).

Huidobro, F. et al., "Studies on Tolerance Development to Single Doses of Morphine in Mice," *J. Pharmacol. Exp. Ther.* 198(2):318–329 (1976).

Hunger, A. et al., "1–Aninoalkyl–7–azabenzimidazoles," *Chem. Abs.* 63:14876 (1965).

Israel, M. and A. R. Day, "Preparation of Pyrido–(2,3)–pyrazines, Pyrido–(3,4)–pyrazines and Imidazo–(b)–pyridines," *J. Org. Chem.* 24:1455–1460 (1959).

Johnson, J. W. and P. Ascher, "Glycine potentiates the NMDA response in cultured mouse brain neurons," *Nature* 325:529–531 (1987).

Jones, B. J. et al., "The potential anxiolytic activity of GR38032F, a 5–$HT_3$–receptor antagonist," *Br. J. Pharmacol.* 93:985–993 (1988).

Keana, J. F. W. et al., "Synthesis and cheracterization of a series of diarylguanidines that are noncompetitive N–methyl–D–aspartate receptor antagonists with neuroprotective properties," *Proc. Natl. Acad. Sci. USA* 86:5631–5635 (1989).

Kemp, J. A. et al., "7–Chlorokynurenic acid is a selective antagonist at the glycine modulatory site of the N–methyl–D–aspartate receptor complex," *Proc. Natl. Acad. Sci. USA* 85:6547–6550 (1988).

Koek, W. et al., "MK–801, a Proposed Noncompetitive Antagonist of Excitatory Amino Acid Neurotransmission, Produces Phencyclidine–Like Behavioral Effects in Pigeons, Rats and Rhesus Monkeys," *J. Pharmacol. Exp. Ther.* 245(3):969–974 (1988).

Kornetsky, c. and G. Bain, "Morphine: Single–Dose Tolerance," *Science* 162:1011–1012 (1968).

Kress, T. J. et al., "Selective Chlorinations in Sulfuric Acid. Synthesis of Some 2–Amino–5–chloro–, 2–Amino–3–chloro–, and 2–Amino–3,5–dichloropyridines," *J. Org. Chem.* 41(1):93–96 (1976).

Landon, R. M. and R. J. Robbins, "Somatostatin Release from Dissociated Cerebral Cortical Cell Cultures," *Meth. Enzymol.* 124:412–424 (1986).

Leo, A. et al., "Partition Coefficients and Their Uses," *Chem. Rev.* 71(6):525–615 (1971).

Lonsdale, E., "Effect of Thiamine Tetrahydrofurfuryl Disulfide on Audiogeneic Seizures in DBA/2J Mice," *Dev. Pharmacol. Ther.* 4:28–36 (1982).

Lutfy, K. et al., "Blockade of morphine–induced analgesia and tolerance in mice by MK–801," *Brain Res.* 616:83–88 (Jun. 1993).

Lutfy, K. and B. C. Yoburn, "The Role of Opioid Receptor Density in Morphine Tolerance," *J. Pharmacol. Exp. Ther.* 256(2):575–580 (1991).

MacDonald, J. F. et al., "Use–Dependent Block of Excitatory Amino Acid Currents in Cultured Neurons by Ketamine," *J. Neurophysiol.* 58(2):251–266 (1987).

Marek, P. et al., "Excitatory amino acid antagonists (kynurenic acid and MK–801) attenuate the development of morphine tolerance in the rat," *Brain Res.* 547:77–81 (1991).

McNamaara, D. et al., "5,7–Dichlorokynurenic acid, a potent and selective competitive antagonist of the glycine site on NMDA receptors," *Neurosci. Lett.* 120:17–20 (1990).

Miller, B. et al., "Potentiation of NMDA receptor currents by arachidonic acid," *Nature* 355:722–725 (1992).

Reynolds, I. J. and R. J. Miller, "Allosteric Modulation of N–Methyl–D–Aspartate Receptors," *Adv. Pharmacol.* 21:101–126 (1990).

Schoepp, D. D. et al., "Neuroprotectant effects of LY 274614, a structural novel systematically active competitive NMDA receptor antagonist," *J. Neural Transm.* 85:131–143 (1991).

Sircar, R. and S. R. Zukin, "Kinetic mechanisms of glycine requirement for N–methyl–D–aspartate channel activation," *Brain Res.* 556:280–284 (1991).

Skilling, S. R. et al., "Differential Effects of C– and N–Terminal Substance P Metabolites on the Release of Amino Acid Neurotransmitters from the Spinal Cord: Potential Role in Nociception," *J. Neurosci.* 10(4):1309–1318 (1990).

Steinberg, G. K. et al., "Delayed treatment with dextromethorphan and dextrorphan reduces cerebral damage after transient focal ischemia," *Neurosci. Lett.* 89:193–197 (1988).

Swinyard, E. A., "Assay of Antiepileptic Drug Activity in Experimental Animals: Standard Tests," in: *Anticonvulsant Drugs*, Mercier, J. ed., Pergamon Press: Oxford pp. 47–65 (1973).

Tamura, Y. et al., "O–Mesitylenesulfonylhydroxylamine and Related Compounds—Powerful Animating Reagents," *Synthesis* 1:1–17 (1977).

Tiseo, P. J. and C. E. Inturrisi, "Attenuation and Reversal of Morphine Tolerance by the Competitive N–Methyl–D–Aspartate Receptor Antagonist, LY274612," *J. Pharmacol. Exp. Ther.* 264:1090–1096 (Mar. 1993).

Tomasik, P. and Z. Skrowaczewska, "Reduction of 3,5–dinitropyridine and its 2–substituted derivatives by first–order sustituents. III. Reduction of 2–amino and 2–hydrazino–3, 5–dinitropyridines," *Chem. Abs.* 65:3826 (1966).

Tricklebank, M. D. et al., "A role for receptors of N–methyl–D–aspartic acid in the discriminative stimulus properties of phencyclidine," *Eur. J. Pharmacol.* 141:497–501 (1987).

Tricklebank, M. D. et al., "The behavioural effects of MK–801: a comparison with antagonists acting non–competitively and competitively at the NMDA receptor," *Eur. J. Pharmacol.* 167:127135 (1989).

Trujillo, K. A. and H. Akil, "Inhibition of Morphine Tolerance and Dependence by the NMDA Receptor Antagonist MK–801," *Science* 451:85–87 (1991).

Watkins, J. C. and H. J. Olverman, "Agonists and antagonists for excitatory amino acid receptors," *Trends Neurol. Sci.* 10(7):265–272 (1987).

Way, E. L. et al., "Simultaneous Quantitative Assessment of Morphine Tolerance and Physical Dependence," *J. Pharmacol. Exp. Ther.* 167(1):1–8 (1969).

Willetts, J. and R. L. Balster, "The Discriminative Stimulus Effects of N–Methyl–D–Aspartate Antagonists in Phencyclidine–Trained Rats," *Neuropharmacol.* 27(12):1249–1256 (1988).

Wong, E. H. F. and J. A. Kemp, "Sites for Antagonism on the N–Methyl–D–Aspartate Receptor Channel Complex," *Annu. Rev. Pharmacol. Toxicol.* 31:401–425 (1991).

Wong, E. H. F. et al., "The anticonvulsant MK–801 is a potent N–Methy–D–aspartate antagonist," *Proc. Natl. Acad. Sci. USA* 83:714–7108 (1986).

Zukin, S. R. et al., "Behavioural and biochemical stereoselectivity of sigma opiate/PCP receptors," *Brain Res.* 294:174–177 (1984).

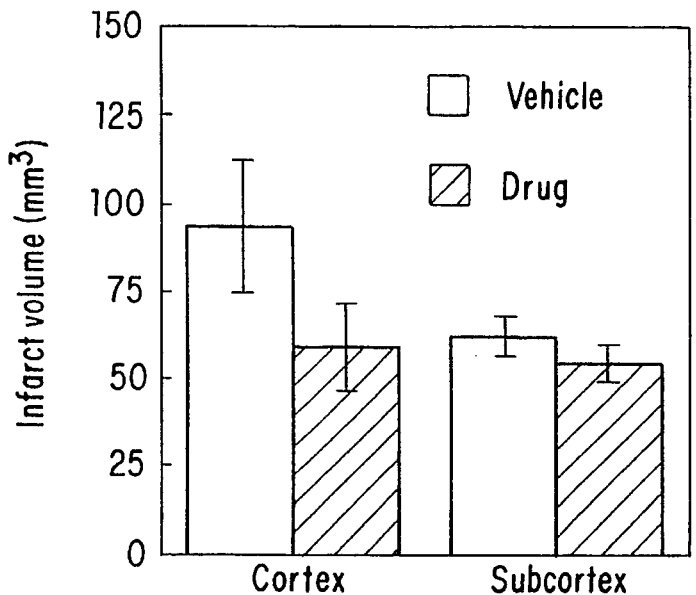
FIG. 5A
FIG. 5B
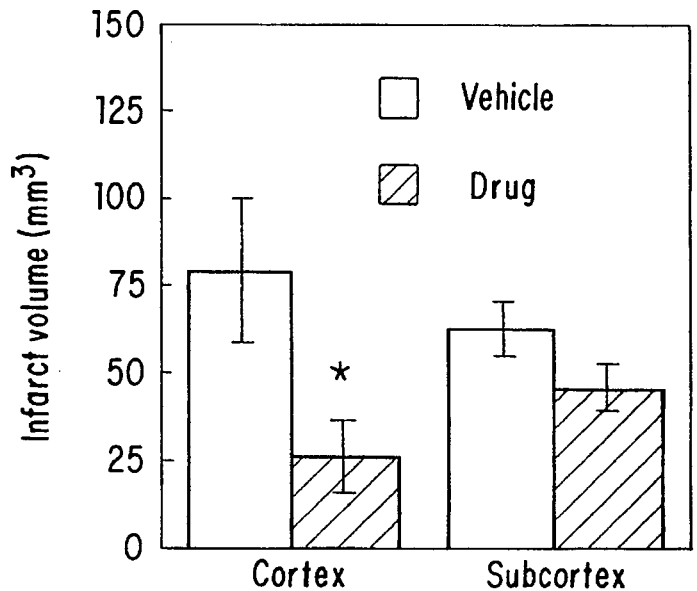
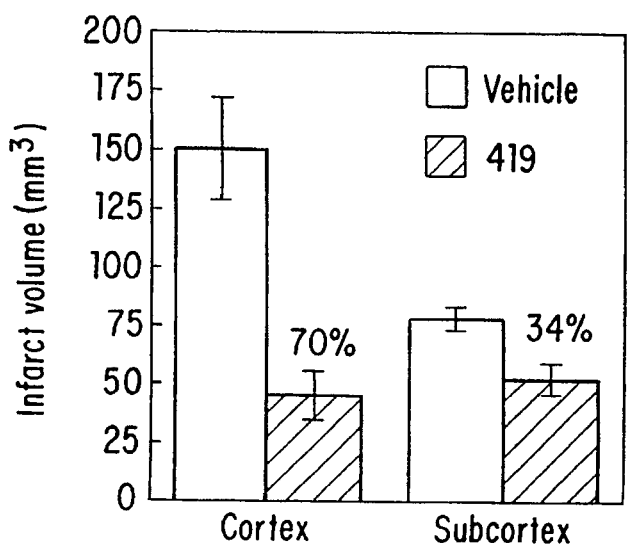
FIG. 6

8-AZA, 6-AZA AND 6,8-DIAZA-1,4-DIHYDROQUINOXALINE-2,3-DIONES AND THE USE THEREOF AS ANTAGONISTS FOR THE GLYCINE/NMDA RECEPTOR

The present invention was made with government support under grant DA 06726 awarded by the National Institute of Drug Abuse. Therefore, the U.S. Government has certain rights in the invention.

CROSS-REFERENCE TO RELATED APPLICATION

This is a continuation-in-part of U.S. application Ser. No. 08/289,366, filed Aug. 11, 1994, which is a continuation-in-part of U.S. application Ser. No. 08/176,278, filed Jan. 3, 1994, the contents of each of which are fully incorporated by reference, both now abandoned.

FIELD OF THE INVENTION

The present invention is in the field of medicinal chemistry. In particular, the present invention relates to substituted and unsubstituted 8-aza, 6-aza, and 6,8-diaza-1,4-dihydroquinoxaline-2,3-diones as well as N-oxides thereof and pharmaceutically acceptable salts thereof and their use to treat or prevent neuronal degeneration associated with ischemia, pathophysiologic conditions associated with neuronal degeneration, convulsions, anxiety, and chronic pain, as well as to induce anesthesia, treat or prevent psychosis and for preventing opiate tolerance.

BACKGROUND OF THE INVENTION

Glutamate is thought to be the major excitatory neurotransmitter in the brain. There are three major subtypes of glutamate receptors in the CNS. These are commonly referred to as kainate, AMPA, and N-methyl-D-aspartate (NMDA) receptors (Watkins and Olverman, Trends in Neurosci. 7:265–272 (1987)). NMDA receptors are found in the membranes of virtually every neuron in the brain. NMDA receptors are ligand-gated cation channels that allow $Na^+$, $K^+$, and $Ca^{++}$ to permeate when they are activated by glutamate or aspartate (non-selective, endogenous agonists) or by NMDA (a selective, synthetic agonist) (Wong & Kemp, Ann. Rev. Pharmacol. Toxicol. 31:401–425 (1991)).

Glutamate alone cannot activate the NMDA receptor. In order to become activated by glutamate, the NMDA receptor channel must first bind glycine at a specific, high affinity, glycine binding site that is separate from the glutamate/NMDA binding site on the receptor protein (Johnson & Ascher, Nature 325:329–331 (1987)). Glycine is therefore an obligatory co-agonist at the NMDA receptor/channel complex (Kemp, J. A., et al., Proc. Natl. Acad. Sci. USA 85:6547–6550 (1988)).

In addition to the binding sites for glutamate/NMDA and glycine, the NMDA receptor carries a number of other functionally important binding sites. These include binding sites for $Mg^{++}$, $Zn^{++}$, polyamines, arachidonic acid and phencyclidine (PCP) (Reynolds & Miller, Adv. in Pharmacol. 21:101–126 (1990); Miller, B., et al., Nature 355:722–725 (1992)). The PCP binding site—now commonly referred to as the PCP receptor—is located inside the pore of the ionophore of the NMDA receptor/channel complex (Wong, E. H. F., et al., Proc. Natl. Acad. Sci. USA 83:7104–7108 (1986); Huettner and Bean, Proc. Natl. Acad. Sci. USA 85:1307–1311 (1988); MacDonald, J. F., et al., Neurophysiol. 58:251–266 (1987)). In order for PCP to gain access to the PCP receptor, the channel must first be opened by glutamate and glycine. In the absence of glutamate and glycine, PCP cannot bind to the PCP receptor although some studies have suggested that a small amount of PCP binding can occur even in the absence of glutamate and glycine (Sircar & Zukin, Brain Res. 556:280–284 (1991)). Once PCP binds to the PCP receptor, it blocks ion flux through the open channel. Therefore, PCP is an open channel blocker and a non-competitive glutamate antagonist at the NMDA receptor/channel complex.

One of the most potent and selective drugs that bind to the PCP receptor is the anticonvulsant drug MK-801. This drug has a $K_d$ of approximately 3 nM at the PCP receptor (Wong, E. H. F., et al., Proc. Natl. Acad. Sci. USA 83:7104–7108 (1986)).

Both PCP and MK-801 as well as other PCP receptor ligands, e.g., dextromethorphan, ketamine and N,N,N'-trisubstituted guanidines, have neuroprotective efficacy both in vitro and in vivo (Gill, R., et al., J. Neurosci. 7:3343–3349 (1987); Keana, J. F. W., et al., Proc. Natl. Acad. Sci. USA 86:5631–5635 (1989); Steinberg, G. K., et al., Neuroscience Lett. 89:193–197 1988); Church, J., et al., in Sigma and Phencyclidine-Like Compounds as Molecular Probes in Biology, Domino & Kamenka, eds., NPP Books, Ann Arbor (1988), pp. 747–756). The well-characterized neuroprotective efficacy of these drugs is largely due to their capacity to block excessive $Ca^{++}$ influx into neurons through NMDA receptor channels, which become over activated by excessive glutamate release in conditions of brain ischemia (e.g., in stroke, cardiac arrest ischemia etc.) (Collins, R. C., Metabol. Br. Dis. 1:231–240 (1986); Collins, R. C., et al., Annals Int. Med. 110:992–1000 (1989)).

However, the therapeutic potential of these PCP receptor drugs as ischemia rescue agents in stroke has been severely hampered by the fact that these drugs have strong PCP-like behavioral side effects (psychotomimetic behavioral effects) which appear to be due to the interaction of these drugs with the PCP receptor (Tricklebank, M. D., et al., Eur. J. Pharmacol. 167:127–135 (1989); Koek, W., et al., J. Pharmacol. Exp. Ther. 245:969 (1989); Willets & Balster, Neuropharmacology 27:1249 (1988)). These PCP-like behavioral side effects appear to have caused the withdrawal of MK801 from clinical development as an ischemia rescue agent. Furthermore, these PCP receptor ligands appear to have considerable abuse potential as demonstrated by the abuse liability of PCP itself.

The PCP-like behavioral effects of the PCP receptor ligands can be demonstrated in animal models: PCP and related PCP receptor ligands cause a behavioral excitation (hyperlocomotion) in rodents (Tricklebank, M. D., et al., Eur. J. Pharmacol. 167:127–135 (1989)) and a characteristic katalepsy in pigeons (Koek, W., et al., J. Pharmacol. Exp. Ther. 245:969 (1989); Willets & Balster, Neuropharmacology 27:1249 ( 1988)); in drug discrimination paradigms, there is a strong correlation between the PCP receptor affinity of these drugs and their potency to induce a PCP-appropriate response behavior (Zukin, S. R., et al., Brain Res. 294:174 (1984); Brady, K. T., et al., Science 215:178 (1982); Tricklebank, M. D., et al., Eur. J. Pharmacol. 141:497 (1987)).

Drugs acting as competitive antagonists at the glutamate binding site of the NMDA receptor, such as, CGS 19755 and LY274614, also have neuroprotective efficacy because these drugs-like the PCP receptor ligands—can prevent excessive $Ca^{++}$ flux through NMDA receptor/channels in ischemia (Boast, C. A., et al., Brain Res. 442:345–348 (1988); Schoepp, D. D., et al., J. Neural. Trans. 85:131–143 (1991)). However, competitive NMDA receptor antagonists also have PCP-like behavioral side-effects in animal models (behavioral excitation, activity in PCP drug discrimination tests) although not as potently as MK-801 and PCP (Tricklebank, M. D., et al., Eur. J. Pharmacol. 167:127–135 (1989)).

An alternate way of inhibiting NMDA receptor channel activation is by using antagonists at the glycine binding site of the NMDA receptor. Since glycine must bind to the glycine site in order for glutamate to effect channel opening (Johnson & Ascher, Nature 325:329–331 (1987); Kemp, J. A., et al., Proc. Natl. Acad. Sci. USA 85:6547–6550 (1988)), a glycine antagonist can completely prevent ion flux through the NMDA receptor channel-even in the presence of a large amount of glutamate.

Recent in vivo microdialysis studies have demonstrated that in the rat focal ischemia model there is a large increase in glutamate release in the ischemic brain region with no significant increase in glycine release (Globus, M. Y. T., et al., J. Neurochem. 57:470–478 (1991)). Thus, theoretically, glycine antagonists should be very powerful neuroprotective agents because they can prevent the opening of NMDA channels by glutamate non-competitively and, therefore, unlike competitive NMDA antagonists, do not have to overcome the large concentrations of endogenous glutamate that are released in the ischemic brain region.

Furthermore, because glycine antagonists act at neither the glutamate/NMDA nor the PCP binding sites to prevent NMDA channel opening, these drugs might not cause the PCP-like behavioral side effect seen with both PCP receptor ligands and competitive NMDA receptor antagonists (Tricklebank, M. D., et al., Eur. J. Pharmacol. 167:127–135 (1989); Koek, W., et al., J. Pharmacol. Exp. Ther. 245:969 (1989); Willets & Balster, Neuropharmacology 27:1249 (1988); Zukin, S. R., et al., Brain Res. 294:174 (1984); Brady, K. T., et al., Science 215:178 (1982); Tricklebank, M. D., et al., Eur. J. Pharmacol. 141:497 (1987)). That glycine antagonists may indeed be devoid of PCP-like behavioral side effects has been suggested by recent studies in which available glycine antagonists were injected directly into the brains of rodents without resulting in PCP-like behaviors (Tricklebank, M. D., et al., Eur. J. Pharmacol. 167:127–135 (1989)).

For recent reviews on glycine antagonists, reference is made to Leeson, P. D., "Glycine-Site N-Methyl-D-Aspartate Receptor Antagonists," chapter 13 in Drug Design for Neuroscience, Kozikowski, A. P., ed., Raven Press, New York (1993), pp. 338–381 and Leeson & Iversen, J. Med. Chem. 37:4053–4067 (1994).

However, there have been two major problems which have prevented the development of glycine antagonists as clinically useful neuroprotective agents:

A. Most available glycine antagonists with relatively high receptor binding affinity in vitro such as 7-Cl-kynurenic acid (Kemp, J. A., et al., Proc. Natl. Acad. Sci. USA 85:6547-6550 (1988)), 5,7-dichlorokynurenic acid (McNamara, D., et al., Neurosci. Lett. 120:17–20 (1990)) and indole-2-carboxylic acid (Gray, N. M., et al., J. Med. Chem. 34:1283–1292 (1991)) cannot penetrate the blood/brain barrier and, therefore, have no utility as therapeutic agents;

B. The only widely available glycine antagonist that sufficiently penetrates the blood/brain barrier-the drug HA-966 (Fletcher & Lodge, Eur. J. Pharmacol. 151:161–162 (1988))—is a partial agonist with micromolar affinity for the glycine binding site. A neuroprotective efficacy for HA-966 in vivo has not been demonstrated, nor has it been demonstrated for the other available glycine antagonists because they lack bioavailability in vivo.

However, one recent success in identifying orally active glycine receptor antagonists was reported by Kulagowski et al., J. Med. Chem. 37:1402–1405 (1994), who disclose that 3-substituted 4-hydroxyquinoline-2(1H)-ones are selective glycine antagonists possessing potent in vivo activity.

A need continues to exist for potent and selective glycine/NMDA antagonists which can penetrate the blood/brain barrier and which:

lack the PCP-like behavioral side effects common to the PCP-like NMDA channel blockers, such as MK801, or to the competitive NMDA receptor antagonists, such as CGS19755;

show potent anti-ischemic efficacy because of the non-competitive nature of their glutamate antagonism at the NMDA receptor;

have utility as novel anticonvulsants with fewer side-effects than the PCP-like NMDA channel blockers or the competitive NMDA antagonists;

help in defining the functional significance of the glycine binding site of the NMDA receptor in vivo.

There have been a number of reports in the literature regarding the preparation of 8-aza and 7-aza-1,4-dihydroquinoxaline-2,3-diones. For example, Sakamoto, S. et al., Chem. Abstr. 117:251367d (1992), discloses that "diketopiperazines" having the following formula are glutamate receptor antagonists:

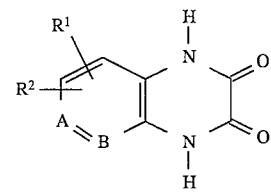

wherein either A or B=N and the other =CH, $R^1$=$NO_2$, mono- or di-lower alkylamino, morpholino, OH, lower alkoxy, alkylthio, alkylsulfonyl or alkyl; $R^2$=H, $NO_2$, mono- or di-lower alkylamino, morpholino, OH, lower alkoxy, alkylthio, alkylsufonyl, or alkyl.

Kate, I., J. Med Chem. 7:240 (1964) discloses diketopyridopyrazine derivatives having amino or chlorine substituents.

Winterfeld, K., Arch. Pharm. 303:44 (1970) discloses diketopyridopyrazine derivatives having amino or chlorine substituents.

Sakamoto, S., et al, WO 92/07847, disclose "fused pyrazine" derivatives that inhibit the glutamate receptor having the formula:

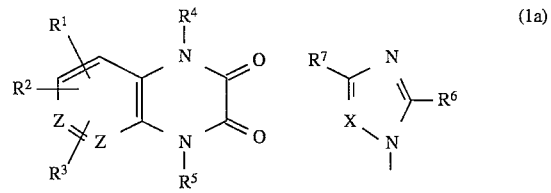

(1a)

wherein Z represents C or N, provided that two Zs are not N atoms at the same time, $R^1$ represents (1a) wherein X represents N or $R^8$C, $R^6$ represents H or alkyl, and $R^7$ and $R^8$ each represent H, alkyl, nitro or phenyl, or alternatively $R^7$ and $R^8$ are combined together to represent butadienylene or 1,4-butylene; $R^2$ and $R^3$ each represent H, F, cyano, acyl, nitro, alkyl, morpholino, or $R^1$; $R^4$ and $R^5$ each represent H, hydroxy, alkyl, cycloalkyl, heterocycle, phenyl, or Y-substituted alkyl; Y represents hydroxy, acyloxy, F-substituted methyl, cycloalkyl, tetrahydrofuryl, carboxy, alkoxycarbonyl, or $NR^9R^{10}$; and $R^9$ and $R^{10}$ represent H or alkyl, or, alternatively, $R^9$ and $R^{10}$ are combined together to represent a 5- or 6-membered cyclic group, which may contain oxygen atom(s). See also, U.S. Pat. No. 5,283,244, issued Feb. 1, 1994.

Kessler, M., et al., J. Neurochem. 52:1319–1328 (1989), disclose that pyrido (2,3-b)pyrazine-2,3-diol (8-aza-1,4-dihydroquinoxaline-2,3-dione) is an active inhibitor of $^3[H]$ glycine binding at the strychnine-insensitive glycine sites associated with NMDA receptors.

International Application Publication No. $WO_{91/13878}$ discloses the following N-substituted 1,4-dihydroquinoxaline-2,3-diones, which bind to the glycine receptor:

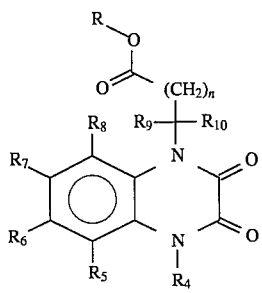

wherein R represents hydrogen, $C_{1-6}$ alkyl, or aralkyl, and n is an integer from to 5; $R^4$ represents hydrogen or hydroxy; $R^5$, $R^6$, $R^7$, and $R^8$ independently represent hydrogen, nitro, halogen, alkoxy, aryloxy, aralkoxy, $C_{1-6}$-alkyl or aryl; $R^9$ represents hydrogen, lower alkyl, or aryl; $R^{10}$ represents hydrogen, or alkyl, and pharmaceutically acceptable salts thereof.

SUMMARY OF THE INVENTION

The invention relates to a method of treating or preventing neuronal loss associated with stroke, ischemia, CNS trauma, hypoglycemia, and surgery, as well as treating neurodegenerative diseases including Alzheimer's disease, amyotrophic lateral sclerosis, Huntington's disease, and Down's syndrome, treating or preventing the adverse consequences of the overstimulation of the excitatory amino acids, as well as treating anxiety, convulsions, chronic pain, psychosis, inducing anesthesia, and preventing opiate tolerance, comprising administering to an animal in need of such treatment a compound of the Formulae (I–III)

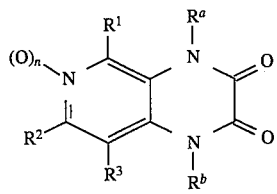

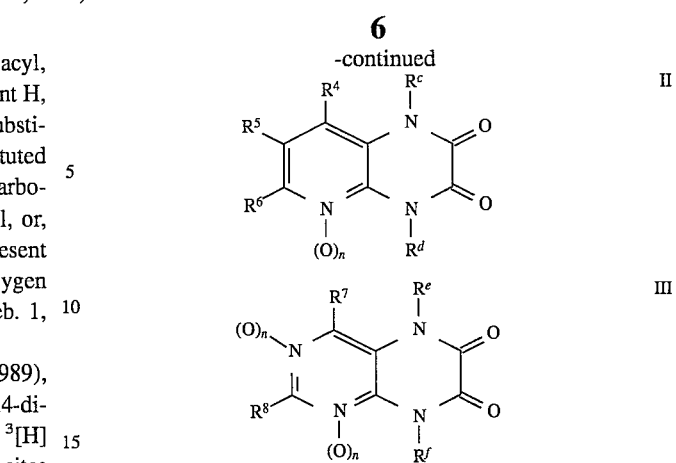

or a tautomer thereof or a pharmaceutically acceptable salt thereof;

wherein $R^1$–$R^8$ may be hydrogen, nitro, amino, halo, haloalkyl, cyano, alkyl, cycloalkyl, alkenyl, alkynyl, azido, acylamino, alkylsulfonyl, aryl, substituted aryl, heteroaryl, alkoxy, trialkylsilyl-substituted alkoxy, aryloxy, substituted aryloxy, heteroaryloxy, a heterocyclic group, a heterocyclicoxy group, aralkoxy or haloalkoxy;

n is 0 or 1; and $R^a$, $R^b$, $R^c$, $R^d$, $R^e$, and $R^f$ is hydrogen, hydroxy, amino, —$CH_2CONHAr$, —NHCONHAr, —NHCOCH$_2$Ar, or —COCH$_2$Ar, wherein Ar is an aryl group;

or a radical having the Formula:

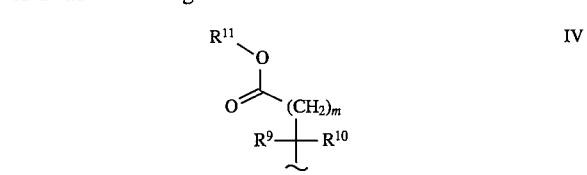

wherein $R^9$ is hydrogen, lower alkyl of 1–6 carbon atoms, or aryl;

$R^{10}$ is hydrogen or lower alkyl of 1–6 carbon atoms;

m is an integer from 0 to 5; and $R^{11}$ is hydrogen, alkyl of 1–6 carbon atoms, or aralkyl.

BRIEF DESCRIPTION OF THE FIGURES

FIG. 5 (panels A and B) depicts the effect of 6-chloro-8-(N-oxy)aza-1,4-dihydroquinoxaline-2,3-dione on cortical and subcortical infarct volume. Drug was administered immediately after MCA occlusion (10 mg/kg bolus+7 mg/kg/h for 22 h, Panel A, and 20 mg/kg bolus+14 mg/kg/h for 22 h, Panel B).

FIG. 6 depicts the effect of 6-chloro-8-(N-oxy)aza-1,4-dihydroquinoxaline-2,3-dione on conical and subcortical infarct volume. Drug was administered 30 min after MCA occlusion (20 mg/kg bolus+14 mg/kg/h for 22 h).

DESCRIPTION OF THE PREFERRED EMBODIMENTS

Figure 1:
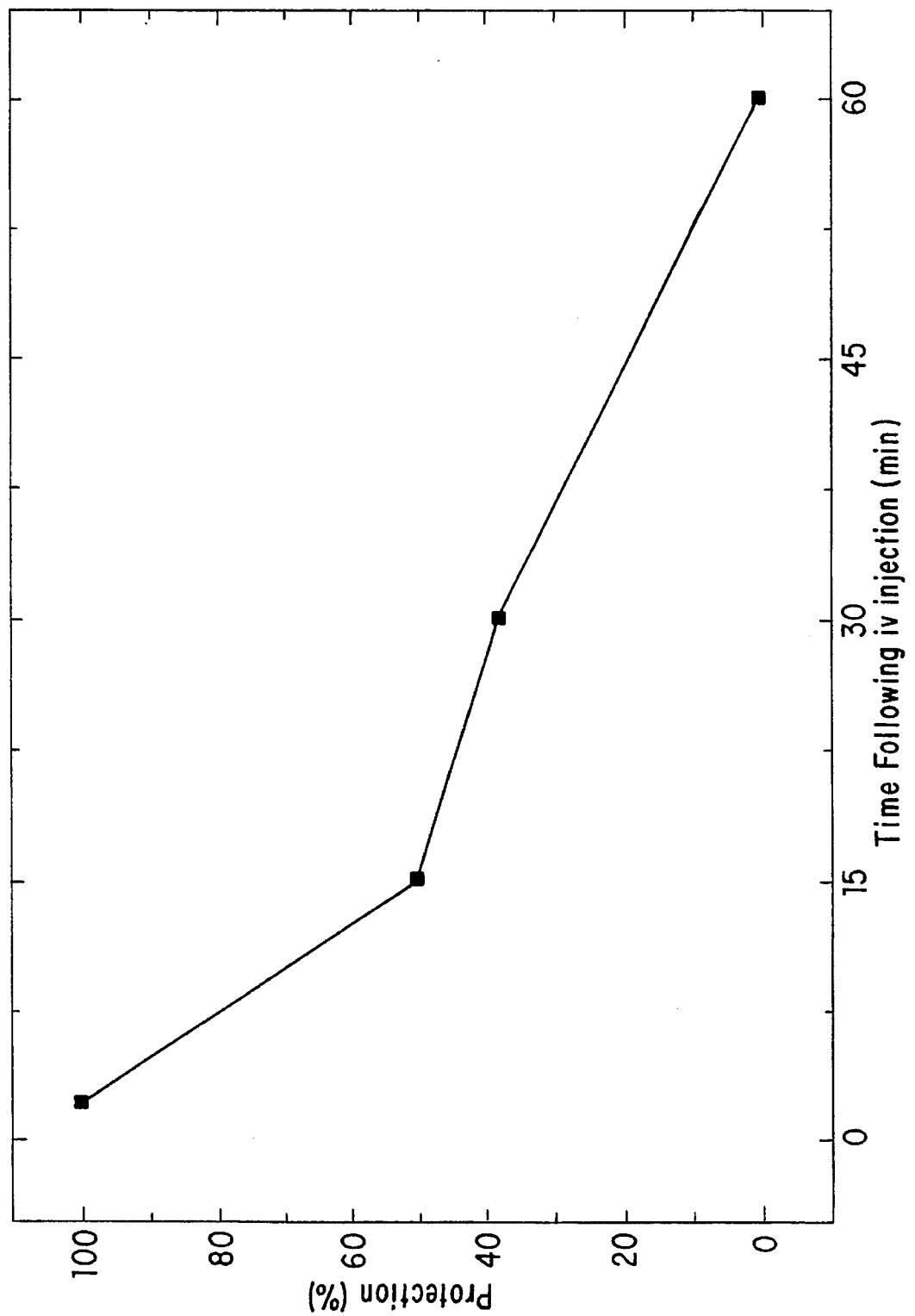
FIG. 1 depicts a graph showing the time course of 6-chloro-8-(N-oxy)aza-1,4-dihydroquinoxaline-2,3-dione (5 mg/kg, i.v.) in the inhibition of maximum electroshock induced seizure (MES).

The compounds which may be used in the practice of the invention have the Formulae:

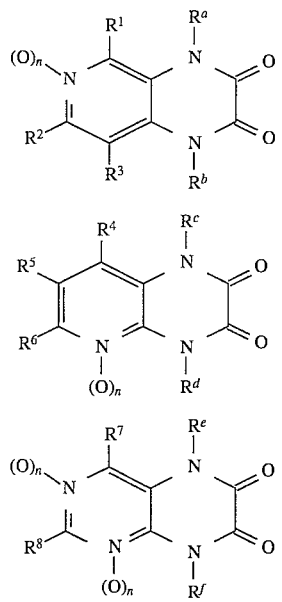

Of course, it is to be understood that $R^1$–$R^8$ and $R^a$–$R^f$ may be the same or different. It is also to be understood that the 6-aza, 8-aza, and 6,8-diaza-1,4-dihydroquinoxaline-2,3-diones of the present invention exist as tautomeric isomers. The present invention is also directed to such tautomeric isomers and mixtures of such isomers.

With respect to Formula I, when $R^a$ is other than hydrogen, then $R^b$ is hydrogen, and $R^3$ is hydrogen or fluoro; when $R^b$ is other than hydrogen, then $R^a$ is hydrogen, and $R^1$ is hydrogen or fluoro. Preferred compounds within the scope of Formula I are wherein one of $R^1$ and $R^3$ is hydrogen or is fluoro, e.g., $R^1$ and $R^2$ are independently nitro, amino, halo, haloalkyl, cyano, alkyl, alkenyl, alkynyl, azido, acylamino, alkylsulfonyl, aryl, substituted aryl, heteroaryl, alkoxy, trialkylsilyl-substituted alkoxy, aryloxy, substituted aryloxy, heteroaryloxy, a heterocyclic group, a heterocyclicoxy group, aralkoxy, or haloalkoxy; $R^3$ is hydrogen or fluoro; n is 0 or 1; and $R^a$ and $R^b$ are hydrogen. Alternatively, $R^1$ is hydrogen or fluoro; $R^2$ and $R^3$ are independently nitro, amino, halo, haloalkyl, cyano, alkyl, alkenyl, alkynyl, azido, acylamino, alkylsulfonyl, aryl, substituted aryl, heteroaryl, alkoxy, trialkylsilyl-substituted alkoxy, aryloxy, substituted aryloxy, heteroaryloxy, a heterocyclic group, a heterocyclicoxy group, aralkoxy, or haloalkoxy; n is 0 or 1; and $R^a$ and $R^b$ are hydrogen. Other preferred compounds include those wherein at least one of $R^1$, $R^2$ and $R^3$ is a halo or haloalkyl group. Other preferred compounds are those wherein one of $R^1$ and $R^3$ is fluoro and the other is not hydrogen; $R^2$ is not hydrogen; and $R^a$ and $R^b$ are hydrogen. The most preferred compounds having Formula I are wherein $R^1$ is nitro, halo, haloalkyl, alkyl, or azido; $R^2$ is nitro, halo, haloalkyl, alkyl, or azido; $R^3$ is hydrogen or fluoro; n is 0 or 1; and $R^a$ and $R^b$ are hydrogen; or wherein $R^1$ is hydrogen or fluoro; $R^2$ is nitro, halo, haloalkyl, alkyl, or azido; $R^3$ is nitro, halo, haloalkyl, alkyl, or azido; n is 0 or 1; and $R^a$ and $R^b$ are hydrogen.

Especially preferred compounds within the scope of Formula I include 5,7-dichloro-6-aza-1,4-dihydroquinoxaline-2,3-dione; 5,7-dimethyl-6-aza-1,4-dihydroquinoxaline-2,3-dione; 5,7-dibromo-6-aza-1,4-dihydroquinoxaline-2,3-dione; 5,7-difluoro-6-aza-1,4-dihydroquinoxaline-2,3-dione; 5,7-dichloro-6-(N-oxy)aza-1,4-dihydroquinoxaline-2,3-dione; 7-chloro-5-nitro-6-aza-1,4-dihydroquinoxaline-2,3-dione; 7-methyl-5-nitro-6-aza-1,4-dihydroquinoxaline-2,3-dione; 7-fluoro-5-nitro-6-aza-1,4-dihydroquinoxaline-2,3-dione; 7-bromo-5-nitro-6-aza-1,4-dihydroquinoxaline-2,3-dione; 4-hydroxy-5-nitro-6-aza-7-chloro-1,4-dihydroquinoxaline-2,3-dione; 4-hydroxy-5-nitro-6-aza-7-methyl-1,4-dihydroquinoxaline-2,3-dione; 4-hydroxy-5,7-dichloro-6-aza-1,4-dihydroquinoxaline-2,3-dione; 4-hydroxy-5-nitro-6-aza-7-fluoro-1,4-dihydroquinoxaline-2,3-dione; 4-hydroxy-5,7-difluoro-6-aza-1,4-dihydroquinoxaline-2,3-dione; 4-benzamido-5-nitro-6-aza-7-chloro-1,4-dihydroquinoxaline-2,3-dione; 4-phenacylamino-5-nitro-6-aza-7-chloro-1,4-dihydroquinoxaline-2,3-dione; 4-(N'-phenylureido)-5-nitro-6-aza-7-chloro-1,4-dihydroquinoxaline-2,3-dione; and 4-[2-(phenylaminocarbonyl)ethyl]-5-nitro-6-aza-7-chloro-1,4-dihydroquinoxaline-2,3-dione.

With respect to Formula II, when $R^c$ is other than hydrogen, then $R^d$ is hydrogen and n is 0; when $R^d$ is other than hydrogen, then $R^c$ is hydrogen and $R^4$ is hydrogen or fluoro. Preferred compounds are those wherein $R^5$ and $R^6$ are independently nitro, amino, halo, haloalkyl, cyano, alkyl, alkenyl, alkynyl, azido, acylamino, alkylsulfonyl, aryl, substituted aryl, heteroaryl, alkoxy, trialkylsilyl-substituted alkoxy, aryloxy, substituted aryloxy, heteroaryloxy, a heterocyclic group, a heterocyclicoxy group, aralkoxy, or haloalkoxy; $R^4$ is hydrogen or fluoro; n is 0 or 1; and $R^c$ and $R^d$ are hydrogen. Or $R^4$, $R^5$, and $R^6$ are anything but hydrogen; n is 0; and $R^c$ and $R^d$ are hydrogen. Or $R^4$ and $R^6$ are anything but hydrogen; $R^5$ is hydrogen; n is 0; and $R^c$ and $R^d$ are hydrogen. The most preferred compounds having Formula II are those wherein $R^4$ is nitro, halo, haloalkyl, alkyl, or azido; $R^5$ is nitro, halo, haloalkyl, alkyl, azido, or hydrogen; $R^6$ is nitro, halo, haloalkyl, alkyl, or azido; n is 0; and $R^c$ and $R^d$ are hydrogen. Or $R^4$ is hydrogen or fluoro; $R^5$ is nitro, halo, haloalkyl, alkyl, or azido; $R^6$ is nitro, halo, haloalkyl, alkyl, or azido; n is 1; and $R^c$ and $R^d$ are hydrogen. Or $R^5$ is anything but hydrogen; $R^4$ and $R^6$ are hydrogen; n is 1; and $R^c$ and $R^a$ are hydrogen.

Especially preferred compounds within the scope of Formula II include 6,7-dichloro-5-nitro-8-aza-1,4-dihydroquinoxaline-2,3-dione; 6-bromo-7-methyl-5-nitro-8-(N-oxy)aza-1,4-dihydroquinoxaline-2,3-dione; 6-bromo-7-methyl-5-nitro-8-aza-1,4-dihydroquinoxaline-2,3-dione; 6,7-dichloro-8-(N-oxy)aza-1,4-dihydroquinoxaline-2,3-dione; 6-chloro-8-(N-oxy)aza-1,4-dihydroquinoxaline-2,3-dione; 8-aza-6-chloro-1,4-dihydroquinoxaline-2,3-dione; 8-aza-6-bromo-1,4-dihydroquinoxaline-2,3-dione; 8-(N-oxy)aza-6-bromo-1,4-dihydroquinoxaline-2,3-dione; 6,7-dichloro-8-aza-1,4-dihydroquinoxaline-2,3-dione; 6-bromo-7-methyl-8-aza-1,4-dihydroquinoxaline-2,3-dione; 6-bromo-7-methyl-8-(N-oxy)aza-1,4-dihydroquinoxaline-2,3-dione; 8-aza-6-chloro-7-methyl-1,4-dihydroquinoxaline-2,3-dione; 8-(N-oxy)aza-6-chloro-7-methyl-1,4-dihydroquinoxaline-2,3-dione; 6-chloro-7-bromo-5-nitro-8-aza-1,4-dihydroquinoxaline-2,3-dione; 6-chloro-7-bromo-8-(N-oxy)aza-1,4-dihydroquinoxaline-2,3-dione; 8-aza-6-methyl-1,4-dihydroquinoxaline-2,3-dione; 8-(N-oxy)aza-6-methyl-1,4-dihydroquinoxaline-2,3-dione; 5,7-dimethyl-8-aza-1,4-dihydroquinoxaline-2,3-dione; 5,7-dibromo-8-aza-1,4-dihydroquinoxaline-2,3-dione; 5,7-difluoro-8-aza-1,4-dihydroquinoxaline-2,3dione; 5,7-dichloro-8-aza-1,4-dihydroquinoxaline-2,3-dione; 7-chloro-5-nitro-8-aza-1,4-dihydroquinoxaline-2,3-dione; 7-methyl-5-nitro-8-aza-1,4- dihydroquinoxaline-2,3-dione; 7-fluoro-5-nitro-8-aza-1,4-dihydroquinoxaline-2,3-dione; 7-bromo-5-nitro-8-aza-1,4-dihydroquinoxaline-2,3-dione; 7-trifluoromethyl-5-nitro-8-aza-1,4-dihydroquinoxaline-2,3-dione; 5-chloro-7-trifluoromethyl-8-aza-1,4-dihydroquinoxaline-2,3-dione; 4-hydroxy-5-nitro-8-aza-7-chloro-1,4-dihydroquinoxaline-2,3-dione; 4-hydroxy-5-nitro-8-aza-7-methyl-1,4-dihydroquinoxaline-2,3-dione; 4-hydroxy-5,7-dichloro-8-aza-1,4-dihydroquinoxaline-2,3-dione; 4-hydroxy-5,7-difluoro-8-aza-1,4-dihydroquinoxaline-2,3-dione; 4-benzamido-5-nitro-8-aza-7-chloro-1,4-dihydroquinoxaline-2,3-dione; 4-phenacylamino-5-nitro-8-aza-7-chloro-1,4-dihydroquinoxaline-2,3-dione; 4-(N'-phenylureido)-5-nitro-8-aza-7-chloro-1,4-dihydroquinoxaline-2,3-dione; 4-[2-(phenylaminocarbonyl)ethyl]-5-nitro-8-aza-7-chloro-1,4-dihydroquinoxaline-2,3-dione; 8-aza-6-trifluoromethyl-1,4-dihydroquinoxaline-2,3-dione; 8-(N-oxy)aza-6-trifluoromethyl-1,4-dihydroquinoxaline-2,3-dione; 8-aza-5-methyl-1,4-dihydroquinoxaline-2,3-dione; 5-methyl-8-(N-oxy)aza-1,4-dihydroquinoxaline-2,3-dione; 7-chloro-6-methyl-8-nitro-5-(N-oxy)aza-1,4-dihydroquinoxaline-2,3-dione; 5-aza-7-chloro-6-methyl-8-nitro-1,4-dihydroquinoxaline-2,3-dione; 5-aza-7-nitro-1,4-dihydroquinoxaline-2,3-dione; 7-nitro-5-(N-oxy)aza-1,4-dihydroquinoxaline-2,3-dione; 5-aza-7-carbamoyl-1,4-dihydroquinoxaline-2,3-dione; and 7-carbamoyl-5-(N-oxy)aza-1,4-dihydroquinoxaline-2,3-dione.

With respect to Formula III, when $R^e$ is other than hydrogen, then $R^f$ is hydrogen and n is 0; when $R^f$ is other than hydrogen, then $R^e$ is hydrogen and $R^7$ is hydrogen or fluoro. Preferred compounds are those wherein $R^7$ and $R^8$ are other than hydrogen. Other preferred compounds are those wherein $R^7$ is hydrogen or fluoro; $R^8$ is nitro, amino, halo, haloalkyl, cyano, alkyl, alkenyl, alkynyl, azido, acylamino, alkylsulfonyl, aryl, substituted aryl, heteroaryl, alkoxy, trialkylsilyl-substituted alkoxy, aryloxy, substituted aryloxy, heteroaryloxy, a heterocyclic group, a heterocyclicoxy group, aralkoxy, or haloalkoxy; and n is 0. Other preferred compounds are those wherein at least one of $R^7$ and $R^8$ is a halo or haloalkyl group. The most preferred compounds having Formula III are those wherein $R^7$ is nitro, halo, haloalkyl, alkyl, or azido; and $R^8$ is nitro, halo, haloalkyl, alkyl, or azido.

Especially preferred compounds within the scope of Formula III include 5,7-dimethyl-6,8-diaza-1,4-dihydroquinoxaline-2,3-dione; 5,7-dichloro-6,8-diaza-1,4-dihydroquinoxaline-2,3-dione; 5,7-dimethyl-6,8-diaza-4-hydroxy-1,4-dihydroquinoxaline-2,3-dione; 5-nitro-7-chloro-6,8-diaza-1,4-dihydroquinoxaline-2,3-dione; 5,7-bis(trifluoromethyl)-6,8-diaza-1,4-dihydroquinoxaline-2,3-dione; 4-hydroxy-5-nitro-6,8-diaza-7-chloro-1,4-dihydroquinoxaline-2,3-dione; 4-hydroxy-5,7-dichloro-6,8-diaza-1,4-dihydroquinoxaline-2,3-dione; 4-hydroxy-5,7-difluoro-6,8-diaza-1,4-dihydroquinoxaline-2,3-dione; 4-benzamido-5-nitro-6,8-diaza-7-chloro-1,4-dihydroquinoxaline-2,3-dione; 4-phenacylamino-5-nitro-6,8-diaza-7-chloro-1,4-dihydroquinoxaline-2,3-dione; 4-(N'-phenylureido)-5-nitro-6,8-diaza-7-chloro-1,4-dihydroquinoxaline-2,3-dione; 4-[2-(phenylaminocarbonyl)ethyl]-5-nitro-6,8-diaza-7-chloro-1,4-dihydroquinoxaline-2,3-dione; 6,8-di(N-oxy)aza-1,4-dihydroquinoxaline-2,3-dione, 6,8-di-(N-oxy)aza-7-methyl-1,4-dihydroquinoxaline-2,3-dione; 6,8-di(N-oxy)aza-7-chloro-1,4-dihydroquinoxaline-2,3-dione; 7-chloro-6,8-diaza-6-(N-oxy)-1,4-dihydroquinoxaline-2,3-dione; 7-chloro-6,8-diaza-8-(N-oxy)-1,4-dihydroquinoxaline-2,3-dione; 7-chloro-6,8-diaza-6,8-di(N-oxy)-1,4-dihydroquinoxaline-2,3-dione; 7-bromo-6,8-diaza-6-(N-oxy)-1,4-dihydroquinoxaline-2,3-dione; 7-bromo-6,8-diaza-8-(N-oxy)-1,4-dihydroquinoxaline-2,3-dione; 7-bromo-6,8-diaza-6,8-di(N-oxy)-1,4-dihydroquinoxaline-2,3-dione; and 8-(N-oxy)-6,8-diaza-1,4-dihydroquinoxaline-2,3-dione.

In general, preferred compounds having high binding to the glycine receptor are substituted in each available position (5-, 6-, 7- and 8-positions). Other preferred compounds are unsubstituted or are substituted by fluorine in the 5- or 8-position in order to avoid steric interference with the interaction of the NH in the 1-position with the receptor (probably by hydrogen bonding). Preferred compounds also have electron withdrawing substituents, such as $NO_2$ in the 5- or 8-position, plus 6,7-substituents, such as, halogen and alkyl. The electron withdrawing substituents in the 5- or 8-position are also very important to render the NH acidic, which is critical for the formulation of the compounds in aqueous basic solution. The aza group is considered to function as an electron withdrawing substituent similar to $NO_2$. The replacement of the CH with N does not introduce any steric interference effect. It is therefore expected that the pyridine and pyrimidine analogs of QX described herein should behave similarly to the corresponding 1,4-dihydroquinoxaline-2,3-diones (QXs) that have high binding to the glycine receptor. It is also expected that the pyridine and pyrimidine analogs of QX will be easier to formulate in pharmaceutical compositions that are soluble in aqueous solutions, compared to QX itself, especially for those having aza groups in the 8-position. Since log $P_{benzene}$=2.15 and log $P_{pyridine\ N\text{-}oxide}$=−1.69 (see, Leo et al., Chem. Rev. 71:525 (1971), there is a difference in log P of −3.84 from benzene to pyridine N-oxide. It is therefore expected that the N-oxide pyridine and N-oxide pyrimidine analogs of the 1,4-dihydroquinoxaline-2,3-diones will have a lower log P and will be more water soluble compared to the corresponding 1,4-dihydroquinoxaline-2,3-dione.

Typical $C_{6-14}$ aryl groups include phenyl, naphthyl, phenanthryl, anthracyl, indenyl, azulenyl, biphenyl, biphenylenyl, and fluorenyl groups.

Typical aryloxy groups include any of the $C_{6-14}$ aryl groups linked by oxygen, e.g., phenoxy and 1-naphthyloxy groups.

Typical substituted aryl groups include any of the $C_{6-14}$ aryl groups substituted by one or more halo, nitro, cyano, alkyl, alkenyl, and alkynyl groups, e.g., 2-chlorophenyl, 2,4-dibromophenyl, and the like.

Typical substituted aryloxy groups include any of the $C_{6-14}$ aryl groups substituted by one or more halo, nitro, cyano, alkyl, alkenyl, and alkynyl groups, and linked by oxygen, e.g., 2-chlorophenoxy, 2,4-dibromophenoxy, and the like.

Typical aryloyl groups include any of the above-mentioned aryl groups substituted by a carbonyl group.

Preferred heterocyclic groups are those having 3 to 10 carbon atoms and having one or more 4, 5, 6, or 7 member saturated or unsaturated rings containing 1, 2, or 3 oxygen, nitrogen or sulfur heteroatoms (where examples of heterocyclic radicals are: tetrahydrofuran, 1,4-dioxane, 1,3,5-trioxane, pyrrolidine, piperidine, piperazine, imadazoline, isoindoline, chromane, isochromane, pyrazolidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furrural, furfuryl alcohol, carbazole, isoquinoline, 3-pyrroline, thiophene, furan, hexamethyleneimine, ε-caprolactone, ε-caprolactam, omega-thiocaprolactam, and morpholine).

Typical heteroaryl groups have 3 to 14 ring atoms; 6, 10 or 14 π electrons shared in a cyclic array; and contain carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups). N-oxide analogs of ring-nitrogen containing heteroaryl groups are also contemplated. An example is (3-N-oxy)imidazol-1-yl.

Typical heteroaryloxy groups include any of the heteroaryl groups linked by oxygen, e.g. 2-furanoxy, 4-pyridoxy, 2-pyrazinoxy, purine-6-oxy and the like.

Typical heterocyclicoxy groups include any of the heterocyclic groups linked by oxygen, e.g. 4-tetrahydropyranyloxy.

Typical amino groups include $NH_2$, $NHR_5$, and $NR_5R^6$, wherein $R_5$ and $R^6$ are $C_{1-4}$ alkyl groups.

Typical halo groups include fluorine, chlorine, bromine, and iodine.

Typical $C_{1-4}$ alkyl groups include methyl, ethyl, propyl, isopropyl, butyl, sec.-butyl, and tert.-butyl groups.

Typical $C_{3-8}$ cycloalkyl groups include cyclopropyl, cyclobutyl, cyclopentyl, cyclohexyl, cycloheptyl, and cyclooctyl groups.

Typical $C_{2-4}$ alkenyl groups include vinyl, allyl, 1-butenyl, 2-butenyl, 3-butenyl, and isobutenyl groups.

Typical $C_{2-4}$ alkynyl groups include propargyl, 1-propynyl, 2-propynyl, 1-butynyl, 2-butynyl, and 3-butynyl groups.

Typical aralkoxy groups include $C_{1-4}$ alkoxy groups substituted by any one of the aryl groups mentioned above.

Typical haloalkyl groups include $C_{1-4}$ alkyl groups substituted by one or more fluorine, chlorine, bromine, or iodine atoms, e.g., fluoromethyl, difluoromethyl, trifluoromethyl, pentafluoroethyl, 1,1-difluoroethyl, and trichloromethyl groups.

Typical alkoxy groups include any one of the $C_{1-4}$ alkyl groups mentioned above linked by oxygen.

Typical haloalkoxy groups include any one of the alkoxy groups substituted by one or more fluoro, chloro, bromo, or iodo groups, e.g., trifluoromethoxy, trichloromethoxy, 2-chloroethoxy, 2-bromoethoxy, pentafluoroethyl, 3,3,3-trichloropropoxy, 4,4,4-trichlorobutoxy, and the like.

Typical trialkylsilyl-substituted alkoxy groups include any one of the $C_{1-4}$ alkoxy groups substituted by a $C_{3-6}$ trialkylsilyl group, e.g. 2-trimethylsilylethoxy, 2-triethylsilylethoxy and 2-(t-butyldimethylsilyl)ethoxy, and the like.

Typical $C_2$–$C_6$ acyl (alkanoyl) groups include acetyl, propionyl, butanoyl, and pentanoyl groups.

Typical $C_2$–$C_6$ acyl groups substituted by halogen include the above-mentioned acyl groups substituted by one or more fluoro, chloro, bromo or iodo groups, e.g., trifluoroacetyl.

Where the 8-aza-, 6-aza-, and 6,8-diaza-1,4-dihydroquinoxaline-2,3-dione is substituted by a radical having Formula IV, the radical may be a $C_{2-7}$ carboxyalkyl group including carboxymethyl, 2-carboxyethyl, 3-carboxypropyl, 4-carboxybutyl, 5-carboxypentyl, 6-carboxyhexyl, 1-carboxyethyl, 1-carboxypropyl, 1-carboxybutyl, 1-carboxypentyl, 1-carboxyhexyl, 2-carboxypropyl, 2-carboxybutyl, 2-carboxypentyl, 2-carboxyhexyl, 3-carboxybutyl, 3-carboxypentyl, 3-carboxyhexyl, 5-carboxypentyl, 5-carboxyhexyl, and the like.

Typical $C_{8-2}$ carboxyaralkyl groups which are included in Formula IV include 1-aryl-2-carboxyethyl, 1-aryl-3-carboxypropyl, 1-aryl-4-carboxybutyl, 1-aryl-5-carboxypentyl, 1-aryl-6-carboxyhexyl, 1-aryl-1-carboxyethyl, 1-aryl-1-carboxypropyl, 1-aryl-1-carboxybutyl, 1-aryl-1-carboxypentyl, 1-aryl-1-carboxyhexyl, 1-aryl-2-carboxypropyl, 1-aryl-2-carboxybutyl, 1-aryl-2-carboxypentyl, 1-aryl-2-carboxyhexyl, 1-aryl-3-carboxybutyl, 1-aryl-3-carboxypentyl, 1-aryl-3-carboxyhexyl, 1-aryl-5-carboxypentyl, 1-aryl-5-carboxyhexyl, 2-aryl-2-carboxyethyl, 2-aryl-3-carboxypropyl, 2-aryl-4-carboxybutyl, 2-aryl-5-carboxypentyl, 2-aryl-6-carboxyhexyl, 2-aryl-1-carboxyethyl, 2-aryl-1-carboxypropyl, 2-aryl-1-carboxybutyl, 2-aryl-1-carboxypentyl, 2-aryl-1-carboxyhexyl, 2-aryl-2-carboxypropyl, 2-aryl-2-carboxybutyl, 2-aryl-2-carboxypentyl, 2-aryl-2-carboxyhexyl, 2-aryl-3-carboxybutyl, 2-aryl-3-carboxypentyl, 2-aryl-3-carboxyhexyl, 2-aryl-5-carboxypentyl, 2-aryl-5-carboxyhexyl, and the like.

The compounds of the present invention are expected to be potent anticonvulsants in animal models and will prevent ischemia-induced nerve cell death in the gerbil global ischemia model after i.p. or i.v. administration.

The compounds of the present invention are active in treating or preventing neuronal loss, neurodegenerative diseases, chronic pain, are active as anticonvulsants and antipsychotics and for inducing anesthesia. Certain of the compounds of the present invention are expected to exhibit little or no untoward side effects caused by non-selective binding with other receptors, particularly, the PCP and glutamate receptors associated with the NMDA receptor. In addition, certain of the compounds may block kainate, AMPA, and quisqualate receptors and are, therefore, useful as broad-spectrum excitatory amino acid receptor antagonists. Moreover, the compounds of the present invention are effective in treating or preventing the adverse consequences of the hyperactivity of the excitatory amino acids, e.g., those that are involved in the NMDA receptor system, by blocking the glycine receptors and preventing the ligand-gated cation channels from opening and allowing excessive influx of $Ca^{++}$ into neurons, as occurs during ischemia.

Neurodegenerative diseases that may be treated with the compounds of the present invention include those selected from the group consisting of Alzheimer's disease, amyotrophic lateral sclerosis, Huntington's disease, and Down's syndrome.

The compounds of the present invention find particular utility in the treatment or prevention of neuronal loss associated with multiple strokes, which gives rise to dementia. After a patient has been diagnosed as suffering from a stroke, the compounds of the present invention may be administered to ameliorate the immediate ischemia and prevent further neuronal damage that may occur from recurrent strokes.

Moreover, the compounds of the present invention are able to cross the blood/brain barrier, which makes them particularly useful for treating or preventing conditions involving the central nervous system.

The compounds of the invention find particular utility in treating or preventing the adverse neurological consequences of surgery. For example, coronary bypass surgery requires the use of heart-lung machines, which tend to introduce air bubbles into the circulatory system that may lodge in the brain. The presence of such air bubbles robs neuronal tissue of oxygen, resulting in anoxia and ischemia. Pre- or post-surgical administration of the compounds of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating or preventing pain, e.g., chronic pain. Such chronic pain can be the result of surgery, trauma, headache, arthritis, pain associated with terminal cases of cancer, or degenerative diseases. The compounds of the present invention find particular utility in the treatment of phantom pain that results from amputation of an extremity. In addition to treatment of pain, the compounds of the invention are also expected to be useful in inducing anesthesia, either general or local anesthesia, for example, during surgery.

The glycine and excitatory amino acid antagonists may be tested for in vivo anticonvulsant activity after intraperitoneal injection using a number of anticonvulsant tests in mice (audiogenic seizure model in DBA-2 mice, pentylenetetrazol-induced seizures in mice, NMDA-induced death, and MES). The compounds may also be tested in drug discrimination tests in rats trained to discriminate PCP from saline. It is expected that most of the compounds of the present invention will not generalize to PCP at any dose. In addition, it is also expected that none of the compounds will produce a behavioral excitation in locomotor activity tests in the mouse. It is expected that such results will suggest that the glycine, AMPA, kainate, and quisqualate antagonists of the present invention do not show the PCP-like behavioral side effects that are common to NMDA channel blockers, such as, MK-801 and PCP, or to competitive NMDA antagonists, such as, CGS19755.

The glycine and excitatory amino acid antagonists are also expected to show potent activity in vivo after intraperitoneal injection suggesting that these compounds can penetrate the blood/brain barrier.

It is well known to use opiates, e.g., morphine, in the medical field to alleviate pain. (As used herein, the term "opiates" is intended to mean any preparation or derivative of opium, especially the alkaloids naturally contained therein, of which there are about twenty, e.g., morphine, noscapine, codeine, papaverine, and thebaine, and their derivatives.) Unfortunately, with continued use, the body builds up a tolerance for the opiate, and, thus, for continued relief, the patient must be subjected to progressively larger doses. Tolerance develops after both acute and chronic morphine administration (Kornetsky et al., Science 162:1011–1012 (1968); Way et al., J. Pharmacol. Exp Ther. 167:1–8 (1969); Huidobro et al., J. Pharmacol. Exp Ther. 198:318–329 (1976); Lutfy et al., J. Pharmacol. Exp Ther. 256:575–580 (1991)). This, in itself, can be detrimental to the patient's health. Furthermore, a time can come when the tolerance is substantially complete and the pain killing properties of the drug are no longer effective. Additionally, administration of higher doses of morphine may lead to respiratory depression, causing the patient to stop breathing. Seeking alternative drugs to produce analgesia without development of tolerance or as an adjunct therapy to block tolerance without interference with analgesia is an active area of research.

Recent studies have suggested a modulatory role for the NMDA receptor in morphine tolerance. (Trujillo et al., Science 251:85–87 (1991); Marek et al., Brain Res. 547:77–81 (1991); Tiseo et al., J. Pharmacol. Exp Ther. 264:1090–1096 (1993); Lutfy et al., Brain Res. 616:83–88 (1993).) The present invention is also directed to the administration of the compounds described herein to inhibit opiate tolerance by blocking the glycine co-agonist site associated with the NMDA receptor.

The compounds of the present invention may be tested for potential glycine antagonist activity by observing the inhibition of binding of 1 µM glycine-stimulated [$^3$H]-MK-801 in rat or guinea pig brain membrane homogenates. The more potent the glycine antagonist, the less [$^3$H]-MK-801 can bind since the [$^3$H]-MK801 binding site (PCP receptor) is accessible only upon opening of the ion channel by glutamate and glycine (Fletcher, E. L., et al., in Glycine Neurotransmission, Otterson, P., et al., eds., John Wiley and Sons (1990); Johnson, J. W., et al., Nature 325:529 (1987)).

The compounds of the present invention may be prepared as follows. It has been reported that reduction of 2-amino-5-chloro-3-nitropyridine (2) by SnCl$_2$ in concentrated HCl resulted in both reduction of the nitro group to an amino group as well as chlorination of the pyridine ring to give 2,3-diamino-5,6-dichloropyridine (4) as the only isolated product (Israel & Day, J. Org. Chem. 24:1455–1460 (1959)). We found that reduction of 2 under identical conditions as reported gave a mixture of 2,3-diamino-5-chloropyridine (3) and 2,3-diamino-5,6-dichloropyridine (4) in a ratio of 4:1. The mixture could not be separated by crystallization in water. It could be separated by preparative TLC and chromatography. Cyclization of 3 with oxalic acid gave 8-NQX 5 and cyclization of 4 with oxalic acid gave 8-NQX 6. 6,7-dichloro-8-NQX 6 was found to have a K$_i$ of about 200 nM, which is similar to the corresponding 6,7-dichloro-QX. 6-Chloro-8-NQX 5 also was found to be about as active as the corresponding 6-chloro-QX. 6-Bromo-7-methyl-8-NQX (8) was found to have a K$_i$ of about 200 nM. 6-NQX 11 and 6,8-diN-QX 13 also were found to be about as active as QX.

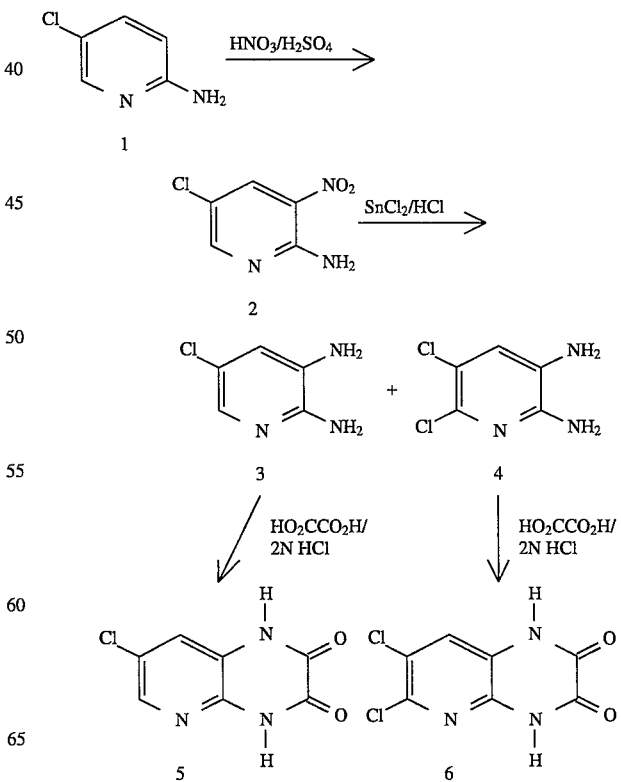

-continued
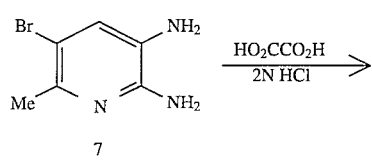
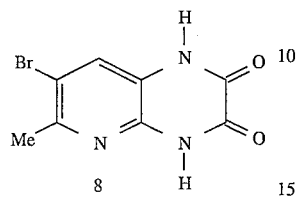
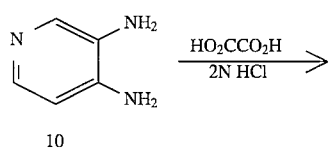
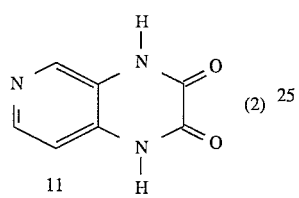
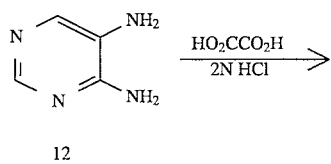
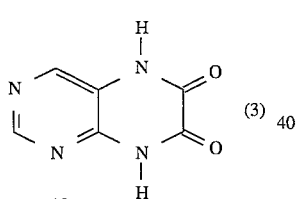
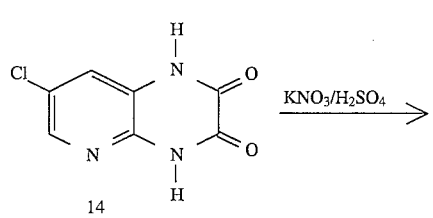
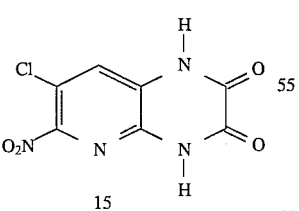
-continued
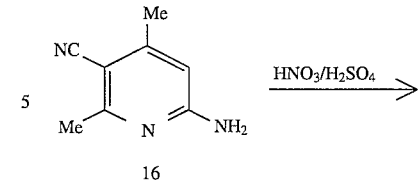
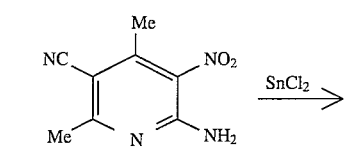
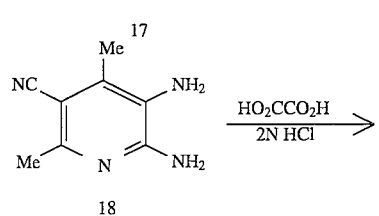
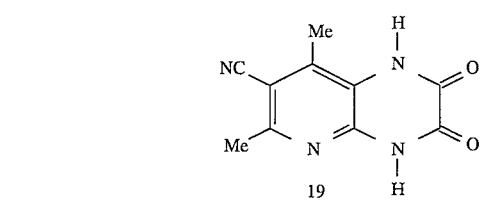
The N-oxides may be prepared by oxidation of the pyridine nitrogen by peracetic acid (Israel & Day, J. Org. Chem. 24:1455–1460 (1959)), or by oxidation with m-chloroperbenzoic acid (mCPBA) (Daines, R. A., et al., J. Med. Chem. 36:3321–3332 (1993)). Nitration of 20 in $H_2SO_4$ with fuming nitric acid will give 21. The N-oxide could be removed by treatment with $PCl_3$ to give 22.
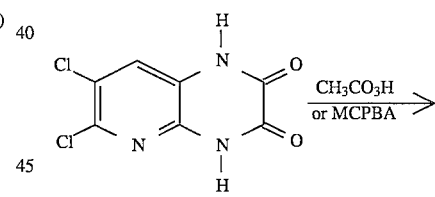
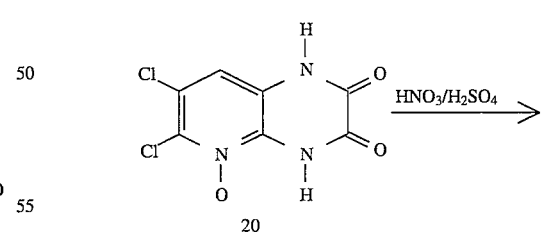
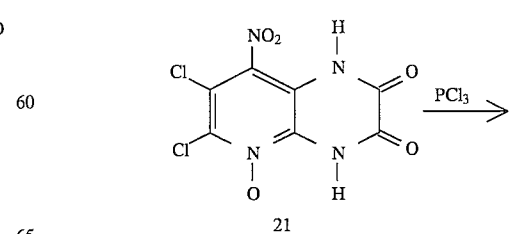

-continued

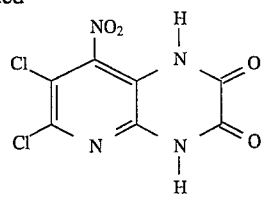

22

Using analogous methods, the following compounds may also be prepared:

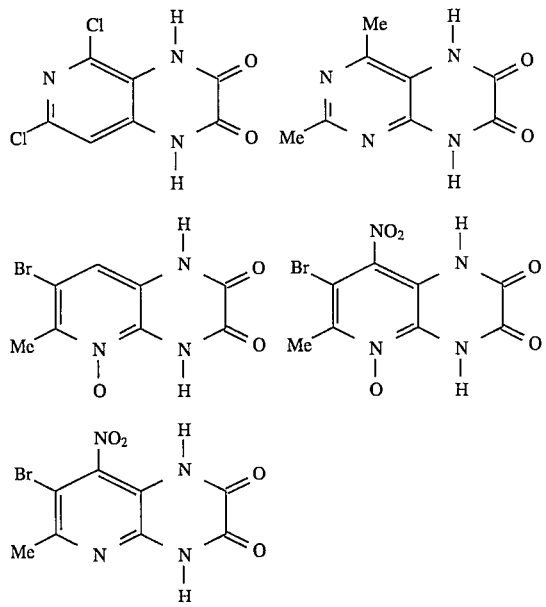

Where $R^a$, $R^b$, $R^c$, $R^d$, $R^e$, or $R^f$ is CH$_2$CONHAr, the compounds may be prepared by reaction of the corresponding substituted o-pyridinediamine or o-pyrimidinediamine with aqueous sodium chloroacetate solution followed by acidification to give the corresponding N$^1$-carboxymethyl-(6-aza, 8-aza, or 6,8-diaza)quinoxalin-3(1H)-one. Oxidation of this product with alkaline KMnO$_4$ gives the N-carboxymethyl-(6-aza, 8-aza, or 6,8-diaza)-1,4-dihydroquinoxaline-2,3-dione. This compound can be converted to the aryl amide by condensation with an arylamine in the presence of dicyclohexyl-carbodiimide in DMF.

Alternatively, where $R^a$, $R^b$, $R^c$, $R^d$, $R^e$, or $R^f$ is CH$_2$CONHAr, the compounds may be prepared by condensation of the corresponding substituted o-pyridinediamine or o-pyrimidinediamine with glyoxalic acid in ethanol to give the corresponding (6-aza, 8-aza, or 6,8-diaza)quinoxaline-3(2H)-3-one. See, Barton, D. E., et al., J. Chem. Soc. (C), 1268 (1968). This product can be N-alkylated with a sodium alkoxide and a reactive a-halo ethyl ester to give the N$^4$-carboxymethyl-(6-aza, 8-aza or 6,8-diaza)quinoxaline-3(2H)-one ethyl ester. Finally, oxidation with hydrogen peroxide gives the N-carboxymethyl-(6-aza, 8-aza, or 6,8-diaza)-1,4-dihydroquinoxaline-2,3-dione.

Alternatively, where $R^a$, $R^b$, $R^c$, $R^d$, $R^e$, or $R^f$ is CH$_2$CONHAr, the compounds may be prepared by N-alkylation of the corresponding anion with a reactive halide. For example, deprotonation of 6,7-dichloro-5-nitro-8-aza-1,4-dihydroquinoxaline-2,3-dione with a base, such as, lithium diisopropylamide, will give the corresponding anion. Alkylation with an α-haloester, such as, methyl bromoacetate, followed by ester hydrolysis will give the corresponding N-substituted acetic acid. Condensation of the N-substituted acetic acid with an arylamine in the presence of a dehydrating agent, such as, DCC, gives the anilide.

Where $R^a$, $R^b$, $R^c$, $R^d$, $R^e$, or $R^f$ is —NHCONHAr, the compounds may be prepared by reaction of the aminate anion, obtained by deprotonation of the 6-aza, 8-aza, or 6,8-diaza-1,4-dihydroquinoxaline-2,3-dione, with chloramine or mesitylenesulfonyl-oxyamine (Tamura, Y. et al., Synthesis 1(1977)) to give the N-amino 6-aza, 8-aza, or 6,8-diaza-1,4-dihydroquinoxaline-2,3-dione intermediate. Alternatively, the nitrogen can be amidated by reaction of the 6-aza, 8-aza, or 6,8-diaza-1,4-quinoxaline-2,3-dione with hydroxylamine-O-sulfonic acid in aqueous sodium hydroxide according to Shin & Lee, J. Korean Chem. Soc. 27:382–384 (1983) to give the N$^1$- and/or N$^4$-amino-6-aza, 8-aza, or 6,8-diaza-1,4-quinoxaline-2,3-diones. Alternatively, such compounds can be prepared from the N-alkylated o-pyridinediamine or o-pyrimidinediamine by condensation with diethyl oxalate. See also, International Application Publication No. WO91/13878, the contents of which are fully incorporated by reference herein, for methods of preparing N-substituted carboxyalkyl and carboxyaralkyl 1,4-dihydroquinoxaline-2,3-diones, as well as the N-hydroxy-1,4-dihydroquinoxaline-2,3-diones.

A group of aza-1,4-dihydroquinoxaline-2,3-diones and 8-(N-oxy)aza-1,4-dihydroquinoxaline-2,3-diones have been prepared and found to be active antagonists of the glycine/NMDA receptor. Some of the 8-(N-oxy)aza-1,4-dihydroquinoxaline-2,3-diones also have been found to be unexpectedly active in vivo in MES experiments. Therefore, these compounds are able to pass the blood-brain-barrier at high levels.

6-Aza-5,7-dichloro-1,4-dihydroquinoxaline-2,3-dione (25) was prepared as shown in eq 4. Nitration of 4-amino-2,6-dichloropyridine gave 4-amino-2,6-dichloro-5-nitropyridine (23), which was reduced by Tin(II) chloride to give 4,5-diamino-2,6-dichloropyridine (24). Condensation of 24 with oxalic acid in 2N HCl produced 25. The corresponding N-hydroxy derivative 30 was prepared (eq 5) by reacting amine 3 with ethyl oxalyl chloride to give amide 29, which was reduced by catalytic hydrogenation, giving 6-aza-5,7-dichloro-4-N-hydroxy-1,4-dihydroquinoxaline-2,3-dione (30).

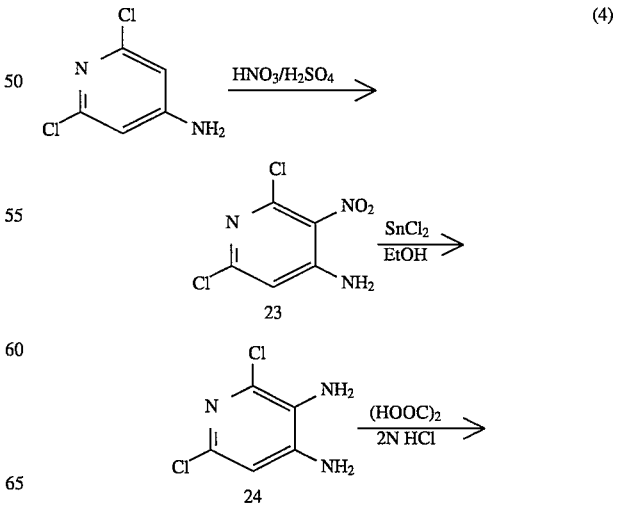

(4)

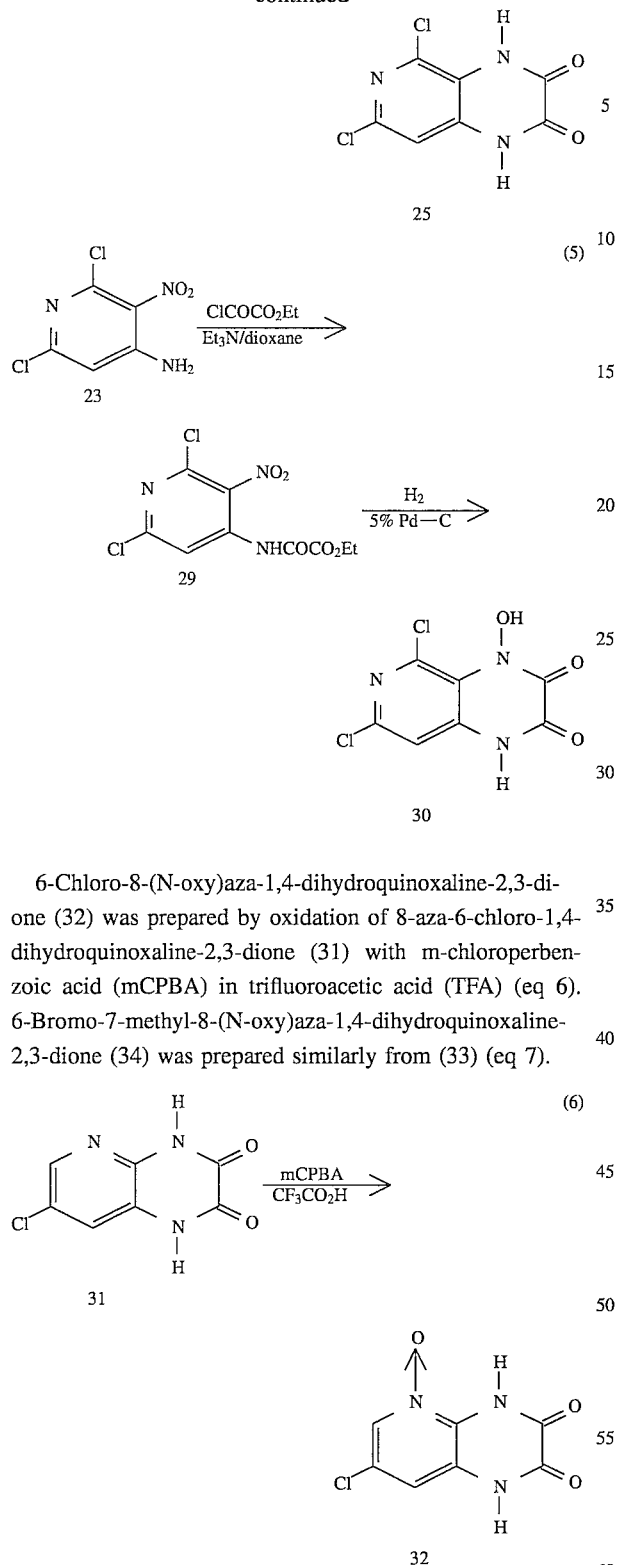

6-Chloro-8-(N-oxy)aza-1,4-dihydroquinoxaline-2,3-dione (32) was prepared by oxidation of 8-aza-6-chloro-1,4-dihydroquinoxaline-2,3-dione (31) with m-chloroperbenzoic acid (mCPBA) in trifluoroacetic acid (TFA) (eq 6). 6-Bromo-7-methyl-8-(N-oxy)aza-1,4-dihydroquinoxaline-2,3-dione (34) was prepared similarly from (33) (eq 7).

8-Aza-6-methyl-1,4-dihydroquinoxaline-2,3-dione (41) was prepared similarly by nitration of 2-amino-5-methylpyridine, followed by reduction of nitropyridine 38 and cyclization of diaminopyridine 39 with oxalic acid. Oxidation of 41 by mCPBA in TFA gave 8-(N-oxy)aza-6-methyl-1,4-dihydroquinoxaline-2,3-dione (43) (eq 8). 8-Aza-6-bromo-1,4-dihydroquinoxaline-2,3-dione (42) and 8-(N-oxy)aza-6-bromo-1,4-dihydroquinoxaline-2,3-dione (44) were prepared similarly from 2-amino-5-bromo-3-nitropyridine (eq 9).

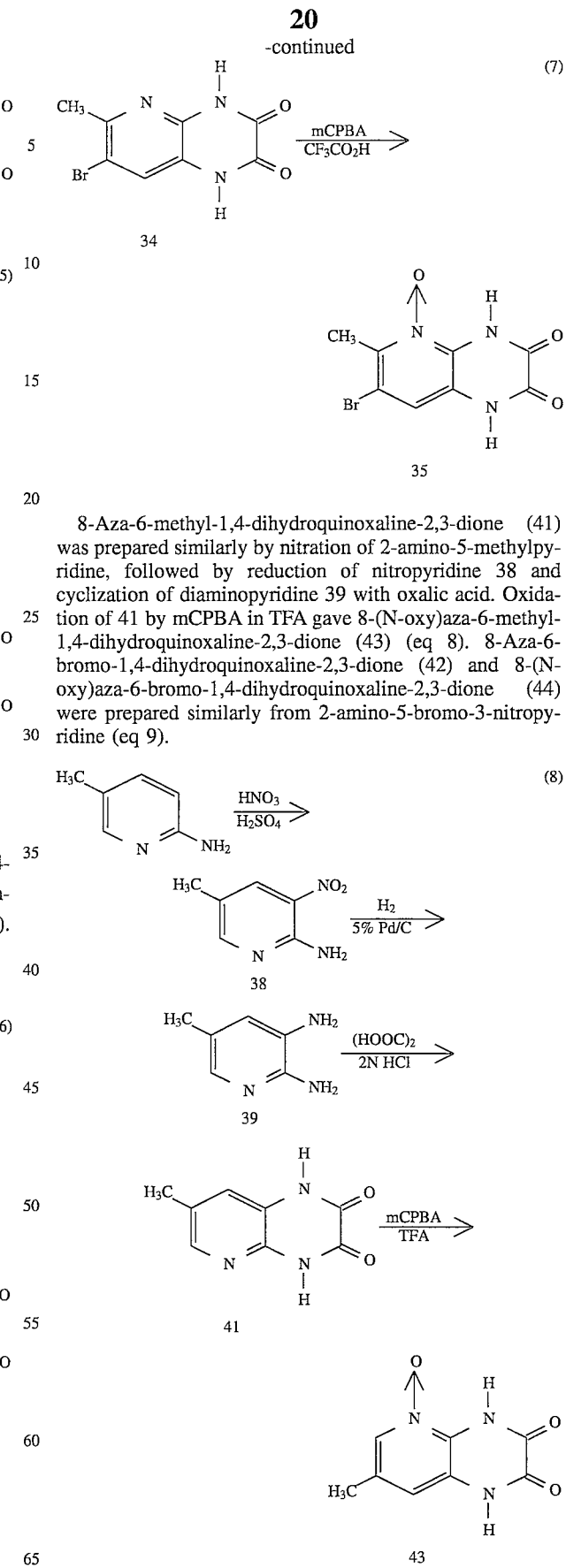

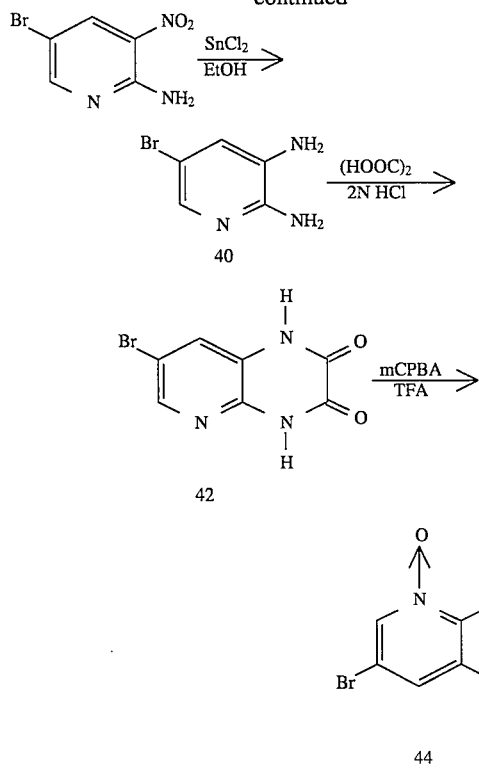

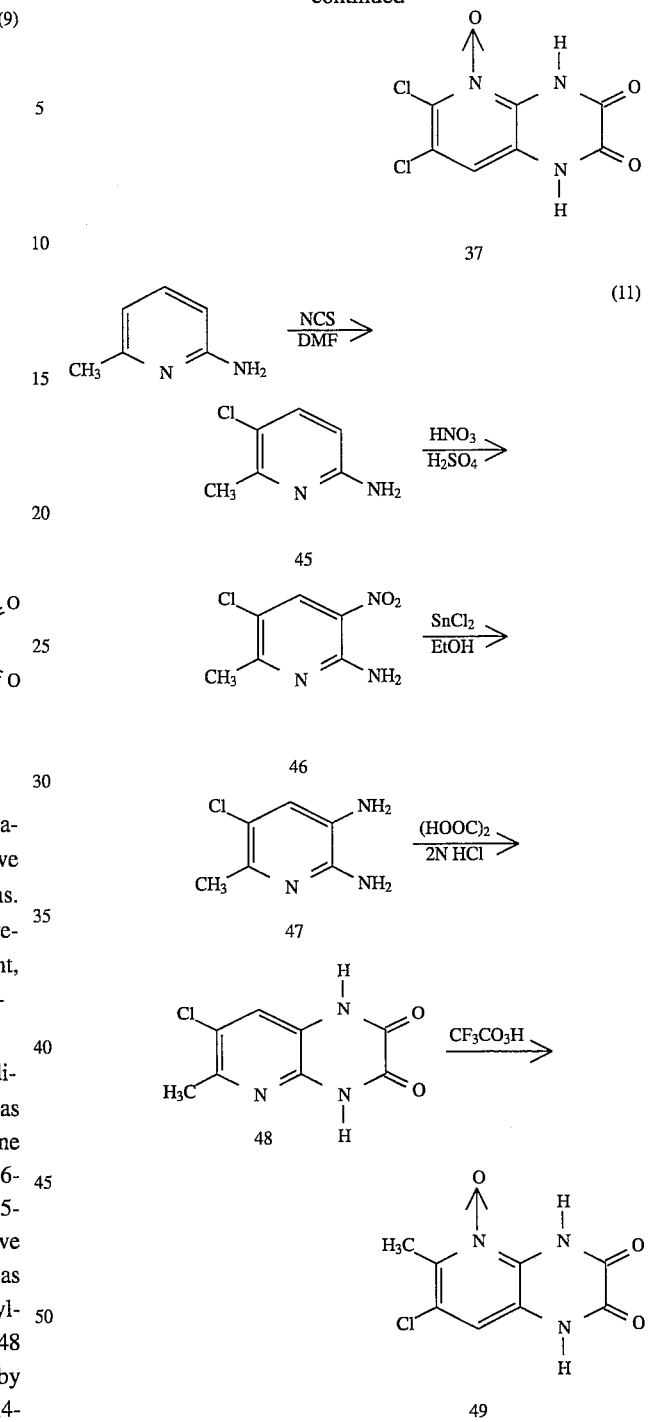

It was found that 8-aza-6,7-dichloro-1,4-dihydroquinoxaline-2,3-dione (36) could not be oxidized by mCPBA to give the corresponding 8-N-oxide QX under similar conditions. However, by using trifluoroperacetic acid ($CF_3CO_3H$, prepared from $H_2O_2$ and $(CF_3CO)_2O$) as the oxidation agent, 6,7-dichloro-8-(N-oxy)aza-1,4-dihydroquinoxaline-2,3-dione (37) was obtained in good yield (eq 10).

8-Aza-6-chloro-7-methyl-1,4-dihydroquinoxaline-2,3-dione (48) was prepared from 2-amino-6-methylpyridine as shown in eq 11. Chlorination of 2-amino-6-methylpyridine by N-chlorosuccinimide (NCS) gave 2-amino-5-chloro-6-methylpyridine (45), which was nitrated to give 2-amino-5-chloro-6-methyl-3-nitropyridine (46). Reduction of 46 gave 2,3-diamino-5-chloro-6-methylpyridine (47), which was condensed with oxalic acid to give 8-aza-6-chloro-7-methyl-1,4-dihydroquinoxaline-2,3-dione (48). Similar to 36, 48 could not be oxidized to its corresponding N-oxide by mCPBA. Therefore, 8-(N-oxy)aza-6-chloro-7-methyl-1,4-dihydroquinoxaline-2,3-dione (49) was obtained from 48 by using $CF_3CO_3H$ as the oxidation agent.

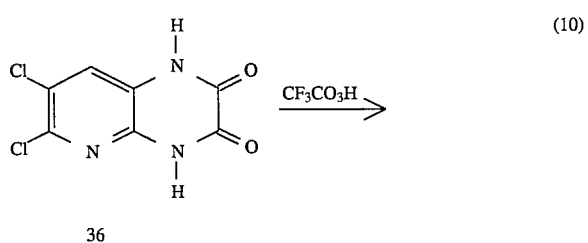

5-Aza-7-trifluoromethyl-1,4-dihydroquinoxaline-2,3-dione (52) was prepared by nitration of 2-amino-5-trifluoromethylpyridine, followed by reduction of nitropyridine 50 and cyclization of diaminopyridine 51 with diethyl oxalate. Oxidation of 52 by $CF_3CO_3H$ gave 5-(N-oxy)aza-7-trifluoromethyl-1,4-dihydroquinoxaline-2,3-dione (53) (eq 12). Similarly, oxidation of aza-QX 19 by $CF_3CO_3H$ gave 6-Cyano-5,7-dimethyl-8-(N-oxy)aza-1,4-dihydroquinoxaline-2,3-dione (54) (eq 13). Oxidation of 6,8-diaza-1,4-dihydroquinoxaline-2,3-dione (13) by $CF_3CO_3H$ gave a mono N-oxide-QX which was tentatively assigned as 8-(N-oxy)-6,8-diaza-1,4-dihydroquinoxaline-2,3-dione (55) (eq 14).

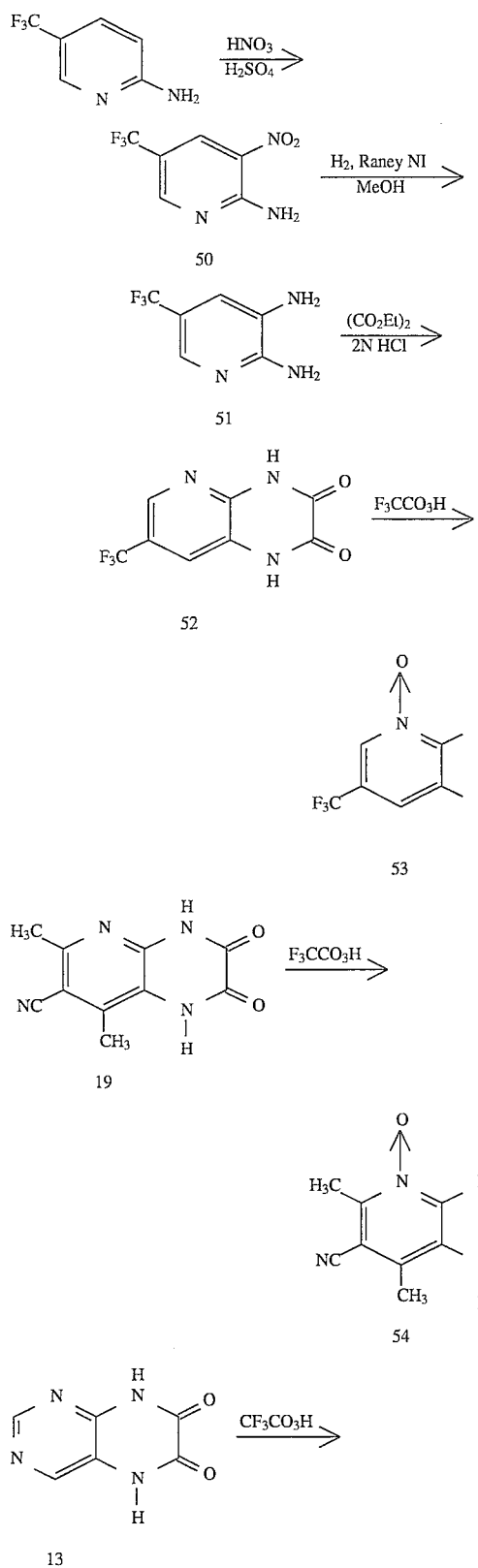

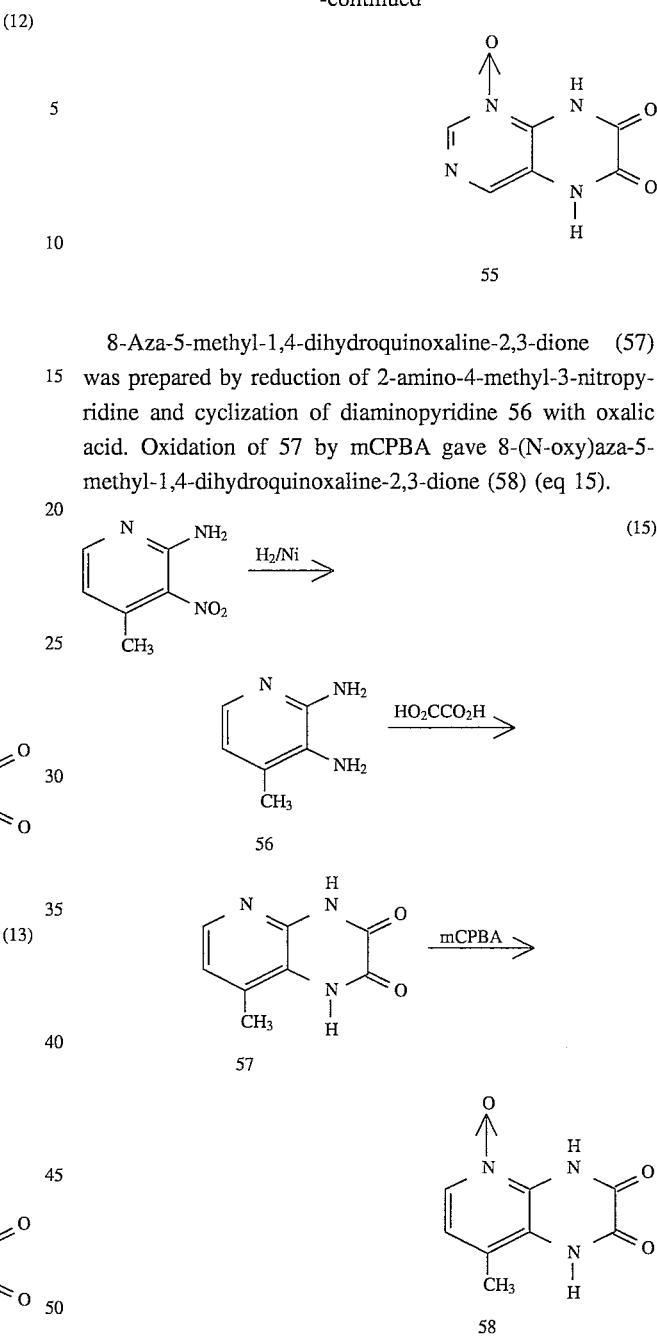

8-Aza-5-methyl-1,4-dihydroquinoxaline-2,3-dione (57) was prepared by reduction of 2-amino-4-methyl-3-nitropyridine and cyclization of diaminopyridine 56 with oxalic acid. Oxidation of 57 by mCPBA gave 8-(N-oxy)aza-5-methyl-1,4-dihydroquinoxaline-2,3-dione (58) (eq 15).

Nitration of 7-chloro-6-methyl-5-(N-oxy)aza-1,4-dihydroquinoxaline-2,3-dione (49) using fuming $HNO_3$ in TFA at 85° C. gave 7-chloro-6-methyl-8-nitro-5-(N-oxy)aza-1,4-dihydroquinoxaline-2,3-dione (59) in 70% yield. Deoxygenation of 59 was accomplished by treatment with $PCl_3$ to give 5-aza-7-chloro-6-methyl-8-nitro-1,4-dihydroquinoxaline-2,3-dione (60) (eq 16).

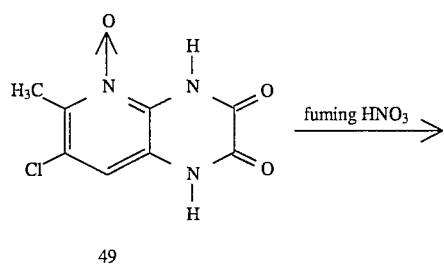

49

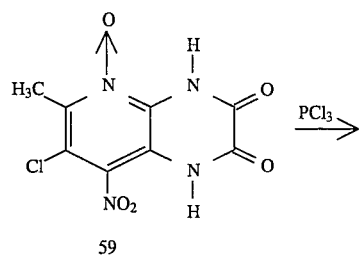

59

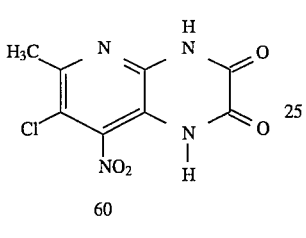

60

5-Aza-7-nitro-1,4-dihydroquinoxaline-2,3-dione (63) was prepared by nucleophilic substitution of 2-chloro-3,5-dinitropyridine with NH$_4$OH to give 2-amino-3,5-dinitropyridine (61), followed by selective reduction of 61 with (NH$_4$)$_2$S and cyclization of diaminopyridine 62 with oxalic acid. Oxidation of 63 by CF$_3$CO$_3$H gave 5-(N-oxy)aza-7-nitro-1,4-dihydroquinoxaline-2,3-dione (64) (eq 17).

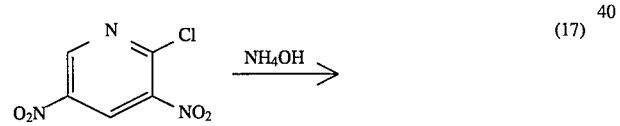

61

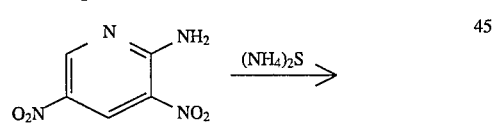

62

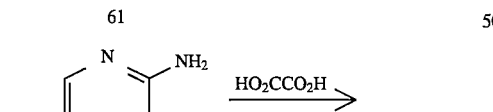

63

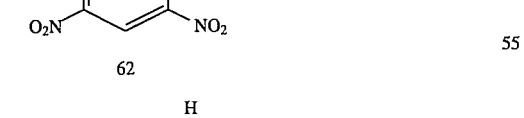

(17)

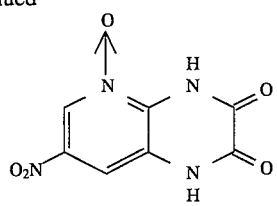

64

5-Aza-7-carbamoyl-1,4-dihydroquinoxaline-2,3-dione (67) was prepared by nitration of 6-amino-nicotinamide, followed by reduction of nitropyridine 65 and cyclization of diaminopyridine 66 with diethyl oxalate. Oxidation of 67 by CF$_3$CO$_3$H gave 5-(N-oxy)aza-7-carbamoyl-1,4-dihydroquinoxaline-2,3-dione (68) (eq 18).

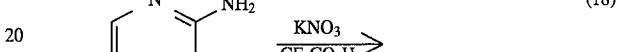

(18)

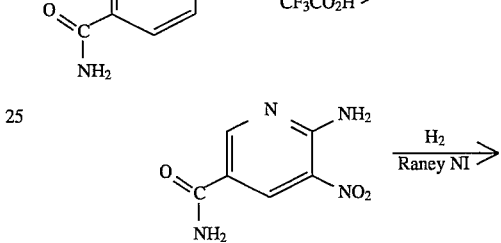

65

66

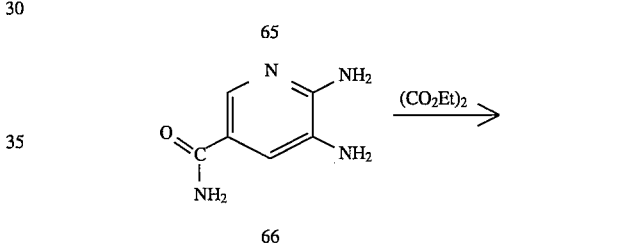

67

68

Reaction of 5-aza-7-chloro-6-nitro-1,4-dihydroquinoxaline-2,3-dione (15) with imidazole in DMF at 160° C. gave imidazole substituted-QX 69. Oxidation of 69 by CF$_3$CO$_3$H give a product which was tentatively assigned as 3-(N-oxy)-imidazole substituted-QX 70 (eq 19). Similarly, reaction of 7-chloro-5-(N-oxy)aza-QX 32 with imidazole gave the imidazole substituted N-oxide-aza-QX 71 (eq 20). Nitration of N-oxide-QX 35 by fuming HNO$_3$ gave nitro-QX 72 (eq 21).

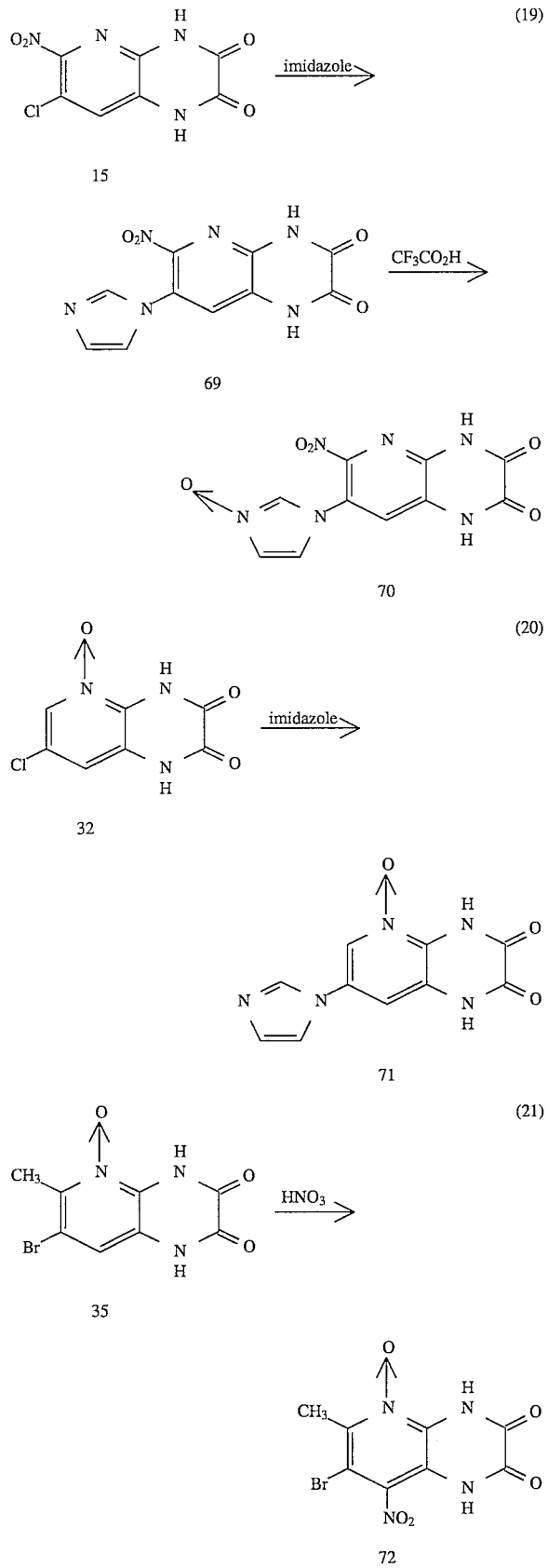

The present invention also relates to the discovery that certain 8-(N-oxy)aza-1,4-dihydroquinoxaline-2,3-diones have high affinity for the glycine/NMDA receptor and have unexpectedly high in vivo activity as an anticonvulsant in MES experiment in mice. Therefore, these compounds are able to cross the blood-brain-barrier at high levels. For instance, 6-chloro-8-(N-oxy)-aza-1,4-dihydroquinoxaline-2,3-dione, which has a $K_i$ of 600 nM, was found to have an $ED_{50}$ of 1–1.5 mg/kg as an anticonvulsant in an MES experiment in mice. In comparison, 6,7-dichloro-5-nitro-1,4-dihydroquinoxaline-2,3-dione ($K_i$=3.3 nM), has an $ED_{50}$ of 4–5 mg/kg as an anticonvulsant in an MES experiment in mice. This means that 6-chloro-8-(N-oxy)aza-1,4-dihydroquinoxaline-2,3-dione might be about 1000 times better in crossing the blood-brain-barrier than 6,7-dichloro-5-nitro-1,4-dihydroquinoxaline-2,3-dione. Other compounds that have been found to be unexpectedly active in vivo as anticonvulsants in the MES experiment in mice include 6-bromo-8-(N-oxy)aza-1,4-dihydroquinoxaline-2,3-dione ($K_i$=1000 nM, $ED_{50}$ 1–1.5 mg/kg), 6-methyl-8-(N-oxy)aza-1,4-dihydroquinoxaline-2,3-dione ($K_i$=2400 nM, $ED_{50}$= 1–1.5 mg/kg), 6,7-dichloro-8-(N-oxy)aza-1,4-dihydroquinoxaline-2,3-dione ($K_i$=100 nM, $ED_{50}$=7.5 mg/kg), and 6-chloro-7-methyl-8-(N-oxy)aza-1,4-dihydroquinoxaline-2,3-dione ($K_i$=50 nM, $ED_{50}$=7 mg/kg).

The present invention also relates to the discovery that certain 8-(N-oxy)aza-1,4-dihydroquinoxaline-2,3-diones have high affinity for both the glycine/NMDA receptor and the non-NMDA receptor and have high in vivo activity as an anticonvulsant in MES experiment in mice. Therefore these compounds are able to cross the blood-brain-barrier at high levels and are expected to possess good neuroprotective properties due to their combined NMDA and non-NMDA receptors antagonist activity. For instance, 6-nitro-8-(N-oxy)aza-1,4-dihydroquinoxaline-2,3-dione (64) has been found to have a $K_i$ of 130 nM for glycine/NMDA receptor and 340 nM for non-NMDA receptor, and an $ED_{50}$ of 3–4 mg/kg as an anticonvulsant in MES experiment in mice.

It was discovered that certain N-oxide pyridine analogs of 1,4-dihydroquinoxaline-2,3-dione are more water soluble than the corresponding 1,4-dihydroquinoxaline-2,3-dione. Therefore, it is easier to formulate the N-oxide analogs into aqueous solution for i.v. administration.

6-Chloro-8-(N-oxy)aza-1,4-dihydroquinoxaline-2,3-dione also has been found to provide significant neuroprotection in a rat model of focal ischemia. When 6-chloro-8-(N-oxy)aza-1,4-dihydroquinoxaline-2,3-dione was administered (20 mg/kg bolus followed by 14 mg/kg/h for 22 h, i.v.) immediately after MCA occlusion, it produced a 67% reduction in cortical infarct volumes. When 6-chloro-8-(N-oxy)aza-1,4-dihydroquinoxaline-2,3-dione was administered 30 min after MCA occlusion, it produced a 70% reduction in cortical infarct volumes and 35% reduction in subcortex infarct volumes.

Thus, the present invention is directed to compounds having high binding to the glycine receptor and low binding to the kainate and AMPA sites. Particular compounds of the invention may have high antagonist potency at the kainate, AMPA, and quisqualate receptors in addition to the glycine receptor. According to the present invention, those compounds having high binding to the glycine receptor exhibit a glycine binding affinity ($K_i$) of about 100 µM or less in a glycine binding assay. Preferably, the compounds of the present invention exhibit a $K_i$ of 10 µM or less. Most preferably, the compounds of the present invention exhibit a $K_i$ of 1 µM or less. The compounds exhibit high binding to the kainate and AMPA sites if they exhibit a $K_i$ of about 10 µM or less, especially, 1 µM or less in a kainate or AMPA binding assay.

The glycine antagonist potency in vitro may be determined using a 1 μM glycine-stimulated [$^3$H]-MK801 binding assay. This assay takes advantage of the fact that the binding of [$^3$H]-MK801 to the PCP receptor inside the pore of the NMDA channel is dependent on the presence of both glutamate and glycine. In the absence of glycine, but in the presence of glutamate, [$^3$H]-MK801 cannot bind effectively to the PCP receptor, because the NMDA channel remains closed and access of [$^3$H]-MK801 to the PCP receptor inside the closed channel pore is severely restricted.

The assay is conducted using rat brain membrane homogenates that are enriched in NMDA receptors. The membranes are prepared as follows. Frozen rat brains (obtained from Pel-Freez, Rogers, Ak.) are homogenized in 15 volumes (w/v) of ice cold 0.32M sucrose. The homogenate is spun at 1,000×g for ten minutes. The supernatant is collected and spun for 20 minutes at 44,000×g. The pellet is suspended in 15 volumes of water (relative to original brain weight). The homogenate is again spun at 44,000×g for twenty minutes. The pellet is resuspended in 5 volumes of water and the suspension is freeze-thawed 2 times. After the final thaw cycle, the suspension is brought to 15 volumes with water and spun at 44,000×g for twenty minutes. The pellet is resuspended in 5 volumes of ice-cold 10 mM HEPES, and is titrated to pH 7.4 with KOH containing 0.04% Triton X-100. Membranes are incubated with the Triton/HEPES buffer at 37° C. for 15 minutes. The volume is then brought to 15 with ice-cold 10 mM HEPES, pH 7.4, and spun/washed three times with spins of 44,000×g between washes. The final pellet is suspended in three volumes of 50 mM HEPES, pH 7.4 and the protein concentration is determined with a standard dye-binding protein assay (Bio-Rad, Richmond, Calif.). The suspension is stored at −80° C. until used. Only HPLC grade water is used for all buffers and suspensions/washings. The extensive washings are necessary to remove as much endogenous glycine from the membrane preparation as possible.

On the day of the assay, the previously prepared membranes are thawed and 5 mM Tris/HCl buffer, pH 7.4, is added to yield a final protein concentration of 0.156 mg/mL. For binding assays, 0.8 mL of membranes are pipetted into polypropylene tubes followed by 0.033 mL of 15.1 μM 5,7-dichlorokynurenic acid (DCK), 0.033 mL of 3.03 μM glycine in buffer (or buffer alone), 0.033 mL of 303 μM glutamate in buffer (or for controls, 0.1 mL 1 mM PCP instead of DCK/gly/glu), 0.033 mL glycine antagonist in buffer (or buffer alone) and 0.1 mL buffer containing 200,000 cpm [$^3$H]-MK801. Nonspecific binding is defined as the difference in binding that occurs in the absence or presence of PCP (final concentration: 100 μM). To determine the effect of 1 μM glycine on the binding of [$^3$H]-MK801, bound radioactivity in the presence of 10 μM glutamate alone (final concentration) is subtracted from the bound radioactivity in the presence of both 10 μM glutamate and 1 μM glycine (final concentration). A 500 nM concentration (final) of 5,7-dichlorokynurenic (DCK) acid is added to all assay tubes. This concentration of the glycine antagonist DCK "buffers" most of the residual endogenous glycine that is not removed by the extensive washing steps that are carried out during the membrane preparation procedure. The 500 nM DCK does not interfere with the stimulation of [$^3$H]-MK801 binding that is effected by the addition of 1 μM exogenous glycine.

The assays are incubated for 120 minutes at room temperature after which time the membrane-bound radioactivity is isolated from the free radioactivity by vacuum filtration through Whatman glass fiber filters that had been pretreated with 0.3% polyethyleneimine. Filtration is accomplished using a Brandel 48 well cell harvester. Filtered membranes are washed three times with 3 mL each of ice cold buffer. Filters are transferred to scintillation vials and 5 mL of scintillation cocktail is added. The vials are shaken overnight and the radioactivity is counted by liquid scintillation spectroscopy. The assays are done in triplicate and all experiments are conducted at least three times.

Inhibition dose response curves are constructed using increasing concentrations of glycine antagonists from 5 nM to 330 μM. IC$_{50}$ values are determined for compounds active in inhibiting 1 μM glycine-stimulated [$^3$H]-MK801 binding by computer-assisted plotting of the inhibition curves and interpolation. When compounds are found to inhibit glycine-stimulated [$^3$H]-MK801 binding, experiments are conducted to determine whether the inhibition of the glycine-stimulated [$^3$H]-MK801 binding is indeed mediated at the glycine binding site of the NMDA receptor. In these experiments, a fixed concentration of antagonist sufficient to produce a >95% inhibition of the 1 μM glycine-stimulated [$^3$H]-MK801 binding is incubated with the membranes without any additional glycine (above 1 μM) and in the presence of increasing concentrations of additional glycine (2 μm to 1 μM). If the inhibition of [$^3$H]-MK801 binding by the drug in the presence of 1 μM glycine is fully reversed by adding increasing concentrations of glycine, then the inhibition of [$^3$H]-MK801 binding is mediated by the drug acting as an antagonist at the glycine binding site of the NMDA receptor.

After constructing inhibition dose response curves and determination of glycine reversibility, $K_i$ values for the glycine antagonists are calculated using the Cheng and Prusoff equation employing the experimentally determined IC$_{50}$ values, the known concentration of glycine in the assay (1 μM) and the known affinity of glycine for the glycine binding site of the NMDA receptor (100 nM).

The same rat brain membrane homogenates used for the 1 μM glycinestimulated [$^3$H]-MK801 binding assay are used for the [$^3$H]-AMPA radioligand binding assay. On the day of the assay the frozen membranes (prepared as described above) are thawed and diluted with 30 mM Tris/HCl buffer containing 2.5 mM CaCl$_2$ and 100 mM KSCN, pH 7.4, to yield a final membrane concentration of 1.25 mg/mL membrane protein. For the binding assay, 0.8 mL of membrane homogenate is added to polypropylene tubes followed by 0.033 mL drug and 0.067 mL buffer (or for controls by 0.1 mL buffer alone) and 0.1 mL buffer containing 200,000 cpm of [$^3$H]-AMPA. The assay is incubated for 30 minutes on ice. Bound radioactivity is separated from free radioactivity by filtration over Whatman glass fiber filters (pretreated with 0.3% polyethyleneimine) using a Brandel 48 well cell harvester.

Filtered membranes are washed three times with 3 mL each of ice cold buffer. The filters are transferred to scintillation vials and 5 mL of scintillation cocktail is added. The vials are shaken overnight and radioactivity is counted by liquid scintillation spectroscopy. Nonspecific binding is determined by the radioactivity that remains bound to the membranes in the presence 10 mM glutamate. Inhibition dose response curves are constructed by adding increasing concentrations of drug from 10 nM to 100 μM.

The same membrane preparation as that used for the [$^3$H]-AMPA binding assay may be used for the [$^3$H]-Kainate radioligand binding assay. On the day of the assay the frozen rat brain membranes are thawed and 5 mM Tris/HCl buffer, pH 7.4, is added to yield a final concentration of 0.5 mg/mL membrane protein. For the binding assay, 0.8 mL of membrane homogenate is added to polypropylene tubes followed by 0.033 mL drug and 0.067 mL buffer (or for controls by 0.1 mL buffer alone) and 0.1 mL buffer containing 200,000 cpm of [$^3$H]-kainate. The assay is incubated for 2 hours on ice. Bound radioactivity is separated from free radioactivity by filtration over Whatman glass fiber filters (pretreated with 0.3% polyethyleneimine) using a Brandel 48 well cell harvester. Filtered membranes are washed three times with 3 mL each of ice cold buffer. The filters are transferred to scintillation vials and 5 mL of scintillation cocktail is added. The vials are shaken overnight and radioactivity is counted by liquid scintillation spectroscopy. Nonspecific binding is determined by the radioactivity that remains bound to the membranes in the presence 10 mM glutamate. Inhibition dose response curves are constructed by adding increasing concentrations of drug from 250 nM to 330 μM.

The binding affinities at NMDA receptor glycine sites also were estimated by electrophysiological assay either using cloned rat NMDA receptors expressed in Xenopus oocytes, or non-NMDA receptors expressed in oocytes by whole rat brain poly(A)$^+$ RNA. See U.S. application Ser. No. 08/148,259, filed Nov. 5, 1993. $K_b$ values were estimated by assuming competitive inhibition and assaying suppression of membrane current responses elicited by fixed concentrations of agonist: 1 mM glycine and 100 mM glutamate for NMDA receptors; 20 mM kainic acid for non-NMDA receptors. For NMDA receptors KbS were approximated by averaging values at three subtype combinations (NR1A/NR2A, NR1A/NR2B, and NR1A/NR2C).

The anxiolytic activity of any particular compound of the present invention can be determined by use of any of the recognized animal models for anxiety. A preferred model is described by Jones, B. J., et al., Br. J. Pharmacol. 93:985–993 (1988). This model involves administering the compound in question to mice that have a high basal level of anxiety. The test is based on the finding that such mice find it aversive when taken from a dark home environment in a dark testing room and placed in an area painted white and brightly lit. The test box has two compartments, one white and brightly illuminated and one black and non-illuminated. The mouse has access to both compartments via an opening at floor level in the divider between the two compartments. The mice are placed in the center of the brightly illuminated area. After locating the opening to the dark area, the mice are free to pass back and forth between the two compartments. Control mice tend to spend a larger proportion of time in the dark compartment. When given an anxiolytic agent, the mice spend more time exploring the more novel brightly lit compartment and exhibit a delayed latency to move to the dark compartment. Moreover, the mice treated with the anxiolytic agent exhibit more behavior in the white compartment, as measured by exploratory rearings and line crossings. Since the mice can habituate to the test situation, naive mice should always be used in the test. Five parameters can be measured: the latency to entry into the dark compartment, the time spent in each area, the number of transitions between compartments, the number of lines crossed in each compartment, and the number of rears in each compartment. The administration of the compounds of the present invention is expected to result in the mice spending more time in the larger, brightly lit area of the test chamber.

In the light/dark exploration model, the anxiolytic activity of a putative agent can be identified by the increase of the numbers of line crossings and rears in the light compartment at the expense of the numbers of line crossings and rears in the dark compartment, in comparison with control mice.

A second preferred animal model is the rat social interaction test described by Jones, B. J. et al., supra, wherein the time that two mice spend in social interaction is quantified. The anxiolytic activity of a putative agent can be identified by the increase in the time that pairs of male rats spend in active social interaction (90% of the behaviors are investigatory in nature). Both the familiarity and the light level of the test arena can be manipulated. Undrugged rats show the highest level of social interaction when the test arena is familiar and is lit by low light. Social interaction declines if the arena is unfamiliar to the rats or is lit by bright light. Anxiolytic agents prevent this decline. The overall level of motor activity may also be measured to allow detection of drug effects specific to social behaviors.

The efficacy of the glycine and excitatory amino acid antagonists to inhibit glutamate neurotoxicity in a rat brain cortex neuron cell culture system can be determined as follows. An excitotoxicity model modified after that developed by Choi (Choi, D. W., J. Neuroscience 7:357 (1987)) can be used to test anti-excitotoxic efficacy of the glycine and excitatory amino acid antagonists. Fetuses from rat embryonic day 19 are removed from time-mated pregnant rats. The brains are removed from the fetuses and the cerebral cortex is dissected. Cells from the dissected cortex are dissociated by a combination of mechanical agitation and enzymatic digestion according to the method of Landon and Robbins (Methods in Enzymology 124:412 (1986)). The dissociated cells are passed through an 80 micron nitex screen and the viability of the cells are assessed by Trypan Blue. The cells are plated on poly-D-lysine coated plates and incubated at 37° C. in an atmosphere containing 91% $O_2$/9% $CO_2$. Six days later, fluoro-d-uracil is added for two days to suppress non-neural cell growth. At culture day 12, the primary neuron cultures are exposed to 100 μM glutamate for 5 minutes with or without increasing doses of glycine and excitatory amino acid antagonist or other drugs. After 5 minutes, the cultures are washed and incubated for 24 hours at 37° C. Neuronal cell damage is quantitated by measuring the lactate dehydrogenase (LDH) activity that is released into the culture medium. The LDH activity is measured according to the method of Decker et al. (Decker et al., J. Immunol. Methods 15:16 (1988)).

The anticonvulsant activity of the glycine and excitatory amino acid antagonists can be assessed in the audiogenic seizure model in DBA-2 mice as follows. DBA-2 mice can be obtained from Jackson Laboratories, Bar Harbor, Me. These mice at an age of (27 days develop a tonic seizure within 5–10 seconds and die when they are exposed to a sound of 14 kHz (sinus wave) at 110 dB (Lonsdale, D., Dev. Pharmacol. Ther. 4:28 (1982)). Seizure protection is defined when animals injected with drug 30 minutes prior to sound exposure do not develop a seizure and do not die during a 1 minute exposure to the sound. 21 day old DBA-2 mice are used for all experiments. Compounds are given intraperitoneally in either saline, DMSO, or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant efficacy of the glycine receptor antagonists can be assessed in the pentylenetetrazol (PTZ)-induced seizure test as follows. Swiss/Webster mice, when injected with 50 mg/kg PTZ (i.p.) develop a minimal clonic seizure of approximately 5 seconds in length within 5–15 minutes after drug injection. Anticonvulsant efficacy of a glycine/excitatory amino acid antagonist (or other) drug is defined as the absence of a seizure when a drug is given 30 minutes prior to PTZ application and a seizure does not develop for up to 45 minutes following PTZ administration. Glycine/excitatory amino acid antagonist or other drugs are given intraperitoneally in either saline, DMSO, or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The efficacy of glycine/excitatory amino acid antagonists to protect mice from NMDA-induced death may be assessed as follows. When mice are injected with 200 mg/kg N-methyl-D-aspartate (NMDA) i.p., the animals will develop seizures followed by death within 5–10 minutes. Glycine/excitatory amino acid antagonists are tested for their ability to prevent NMDA-induced death by giving the drugs i.p. 30 minutes prior to the NMDA application. Glycine/excitatory amino acid antagonist or other drugs are given intraperitoneally in either saline, DMSO, or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant activity of the glycine antagonists may be assessed in the maximum electroshock-induced seizure (MES) assay in mice. Electroshock was applied to male Swiss/Webster mice (20–30 g, Simonsen) through corneal electrodes (Swinyard, E. A., in Anticonvulsant Drugs, Mercier, J., ed., Pergamon Press, Oxford (1973), pp. 47–65). The seizure stimulus parameters were: 50 mA, 60 Hz, rectangular pulse, width 0.8 msec, duration 200 msec. Tonic hind limb extension observed after application of the electrical stimulus was recorded as occurrence of seizure. The drug was applied i.v. as an aqueous basic solution.

A series of different evaluations can be conducted on doses of the glycine/excitatory amino acid antagonists of the invention to determine the biological activity of the compounds both in normal gerbils and in animals exposed to 5 minutes of bilateral carotid occlusion. See Scheme I.

Scheme I

Gerbil Ischemia Model

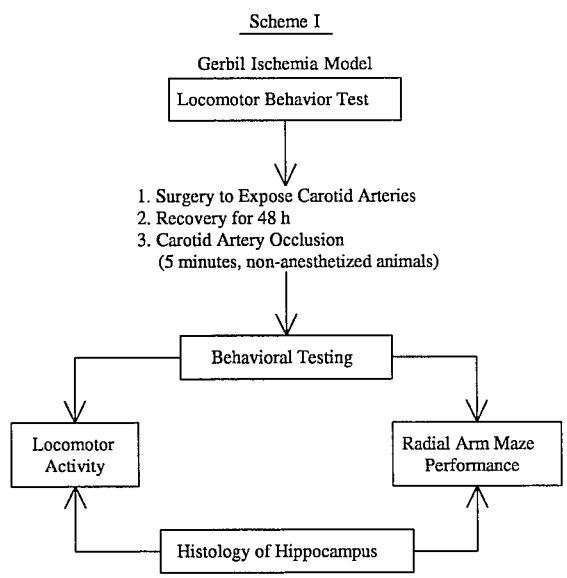

These studies are conducted in animals who are conscious and have no other pharmacological agents administered to them. Gerbils are preinstrumented 48-hours prior to ischemia to allow for the complete elimination of the pentobarbital anesthetic that is employed. When tested with drugs, animals are given i.p. injections of the glycine/excitatory amino acid antagonist or vehicle. In the case of multiple injections, animals are given i.p. injections 2 hours apart and the final injection is given 30 minutes prior to the ischemic period, or, in the case of post treatment, the animals are given injections at 30 minutes, 2 hours, 4 hours, and 6 hours post-ischemic reperfusion.

In order to assess the direct pharmacological activity or potential activity of the glycine/excitatory amino acid antagonists, naive gerbils are injected with either saline or differing doses of the antagonist. The behavioral changes are assessed using a photobeam locomotor activity chamber, which is a two foot circular diameter arena with photobeam detection. Animals are individually placed in the 2 foot diameter chambers. The chambers are housed in a closed cabinet and noise is abated using both a background white noise generator and a fan. Animals are placed in these chambers in the case of the initial pharmacological evaluation for a period of 6 hours and the total activity during each successive hour is accumulated using computer control systems.

Saline results in an initial high rate of activity, with the control animals showing a first hour activity level of about 1600 counts. This level of control activity is typical for the gerbil under these experimental conditions. As the session progresses, animals decrease their exploratory activity and at the terminal period the activity declines to about 250 counts per hour. It is expected that the glycine/excitatory amino acid antagonists of the present invention will have no significant effect on either the initial exploratory rate or the terminal rate of exploration.

In a next phase of the evaluation of the glycine/excitatory amino acid antagonists, gerbils are pretreated with varying doses of the antagonists and then exposed to a five minute period of bilateral carotid occlusion. Following the initiation of reperfusion, animals are placed into the circular locomotor activity testing apparatus and the activity at the beginning of the first hour following reperfusion is monitored for the subsequent four hours.

Control animals not exposed to ischemia and given injections of saline prior to being placed in the locomotor activity chamber show a characteristic pattern of activity that, in the first hour of locomotor activity, is substantially higher than during all other hours and progressively declines over four hours to a very low value. In contrast to the progressive decline in activity over the four hour testing period, control animals that are exposed to five minutes of cortical ischemia demonstrate a completely different pattern of locomotor activity. During the first hour, there is a significant decline in activity, followed by a progressive increase in which the activity during the fourth hour is ten-fold higher than that demonstrated by animals not exposed to carotid occlusion. These results are typical and are a reliable result of the alterations caused by five minutes of bilateral carotid occlusion in the gerbil.

Separate groups of gerbils are pretreated with the glycine/excitatory amino acid antagonists of the invention 30 minutes before the onset of carotid occlusion and then placed into the locomotor activity following one hour of reperfusion. It is expected that pretreatment of the gerbils with the glycine/excitatory amino acid antagonists of the invention will prevent both the post-ischemic decrease and increase in activity. Post-ischemic decreases in activity are expected to be near zero during the first hour following reperfusion.

Pretreatment with the glycine/excitatory amino acid antagonists of the invention is expected to reduce or prevent this early depression of behavior. In addition, the glycine/excitatory amino acid antagonists of the invention are expected to prevent the post-ischemic stimulation of behavior.

Subsequent to completion of the single dose pretreatment evaluations, gerbils are also evaluated with multiple injections of the glycine/excitatory amino acid antagonists of the invention. Doses are administered i.p. at 6 hours, 4 hours, 2 hours, and 30 minutes prior to the onset of 5 minutes of ischemia.

At 24 hours, all animals are evaluated for differences in patrolling behavior using a 8-arm radial maze. In this procedure, animals are placed into the center start chamber of the maze, the barrier removed and the amount of time and the number of times the animal makes an error recorded prior to completion of exploration in all 8 arms of the maze. An error is defined as the revisiting of an arm by an animal entering to the extent of the entire body without including its tail. If the animal perseveres or fails to leave the arm for longer than five minutes, the session is terminated. In the control population of the animals, the number of errors and exploration of the maze with no prior experience (naive) is approximately 6 errors. This is an average value for an N of 28 gerbils. Following 5 minutes of bilateral carotid occlusion and testing at 24 hours, gerbils make an average number of errors of 21. When animals are pretreated with the glycine/excitatory amino acid antagonists of the invention, there is expected to be a significant reduction in the number of errors made. There is also expected to be a significant sparing of the behavioral changes that are induced in the radial arm maze performance.

It is also expected that post treatment with the glycine/excitatory amino acid antagonists of the invention will reduce the short term memory impairment 24 hours post ischemic/reperfusion.

The effects of 5 minutes of bilateral carotid occlusion on neuronal cell death in the dorsal hippocampus may be evaluated in animals 7 days after ischemia reperfusion injury. Previous studies have demonstrated that neuronal degeneration begins to occur around 3 days following cerebral ischemia. By 7 days, those neurons that have been affected will undergo cytolysis and have either completed degeneration or are readily apparent as dark nuclei and displaced nuclei or as cells with eosinophilic cytoplasm and pycnotic nuclei. The lesion with 5 minutes of ischemia is essentially restricted within the hippocampus to the CA1 region of the dorsal hippocampus. The intermedial lateral zone of the horn is unaffected and the dentate gyrus and/or cells in CA3 do not show pathology. Gerbils are anesthetized on day 7 following ischemia with 60 mg/kg of pentobarbital. Brains are perfused transcardiac with ice-cold saline followed by buffered paraformaldehyde (10% ). Brains are removed, imbedded and sections made. Sections are stained with hematoxylineosin and neuronal cell counts are determined in terms of number of neuronal nuclei/100 micrometers. Normal control animals (not exposed to ischemia reperfusion injury) will not demonstrate any significant change in normal density nuclei within this region. Exposure to five minutes of bilateral carotid occlusion results in a significant reduction in the number of nuclei present in the CA1 region. In general, this lesion results in a patchy necrosis instead of a confluent necrosis which is seen if 10 minutes of ischemia is employed. Pretreatment with the glycine receptor antagonists of the invention are expected to produce a significant protection of hippocampal neuronal degeneration.

It is known that NMDA receptors are critically involved in the development of persistent pain following nerve and tissue injury. Tissue injury, such as, that caused by injecting a small amount of formalin subcutaneously into the hindpaw of a test animal, has been shown to produce an immediate increase of glutamate and aspartate in the spinal cord (Skilling, S. R., et al., J. Neurosci. 10:1309–1318 (1990)). Administration of NMDA receptor blockers reduces the response of spinal cord dorsal horn neurons following formalin injection (Dickenson and Aydar, Neurosci. Lett. 121:263–266 (1991); Haley, J. E., et al., Brain Res. 518:218–226 (1990)). These dorsal horn neurons are critical in carrying the pain signal from the spinal cord to the brain and a reduced response of these neurons is indicative of a reduction in pain perceived by the test animal to which pain has been inflicted by subcutaneous formalin injection.

Because of the observation that NMDA receptor antagonists can block dorsal horn neuron response induced by subcutaneous formalin injection, NMDA receptor antagonists have potential for the treatment of chronic pain, such as, pain caused by surgery or by amputation (phantom pain) or by infliction of other wounds (wound pain). However, the use of conventional NMDA antagonists, such as, MK801 or CGS 19755, in preventing or treating chronic pain is severely limited by the adverse PCP-like behavioral side effects that are caused by these drugs. It is expected that the glycine receptor antagonists that are the subject of this invention will be highly effective in preventing chronic pain in mice induced by injecting formalin subcutaneously into the hindpaw of the animals. Because the glycine/excitatory amino acid antagonists of this invention are expected to be free of PCP-like side effects, these drugs are highly useful in preventing or treating chronic pain without causing PCP-like adverse behavioral side effects.

The effects of the glycine receptor antagonists of the present invention on chronic pain can be evaluated as follows. Male Swiss/Webster mice weighing 25–35 grams are housed five to a cage with free access to food and water and are maintained on a 12 hour light cycle (light onset at 0800 h). The glycine receptor antagonist is dissolved in DMSO at a concentration of 1–40 and 5–40 mg/mL, respectively. DMSO is used as vehicle control. All drugs are injected intraperitoneally (1 µl/g). The formalin test is performed as described (Dubuisson and Dennis, Pain 4:H161–174 (1977)). Mice are observed in a plexiglass cylinder, 25 cm in diameter and 30 cm in height. The plantar surface of one hindpaw is injected subcutaneously with 20 µl of 5% formalin. The degree of pain is determined by measuring the amount of time the animal spends licking the formalin-injected paw during the following time intervals: 0–5'(early phase); 5'–10', 10'–15', and 15'–50' (late phase). To test whether the glycine/excitatory amino acid antagonists prevent chronic pain in the test animals, vehicle (DMSO) or drugs dissolved in vehicle at doses of 1 mg/kg to 40 mg/kg are injected intraperitoneally 30 minutes prior to the formalin injection. For each dose of drug or vehicle control, at least six animals are used.

Compared to vehicle control, it is expected that the intraperitoneal injection of the glycine receptor antagonists 30 minutes prior to formalin injection into the hindpaw will significantly inhibit formalin-induced chronic pain in a dose-dependent manner as determined by the reduction of the time spent licking by the mouse of the formalin injected hindpaw caused by increasing doses of glycine/excitatory amino acid antagonist.

Compositions within the scope of this invention include all compositions wherein the compounds of the present invention are contained in an amount that is effective to achieve its intended purpose. While individual needs vary, determination of optimal ranges of effective amounts of each component is with the skill of the art. Typically, the compounds may be administered to mammals, e.g., humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder, and post traumatic stress disorders. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, as well as for the treatment of Alzheimer's disease, amyotrophic lateral sclerosis, Huntington's disease, and Down's Syndrome, or in a method of treating a disease in which the pathophysiology of the disorder involves hyperactivity of the excitatory amino acids or NMDA receptor-ion channel related neurotoxicity or psychosis, the pharmaceutical compositions of the invention can comprise the compounds of the present invention at a unit dose level of about 0.01 to about 50 mg/kg of body weight, or an equivalent amount of the pharmaceutically acceptable salt thereof, on a regimen of 1–4 times per day. When used to treat chronic pain or to induce anesthesia, the compounds of the invention can be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose can comprise from about 0.01 to about 50 mg, preferably about 0.1 to about 10 mg of the compound. The unit dose can be administered one or more times daily as one or more tablets each containing from about 0.1 to about 10, conveniently about 0.25 to 50, mg of the compound or its solvates.

In addition to administering the compound as a raw chemical, the compounds of the invention can be administered as part of a pharmaceutical preparation containing suitable pharmaceutically acceptable carriers comprising excipients and auxiliaries that facilitate processing of the compounds into preparations that can be used pharmaceutically. Preferably, the preparations, particularly those preparations that can be administered orally and that can be used for the preferred type of administration, such as, tablets, dragees, and capsules, and preparations that can be administered rectally, such as, suppositories, as well as suitable solutions for administration by injection or orally, contain from about 0.01 to 99 percent, preferably from about 0.25 to 75 percent, of active compound(s), together with the excipient.

Also included within the scope of the present invention are the nontoxic pharmaceutically acceptable salts of the compounds of the present invention. Basic salts are formed by mixing a solution of the particular compound of the present invention with a solution of a pharmaceutically acceptable non-toxic base, such as, sodium hydroxide, potassium hydroxide, choline hydroxide, sodium bicarbonate, sodium carbonate, Tris, and the like.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

When the compositions of the invention are administered ocularly, one may achieve either local or systemic administration. For example, the compositions of the present invention can be administered in the form of eye drops that are substantially isotonic with tear fluid to achieve systemic administration. Preferably, such compositions will also comprise a permeation-enhancing agent, which aids the systemic absorption of the compounds of the present invention. See, U.S. Pat. No. 5,182,258. Alternatively, the compositions of the invention can be administered ocularly to treat or prevent optic nerve degeneration. In this embodiment, the compounds of the present invention are administered in the form of eye drops, as disclosed above, or can be injected into the vicinity of the optic nerve. In the alternative, thin ocular implants can be employed, which slowly release the compounds of the present invention.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically. Preferably, the preparations, particularly those preparations that can be administered orally and that can be used for the preferred type of administration, such as, tablets, dragees, and capsules, and also preparations which can be administered rectally, such as, suppositories, as well as suitable solutions for administration by injection or orally, are present at a concentration of from about 0.01 to 99 percent, together with the excipient.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Possible pharmaceutical preparations that can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules, which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. Especially preferred alkaline salts are ammonium salts prepared, for example, with tris, choline hydroxide, bis-tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The characterization of glycine binding sites in vitro has been difficult because of the lack of selective drug ligands. Thus, the glycine ligands of the present invention can be used to characterize the glycine binding site. Particularly preferred substituted and unsubstituted compounds that can be used for this purpose are isotopically or radiolabelled derivatives, e.g., where one or more of the atoms are replaced with $^2$H, $^3$H, $^{11}$C, $^{14}$C, $^{15}$N, or $^{18}$F.

The following examples are illustrative, but not limiting, of the method and compositions of the present invention. Other suitable modifications and adaptations of the variety of conditions and parameters normally encountered in clinical therapy and obvious to those skilled in the art are within the spirit and scope of the invention.

EXAMPLES

Example 1

Preparation of 6-Chloro-8-aza-1,4-dihydroquinoxaline-2,3-dione (5)

Procedure A for the Preparation of 6-Chloro-8-aza-1,4-dihydroquinoxaline2,3-dione (5)
2-Amino-5-chloro-3-nitropyridine (2)

To 100 mL of $H_2SO_4$ (97%) kept in an ice-bath was added portionwise 25.7 g (0.200 mol) of 2-amino-5-chloropyridine (1). The resulting solution was heated to 55° C. and 13.5 mL (0.211 mol) of $HNO_3$ (d=1.41, 69–70%) was added dropwise to keep the temperature at 55°–60° C. (takes about 2 h). The solution was heated at 55°–60° C. for 1 h after addition of $HNO_3$. It was poured into 600 mL of ice-water and partially neutralized with 40% NaOH (about 200 mL). The yellow precipitate was filtered, washed with water, and dried to leave a yellow solid 19.5 g (56%). $^1$H NMR (CDCl$_3$), 6.70 (mb, 2), 8.331 (d, 1), 8.429 (d, 1).
2,3-Diamino-5-chloropyridine (3) and 2,3-diamino-5,6-dichloropyridine (4)

To 100 mL of concentrated HCl (37%) in an ice-bath was added 38.4 g (0.200 mol) of SnCl$_2$ portionwise. To the solution was added portionwise 8.7 g (0.050 mol) of 2-amino-5-chloro-3-nitropyridine (2); heat releasing was observed during the addition. The mixture was heated to reflux and the resulting solution was refluxed for 30 min. The solution was cooled to room temperature, and basified by 40% NaOH to pH=12. The mixture was heated at 90°–100° C. for 2 h and cooled to room temperature. It was filtered and washed with ice water. The solid was boiled with 200 mL of water and filtered. Solid precipitate was observed when the filtrate was cooled to room temperature. It was filtered, washed with ice-water, and dried to leave 0.82 g of solid. The mother solid was boiled with 200 mL of water and filtered. A white precipitate was observed when the filtrate was cooled to room temperature. It was filtered, washed with water, and dried to leave a white solid (2.34 g). $^1$H NMR (CDCl$_3$) of the two fractions are identical. (3): 3.38 (mb, 2), 4.16 (mb, 2), 6.887 (d, 1), 7.606 (d, 1); (4): 3.38 (mb, 2), 4.33 (mb, 2), 6.979 (s, 1). (3):(4) =4:1. A portion (100 mg) of the sample was separated by preparative TLC (20×20 cm), developed by CHCl$_3$: CH$_3$OH=4:1. Two bands were observed under UV light. The bands were treated with CHCl$_3$: CH$_3$OH=3:1, filtered and evaporated. R$_f$=0.8, white solid , 15 mg (4). $^1$H NMR (CDCl$_3$), 3.334 (sb, 2), 4.316 (sb, 2), 6.982 (s, 1). R$_f$=0.7, white solid 48 mg (3). $^1$H NMR (CDCl$_3$), 3.379 (sb, 2), 4.185 (sb, 2), 6.887 (s, 1), 7.608 (s, 1).
6-Chloro-8-aza-1,4-dihydroquinoxaline-2,3-dione (5)

A solution of 42 mg (0.28 mmol) of 2,3-diamino-5-chloropyridine (3) and 30 mg (0.33 mmol) of oxalic acid in 2 mL of 2N HCl was refluxed for 2 h and cooled to room temperature. The mixture was filtered, washed with water, and dried to leave a brown solid (13 mg, 23%), mp >250° C. $^1$H NMR (DMSO-d$_6$), 7.432 (d, 1, J=2.1), 8.095 (d, 1, J=2.1), 12.024 (s, 1), 12.464 (s, 1). MS, 197 (M$^+$, 100), 169 (70), 141 (50), 106 (70). HRMS calcd for C$_7$H$_4$$^{35}$ClN$_3$O$_2$, 196.9988, found 196.9993.
Procedure B for the Preparation of 6-Chloro-8-aza-1,4-dihydroquinoxaline-2,3-dione (5)
2-Amino-5-chloro-3-nitropyridine (2)

To 150 mL of conc. $H_2SO_4$ was added 42.96 g (334 mmol) of 2-amino-5-chloropyridine in portions with stirring and cooling (ice-water bath). To the resulting solution was added dropwise 22.5 mL of 69–71% $HNO_3$ (355 mmol) at 50° C. (at such a rate that maintain the temperature within 50°–55° C.) over 1 h. The resulting mixture was stirred at 60° C. for 3 h, poured into ice-water (about 1,500 mL) with stirring, then basified to pH 9 by the addition of 40% aq NaOH with stirring and cooling. The precipitate was filtered, washed with water (6×50 mL), and dried to give 32.47 g (56%) of 2 as a yellow powder, mp 190°–191° C. (lit. 191°–2° C. (Israel, M. & Day, A. R., J. Org. Chem. 24:1455–1460 (1959))). $^1$H NMR (DMSO-$d_6$), 8.044–8.055 (m, 3H), 8.054 (d, 1H, J=3.9).

2,3-Diamino-5-chloropyridine (3)

A mixture of the nitropyridine 2 (22.0 g 126.8 mmol), Raney Ni (2.2 g) and MeOH (220 mL) was shaken under $H_2$ (20–40 psi) for 3 h, then filtered. The filtrate was rotaevaporated and the residual solid was dried to give 17.57 g (96%) of 3 as a tan powder, mp 169°–171° C. (lit. 172°–173° C, (Israel, M. & Day, A. R., J. Org. Chem. 24:1455–1460 (1959))). $^1$H NMR (DMSO-$d_6$), 4.991 (bs, 2H), 5.555 (bs, 2H), 6.675 (d, 1H, J=2), 7.196 (d, 1H, J=2).

6-Chloro-8-aza-1,4-dihydroquinoxaline-2,3-dione (5)

A mixture of the diamine 3 (17.566 g, 122.4 mmol), oxalic acid (13.22 g, 146.9 mmol) and 2N aq HCl (160 mL) was refluxed under $N_2$ for 16 h, then cooled to room temperature. The precipitate was filtered, washed with water (4×15 mL), and dried to give 20.26 g (84%) of 5 as a dark brown powder, mp >360° C. $^1$H NMR (DMSO-$d_6$), 7.437 (d, 1H, J=2), 8.104 (bs, 1H), 12.037 (bs, 1H), 12.477 (bs, 1H).

Example 2

Preparation of 6,7-Dichloro-8-aza-1,4-dihydroquinoxaline-2,3-dione (6)

A mixture of 15 mg (0.084 mmol) of 2,3-diamino-5,6-dichloropyridine (4) and 10 mg (0.11 mmol) of oxalic acid in 1 mL of 2N HCl was refluxed for 3 h and cooled to room temperature. The mixture was filtered, washed with water, and dried to leave a brown solid (8 mg, 41%) mp >250° C. $^1$H NMR (DMSO-$d_6$), 7.556 (s, 1), 12.100 (s, 1), 12.640 (s, 1).

Example 3

Preparation of 6-Bromo-7-methyl-8-aza-1,4-dihydroquinoxaline-2,3-dione (8)

A solution of 259 mg (1.28 mmol) of 2,3-diamino-5-bromo-6-methylpyridine (7) and 122 mg (1.35 mmol) of oxalic acid in 3 mL of 2N HCl was refluxed for 2.5 h and cooled to room temperature. The mixture was filtered, washed with water, and dried to leave a brown solid (199 mg, 70%) mp >250° C. $^1$H NMR (DMSO-$d_6$), 2.49 (s, 3), 7.550 (s, 1), 11.939 (s, 1), 12.393 (s, 1). MS, 255 (M$^+$, 100), 227 (40), 199 (20), 148 (60), 120 (40). HRMS calcd for $C_8H_6{}^{79}BrN_3O_2$, 254.9639, found 254.9643.

Example 4

Preparation of 6-Aza-1,4-dihydroquinoxaline-2,3-dione (11)

A solution of 1.64 g (15.0 mmol) of 3,4-diaminopyridine (10) and 1.45 g (16.1 mmol) of oxalic acid in 10 mL of 2N HCl was refluxed for 3 h and cooled to room temperature. The mixture was filtered, washed with water, and dried to leave a white solid (2.40 g, 98%), mp >250° C. $^1$H NMR (DMSO-$d_6$), 7.448 (d, 1, J=6.32), 8.391 (d, 1, J=6.11), 8.452 (s, 1), 12.511 (s, 1), 12.885 (sb, 1). MS, 163 (M$^+$, 60), 135 (40), 107 (20), 38 (100). HRMS calcd for $C_7H_5N_3O_2$, 163.0378, found 163.0383.

Example 5

Preparation of 6,8-Diaza-1,4-dihydroquinoxaline-2,3-dione (13)

A solution of 262 mg (2.38 mmol) of 4,5-diaminopyrimidine (12) and 226 mg (2.51 mmol) of oxalic acid in 3 mL of 2N HCl was refluxed for 5 h and cooled to room temperature. The mixture was filtered, washed with water, and dried to leave a brown solid (285 mg, 73%), mp >250° C. $^1$H NMR (DMSO-$d_6$), 8.357 (s, 1), 8.600 (s, 1), 12.062 (s, 1), 12.642 (s, 1). MS, 164 (M$^+$, 100), 136 (80), 109 (20). HRMS calcd for $C_6H_4N_4O_2$, 164.0330, found 164.0351.

Example 6

Preparation of 6-Chloro-7-nitro-8-aza-1,4-dihydroquinoxaline-2,3-dione (15)

A solution of 94 mg (0.47 mmol) of 6-chloro-8-aza-1,4-dihydroquinoxaline-2,3-dione (5) and 80 mg (0.79 mmol) of $KNO_3$ in 1 mL of concentrated $H_2SO_4$ was heated at 60° C. for 3 days. To the reaction mixture was added 65 mg of $KNO_3$ and it was heated at 60° C. for 1 day, followed by the addition of 23 mg of $KNO_3$ and heating at 60° C. for 1 day. The solution was added to 8 mL of ice-water. The mixture was filtered, washed with water, and dried to leave a yellow solid (26 mg, 22%), mp >250° C. $^1$H NMR (DMSO-$d_6$), 7.625 (s, 1), 12.411 (s, 1), 12.873 (s, 1).

Example 7

Preparation of 5,7-Dimethyl-6-cyano-8-aza-1,4-dihydroquinoxaline-2,3-dione (19) 2-Amino-4,6-dimethyl-3-nitro-5-pyridinecarbonitrile (17)

To 10 mL of $H_2SO_4$ (97%) kept in an ice-bath was added portionwise 2.45 g (16.6 mmol) of 2-amino-4,6-dimethyl-5-pyridinecarbonitrile (16) and it was stirred for 30 min. The resulting solution was heated at 55° C. and 1.2 mL (18.8 mmol) of $HNO_3$ (d=1.41, 69–70%) was added dropwise. The solution was heated at 55°–60° C. for 3 h after addition of $HNO_3$. It was cooled to room temperature and poured into 60 mL of ice-water. The yellow precipitate was filtered, washed with water, and dried to leave a yellow solid (1.76 g, 55%). $^1$H NMR (CDCl$_3$), 2.612 (s, 3), 2.716 (s, 3), 6.51 (mb, 2).

2,3-Diamino-4,6-dimethyl-5-pyridinecarbonitrile (18)

A mixture of 1.16 g (6.04 mmol) of 2-amino-3-dim-ethyl-3-nitro-5-pyridinecarbonitrile (17) and 5.72 g (30.1 mmol) of $SnCl_2$ in 15 mL of ethanol was heated at 70° C. for 1 h. The solution was evaporated and the residue was treated with 40% NaOH to pH=12. The mixture was filtered and the solid was dried to leave a yellow solid. The solid was stirred with ethyl acetate (100 mL) and the mixture was filtered. The filtrate was evaporated to leave a pale yellow solid (410 mg, 41%). $^1$H NMR (CDCl$_3$), 2,334 (s, 3), 2.522 (s, 3), 3.151 (mb, 2), 4.65 (mb, 2).

5,7-Dimethyl-6-cyano-8-aza-1,4-dihydroquinoxaline-2,3-dione (19)

A solution of 126 mg (0.777 mmol) of 2,3-diamino-4,6-dimethyl-5-pyridinecarbonitrile (18) and 77 mg (0.33 mmol) of oxalic acid in 3 mL of 2N HCl was refluxed for 9 h and cooled to room temperature. The mixture was filtered, washed with water, and dried to leave a colorless solid (72 mg, 42%), mp >250° C. $^1$H NMR (DMSO-d$_6$), 2.49 (s, 3), 2.557 (s, 3), 11.674 (s, 1), 12.622 (s, 1).

Example 8

Preparation of 6-Aza-5,7-dichloro-1,4-dihydroquinoxaline-2,3-dione (25) 4-Amino-2, 6-dichloro-3-nitropyridine (23)

To a solution of 4-amino-2,6-dichloropyridine (1.07 g, 6.56 mmol) in conc H$_2$SO$_4$ (3.5 mL) was added 0.50 mL of 70% HNO$_3$ (7.94 mmol) at room temperature. The mixture was stirred at 55° C. for 15 h, then poured into ice-H$_2$O (70 mL). To this mixture was added 40% aq. NaOH slowly to adjust the pH to 10. The precipitate was filtered, washed with water and dried to give 1.052 g (77%) of 23 as a pale yellow powder, mp 136°–8° C. $^1$H NMR (CDCl$_3$) δ6.116 (bs, 2H), 6.750 (s, 1H). It was used for the next reaction without further purification.
3,4-Diamino-2,6-dichloropyridine (24)

A mixture of 23 (709 mg, 3.41 mmol), 4.94 g (19.33 mmol) of SnCl$_2$.2 H$_2$O in 20 mL of EtOH was refluxed for 2 h. The resultant solution was rota-evaporated to remove most of the EtOH. To the residue was added H$_2$O (50 mL) and basified to pH 9 with 1N aq NaOH. The resulting white emulsion was extracted with CH$_2$Cl$_2$ (4×50 mL). The CH$_2$Cl$_2$ extract was washed with brine, dried (MgSO$_4$), and evaporated to give 570 mg (94%) of 24 as a slight pink powder, mp $_{186°-8}$° C. $^1$H NMR (CDCl$_3$) δ3.510 (bs, 2H), 4.195 (bs, 2H), 6.553 (s, 1H).
6-Aza-5,7-dichloro-1,4-dihydroquinoxaline-2,3-dione (25)

A solution of the diamine 24 (564 mg, 3.2 mmol) and oxalic acid (400 mg, 4.4 mmol) in 2N HCl (6.5 mL) was refluxed for 3 h, then allowed to cool to room temperature. The resulting precipitate was filtered and washed with water (2×5 mL). The wet product was stirred with 40 mL of 0.5N aq NaOH for 0.5 h, then filtered. The filtrate was acidified to pH 5 with 2N HCl. The precipitate was filtered, washed with H$_{20}$, and dried to give 543 mg (73%) of 25 as a yellow powder, mp 318°–20° C. $^1$H NMR (DMSO-d$_6$) δ 7.039 (s, 1H), 11.756 (bs, 1H), 12.398 (bs, 1H). HRMS, Calcd for C$_7$H$_3$Cl$_2$N$_3$O$_2$ 230.9610; Found 230.9619. Purity was 100% based on HPLC.

Example 9

Preparation of 6-Aza-5,7-dichloro-4-N-hydroxy-1,4-dihydroquinoxaline-2,3-dione (30)

2,6-Dichloro-4-(ethyl oxalamido)-3-nitropyridine (29)

To a solution of the aminopyridine 23 (312 mg, 1.50 mmol) and triethylamine (450 mg, 4.45 mmol) in anhydrous ether (30 mL) was added ethyl oxalyl chloride (410 mg, 3.3 mmol) at room temperature with stirring. After this addition, the mixture was stirred at room temperature for 3 h, then 20 mL of H$_2$O was added. The aqueous layer was separated and the organic layer was washed with water (10 mL), dried (MgSO$_4$) and rota-evaporated to give 463 mg (100%) of 29 as a viscous yellow oil. $^1$H NMR (CDCl$_3$) δ1.432 (t, 3H), 4.468 (q, 2H), 8.577 (s, 1H), 10.351 (s, 1H). It was used for the next reaction without further purification.
6-Aza-5,7-dichloro-4-N-hydroxy-1,4-dihydroquinoxaline-2,3-dione (30)

A mixture of 29 (412 mg, 1.34 mmol) in methanol (15 mL) with 40 mg of 5% Pd-C was hydrogenated under 15 psi of H$_2$ for 1 h, then filtered. The filtrate was rota-evaporated to dryness. The residual solid was treated with 10 mL of 1N aq NaOH and filtered. The filtrate was acidified to pH 2 with 4N HCl. The precipitate was filtered, washed with water and dried to give 80 mg (24%) of 23 as a cream powder, mp 210°–12° C. $^1$H NMR (DMSO-d$_6$) δ7.110 (s, 1H), 11.714 (bs, 1H), 12.622 (s, 1H). HRMS, Calcd for C$_7$H$_3$Cl$_2$N$_3$O$_3$ 246.9568; Found 246.9550.

Example 10

Preparation of 6-Chloro-8-(N-oxy)aza-1,4-dihydroquinoxaline-2,3-dione (32)

Procedure A for the Preparation of 6-Chloro-8-(N-oxy)aza-1,4-dihydroquinoxaline-2,3-dione (32)
6-Chloro-8-(N-oxy)aza-1,4-dihydroquinoxaline-2,3-dione (32)

To a solution of 8-aza-6-chloro-1,4-dihydroquinoxaline-2,3-dione (77 mg, 0.39 mmol) in 5 mL of TFA was added 280 mg (0.8 mmol) of mCPBA at room temperature. The resultant red solution was refluxed for 15 h, then rota-evaporated to dryness. The residual solid was washed with MeOH (3×5 mL) and dried to give 80 mg (96%) of 32 as an off-white powder, mp 321°–3° C. $^1$H NMR (DMSO-d$_6$) δ7.050 (s, 1H), 8.387 (s, 1H), 12.197 (bs, 2H). HRMS, Calcd for C$_7$H$_4$ClN$_3$O$_3$ 212.9939; found: 212.9953. Analysis, Calcd for C$_7$H$_4$ClN$_3$O$_3$+H$_2$O: C, 36.30, H, 2.61, N, 18.14; found: C, 36.16, H, 2.51, N, 17.89.
Procedure B for the Preparation of 6-Chloro-8-(N-oxy)aza-1,4-dihydroquinoxaline-2,3-dione (32)
6-Chloro-8-(N-oxy)aza-1,4-dihydroquinoxaline-2,3-dione (32)

To 30% of H$_2$O$_2$ (260 mL) was added trifluoroacetic anhydride (130 mL) at 0° C. dropwise over 1 h with stirring. After the addition, the resulting solution was stirred at 0° C. for 30 min, then the aza-QX 5 (25.68 g, 130 mmol) was added in one portion. The mixture was stirred at 90° C. for 30 min (a lot of gas evolved). The resulting orange colored solution was cooled in an ice-H$_2$O bath with stirring for 1 h. The precipitate was filtered, washed with MeOH (2×25 mL) and H$_2$O (2×25 mL), and dried to give 25.86 g (93%) of 32 as a yellowish powder, mp 344°–5° C. (dec). 1H NMR (DMSO-d$_6$), 7.050 (s, 1H), 8.387 (s, 1H), 12.197 (bs, 2H). Analysis, Calcd for (C$_7$H$_4$ClN$_3$O$_3$+H$_2$O): C 36.30, H 2.61, N 18.14; found: C 36.16, H 2.51, N 17.89. The purity was 99.6% by HPLC.

Example 11

Preparation of 6-Bromo-7-methyl-8-(N-oxy)aza-1,4-dihydroquinoxaline-2,3-dione (35)

6-Bromo-7-methyl8-(N-oxy)aza-1,4-dihydroquinoxaline-2,3-dione (35)

A mixture of 8-aza-6-bromo-7-methyl-1,4-dihydroquinoxaline-2,3-dione (664 mg, 2.59 mmol), mCPBA (900 mg, 2.8 mmol) and TFA (6.5 mL) was refluxed for 15 h, then cooled to room temperature and rota-evaporated to dryness. The residual solid was washed with MeOH (4×5 mL) and dried to give 622 mg (88%) of 35 as an off-white powder, mp 283°–5° C. (dec). $^1$H NMR (DMSO-d$_6$) δ2.537 (s, 3H), 7.214 (s, 1H), 12.098 (bs, 2H). HRMS, Calcd for C$_8$H$_6$BrN$_3$O$_3$: 270.9590; found: 270.9592.

Example 12

Preparation of 6,7-Dichloro-8(N-oxy)aza-1,4-dihydroquinoxaline-2,3-dione (37)

6,7-Dichloro-8(N-oxy)aza-1,4-dihydroquinoxaline-2,3-dione (37)

To $H_2O_2$ (30%, 1.1 mL) was added $(CF_3CO)_2O$ (3.0 mL) dropwise at 0° C. with stirring. The resulting solution was stirred at room temperature for 30 min, then 8-aza-6,7-dichloro-1,4-dihydroquinoxaline-2,3-dione (116 mg, 0.5 mmol) was added in one portion and the mixture was stirred at 90° C. under $N_2$ for 3 h. The resulting deep orange colored solution was cooled to room temperature and rota-evaporated to dryness. The thick viscous residue was co-evaporated with MeOH (3×5 mL). The resulting solid was mixed with MeOH (5 mL), stirred, filtered, washed with MeOH (2×2 mL), and dried to give 80 mg (66%) of 37 as a pale yellow powder, mp 295°–7° C. (dec). $^1H$ NMR (DMSO-$d_6$) δ7.205 (s, 1H), 12.251 (s, 1H), 12.585 (bs, 1H).

Example 13

Preparation of 8-Aza-6-methyl-1,4-dihydroquinoxaline-2,3-dione (41)

2-Amino-5-methyl-3-nitropyridine (38)

2-Amino-5-methylpyridine (2.16 g, 20.0 mmol) was added into 10 mL of conc $H_2SO_4$ in portions at room temperature with stirring. To the resulting solution was added 70% ($HNO_3$ 2.0 mL, 31.5 mmol) at room temperature dropwise with stirring. The mixture was then stirred at 55° C. (bath) for 2 h, cooled to room temperature and poured into crushed ice (about 100 g). The mixture was basified to pH 9 in ice-water bath by the addition of 40% aq. NaOH dropwise and the mixture was extracted with $CHCl_3$ (5×25 mL). The $CHCl_3$ extracts were combined, washed with brine (20 mL), dried ($MgSO_4$), and rota-evaporated to dryness to give 770 mg (25%) of 38 as a bright yellow powder, mp 175°–6° C. $^1H$ NMR ($CDCl_3$) δ2.291 (s, 3H), 6.556 (bs, 2H), 8.219 (s, 1H), 8.237 (s, 1H).

2,3-Diamino-5-methylpyridine (39)

A mixture of 38 (790 mg, 5.17 mmol), methanol (60 mL), and 5% Pd-C (70 mg) was shaken under $H_2$ (20–30 psi) for 3 h, then filtered and evaporated to give 629 mg (99%) of the diamine 39 as a black thick oil. $^1H$ NMR ($CDCl_3$) δ2.160 (s, 3H), 3.308 (bs, 2H), 4.160 (bs, 2H), 6.740 (s, 1H), 7.459 (s, 1H). It was used for the next reaction without further purification.

8-Aza-6-methyl-1,4-dihydroquinoxaline-2,3-dione (41)

A solution of 39 (625 mg, 5.08 mmol), and oxalic acid (685 mg, 7.61 mmol) in 2N aq HCl (10 mL) was refluxed for 6 h, then cooled to room temperature. The precipitate was filtered, washed with $H_2O$ (3×2 mL), and dried to give 393 mg (44%) of 41 as a black powder, mp >370° C. $^1H$ NMR (DMSO-$d_6$) δ2.260 (s, 3H), 7.248 (s, 1H), 7.903 (s, 1H), 11.950 (s, 1H), 12.243 (s, 1H).

Example 14

Preparation of 6-Methyl-8-(N-oxy)aza-1,4-dihydroquinoxaline-2,3-dione (43)

6-Methyl-8-(N-oxy)aza-1,4-dihydroquinoxaline-2,3-dione (43)

A mixture of 41 (177 mg, 1.0 mmol), mCPBA (542 mg), and TFA (5.0 mL) was stirred at 90° C. under $N_2$ for 17 h. The resulting solution was rota-evaporated to dryness. The residual solid was mixed with MeOH (3 mL), stirred, filtered, and dried to give 135 mg (74%) of the N-oxide 43 as a yellow powder, mp 228°–230° C. (dec). $^1H$ NMR (DMSO-$d_6$) δ2.224 (s, 3H), 6.851 (s, 1H), 7.993 (s, 1H), 12.117 (s, 2H). HRMS, Calcd for $C_8H_7N_3O_3$: 193.0485; found: 193.0479.

Example 15

Preparation of 8-Aza-6-bromo-1,4-dihydroquinoxaline-2,3-dione (42)

2,3-Diamino-3-bromopyridine (40)

A mixture of 2-amino-5-bromo-3-nitropyridine (676 mg, 3.10 mmol), Tin(II) chloride dihydrate (3.58 g, 14.0 mmol), and EtOH (3 mL) was heated to boiling. The resulting solution was refluxed under $N_2$ for 15 h, cooled to room temperature, and evaporated to dryness. To the residual solid was added $H_2O$ (80 mL) and basified to pH 8 with 1N aq NaOH. The resulting mixture was extracted with EtOAc (3×50 mL). The extracts were combined, washed with brine (25 mL), dried ($K_2CO_3$), and rota-evaporated to dryness. The residual solid was dried at 40° C. under vacuum, giving 565 mg (97%) of 40 as a pale yellow powder, mp 158°–160° C. $^1H$ NMR ($CDCl_3$+DMSO-$d_6$) δ3.816 (s, 2H), 4.525 (s, 2H), 6.838 (s, 1H), 7.446 (s, 1H).

8-Aza-6-bromo-1,4-dihydroquinoxaline-2,3-dione (42)

A solution of 40 (500 mg, 2.66 mmol) and oxalic acid (760 mg, 4.0 mmol) in 2N aq HCl (3.0 mL) was refluxed for 2 h, then cooled to room temperature. The precipitate was filtered, washed with $H_2O$ (2×2 mL), and dried to give 536 mg (83%) of 42 as a green-yellow powder, mp >370° C. $^1H$ NMR (DMSO-$d_6$) δ7.548 (s, 1H), 8.160 (s, 1H), 12.011 (s, 1H), 12.461 (s, 1H).

Example 16

Preparation of 6-Bromo-8-(N-oxy)aza-1,4-dihydroquinoxaline-2,3-dione (44)

6-Bromo-8-(N-oxy)aza-1,4-dihydroquinoxaline-2,3-dione (44)

A mixture of 42 (135 mg, 0.558 mmol), mCPBA (266 mg), and TFA (3.0 mL) was stirred at 90° C. under $N_2$ for 24 h. The resulting solution was rota-evaporated to dryness. The residual solid was mixed with MeOH (3 mL), stirred, filtered, washed with MeOH (3×5 mL), and dried to give 65 mg (45%) of the N-oxide 44 as a yellowish powder, mp 304°–6° C. (dec). $^1H$ NMR (DMSO-$d_6$) δ7.115 (s, 1H), 8.477 (s, 1H), 12.170 (bs, 2H). HRMS, Calcd for $C_7H_4BrN_3O_3$: 258.9414; found: 258.9428.

Example 17

Preparation of 8-Aza-6-chloro-7-methyl-1,4-dihydroquinoxaline-2,3-dione (48)

2-Amino-5-chloro-6-methylpyridine (45)

To a stirred solution of 2-amino-6-methylpyridine (10.80 g, 100.0 mmol) in dry DMF (50 mL) was added dropwise a solution of NCS (13.35 g, 100.0 mmol) in dry DMF (60 mL) at 0° C. over 20 min. The resulting brown yellow solution was stirred at 0° C. for 1 h, and at room temperature for 3 h, then poured into ice-water (about 300 mL). The resulting mixture was extracted with EtOAc (4×100 mL). The extracts were combined, washed with brine (6×50 mL), dried ($MgSO_4$), and rota-evaporated. To the residual viscous black oil was added hexane (200 mL) and it was heated to boiling with stirring. The hot hexane solution was decanted carefully, concentrated to about 60 ml, then allowed to stand at room temperature overnight. The resulting crystals were filtered and dried at room temperature in vacuo, giving 6.06 g (42%) of 45 as orange-colored long needles, mp 74°–5° C. (lit. 73°–4° C., Cress et al., J. Org. Chem. 93–6 (1976)). $^1$H NMR (CDCl$_3$) δ2.439 (s, 3H), 4.376 (bs, 2H), 6.302 (d, 1H, J=8.5), 7.340 (d, 1H, J=8.5).

2-Amino-5-chloro-6-methyl-3-nitropyridine (46)

To stirred conc H$_2$SO$_4$ (70 mL) at 0° C. was added 45 (6.0 g, 41.8 mmol) in portions. To the resulting dark brown solution was added dropwise 70% HNO$_3$ (3.5 mL, 54 mmol) at 0° C. After the addition, the reaction mixture was stirred at 50° C. under N$_2$ for 2.5 h, cooled to room temperature and poured into crushed ice (about 700 g). The mixture was basified to pH 9 by the addition of 40% aq. NaOH dropwise with stirring and cooling (ice-water bath). The precipitate was filtered, washed with water (4×100 mL) and MeOH (3×25 mL), and dried to give 5.28 g (67%) of 46 as a yellow powder, mp 214°–5° C. (lit. 214°–6° C., Cress et al., J. Org. Chem. 93–6 (1976)). $^1$H NMR (DMSO-d$_6$) δ2.445 (s, 3H), 8.011 (bs, 2H), 8.340 (s, 1H).

2,3-Diamino-5-chloro-6-methylpyridine (47)

A mixture of the nitropyridine 46 (1.48 g, 7.85 mmol), MeOH (50 mL), and 5% Pd-C (150 mg) was shaken under H$_2$ (20–30 psi) for 20 h. The mixture was filtered and the filtrate was rota-evaporated to dryness to give 1.09 g (87%) of the diamine 47 as a brown powder, mp 128°–130° C. $^1$H NMR (CDCl$_3$) δ1.661 (s, 3H), 3.233 (bs, 2H), 4.183 (bs, 2H), 6.880 (s, 1H).

8-Aza-6-chloro-7-methyl-1,4-dihydroquinoxaline-2,3-dione (48)

A solution of the diamine 47 (550 mg, 3.47 mmol) and oxalic acid (380 mg, 4.22 mmol) in 2N aq HCl (5.5 mL) was stirred at 125° C. under N$_2$ for 20 h, then cooled to room temperature, and neutralized to pH 7 with 2N aq NaOH. The precipitate was filtered, washed with water (2×5 mL), and dried to give 520 mg (71%) of 48 as a black powder, mp 362°–5° C. (dec). $^1$H NMR (DMSO-d$_6$) δ2.440 (s, 3H), 7.404 (s, 1H), 11.954 (bs, 1H), 12.370 (bs, 1H).

Example 18

Preparation of 6-Chloro-7-methyl-8-(N-oxy)aza-1,4-dihydroquinoxaline-2,3-dione (49)

6-Chloro-7-methyl-8-(N-oxy)aza-1,4-dihydroquinoxaline-2,3-dione (49)

To H$_2$O$_2$ (30%, 1.0 mL) was added (CF$_3$CO)$_2$O (3.0 mL) at 0° C. dropwise with stirring. The resulting solution was stirred at room temperature for 30 min, then 48 (106 mg, 0.5 mmol) was added in one portion and the mixture was stirred at 90° C. under N$_2$ for 2 h. The resulting deep orange colored solution was cooled to room temperature and evaporated to dryness. The thick viscous residue was co-evaporated with MeOH (3×5 mL) by rota-evaporation. The resulting solid was mixed with MeOH (5 mL), stirred, filtered, washed with MeOH (3 mL), and dried to give 25 mg (22%) of 49 as a pale yellow powder, mp 312°–5° C. (dec). $^1$H NMR (DMSO-d$_6$) δ2.491 (s, 3H), 7.092 (s, 1H), 12.121 (bs, 2H). HRMS, Calcd for C$_8$H$_6$ClN$_3$O$_3$: 227.0095; found: 227.0075.

Example 19

Preparation of 8-Aza-6-trifluoromethyl-1,4-dihydroquinoxaline-2,3-dione (52)

2-Amino-3-nitro-5-trifluoromethylpyridine (50)

To ice-water bath cooled, conc. H$_2$SO$_4$ (10 mL) was added 2-amino-5-trifluoromethylpyridine (1.70 g, 10.5 mmol). The resulting solution was heated to 50° C. and 69–71% HNO$_3$ (1.7 mL, 2.6 mmol) was added dropwise over 10 min with stirring. The resulting solution was stirred at 80° C. for 46 h, then allowed to cool to room temperature, poured into ice-water (100 mL) and basified to pH 9 with 40% aq NaOH. The resulting mixture was extracted with EtOAc (5×40 mL). The EtOAc solution was dried (MgSO$_4$), and evaporated to give 1.33 g (61%) of 50 as a yellow powder, mp 191°–3° C. $^1$H NMR (CDCl$_3$), 6.140 (bs, 1H), 7.916 (bs, 1H), 8.590 (s, 1H), 8.670 (s, 1H).

2,3-Diamino-5-trifluoromethylpyridine (51)

A mixture of 50 (950 mg, 4.59 mmol), methanol (15 mL) and Raney Ni (about 200 mg) was shaken under H$_2$ (30–40 psi) for 2 h, then filtered. The filtrate was evaporated to dryness, giving 810 mg (100%) of the diamine 51 as a deep yellow powder, mp 97°–99° C. $^1$H NMR (CDCl$_3$), 3.389 (bs, 2H), 4.556 (bs, 2H), 7.049 (s, 1H), 7.932 (s, 1H).

8-Aza-6-trifluoromethyl-1,4-dihydroquinoxaline-2,3-dione (52)

A mixture of 51 (800 mg, 4.52 mmol) and diethyl oxalate (7.0 g, 47.9 mmol) was heated at 160° C. with stirring for 2 h (the mixture turned into a solution, then more and more precipitate was formed) and cooled to room temperature. The mixture was diluted with hexane (20 mL), filtered, washed with hexane (3×5 mL), and dried to give 997 mg (94%) of 52 as a yellow powder, mp >360° C. $^1$H NMR (DMSO-d$_6$), 7.625 (s, 1H), 8.441 (s, 1H), 12.120 (s, 1H), 12.703 (s, 1H). $^{19}$F NMR (DMSO-d$_6$), −131.225 ppm (The internal standard C$_6$F$_6$: −162.9 ppm).

Example 20

Preparation of 8-(N-Oxy)aza-6-trifluoromethyl-1,4-dihydroquinoxaline-2,3-dione (53)

8-(N-oxy)aza-6-trifluoromethyl-1,4-dihydroquinoxaline-2,3-dione (53)

To 30% of H$_2$O$_2$ (4 mL) was added trifluoroacetic anhydride (2 mL) at 0° C. dropwise with stirring. After the addition, the resulting solution was stirred at 0° C. for 30 min, then the aza-QX 52 (462 mg, 2.0 mmol) was added in one portion. The mixture was stirred at 90° C. for 1 h. The resulting solution was evaporated and the residue was co-evaporated with EtOH (5×5 mL). The residual solid was mixed with EtOH (20 mL), filtered, washed with EtOH (2×5 mL), and dried to give 338 mg (68%) of 53 as an off-white powder, mp 329°–330° C. (dec). $^1$H NMR (DMSO-d$_6$), 7.204 (s, 1H), 8.656 (s, 1H), 12.310 (bs, 2H). $^{19}$F NMR (DMSO-d$_6$), −131.904 ppm (The internal standard C$_6$F$_6$: −162.9 ppm). HRMS, Calcd. for C$_8$H$_4$F$_3$N$_3$O$_3$: 247.0203; Found: 247.0204. Purity was 99.4% by HPLC.

Example 21

Preparation of 6-Cyano-5,7-dimethyl-8-(N-oxy)aza-1,4-dihydroquinoxaline-2,3-dione (54)

6-Cyano-5,7-dimethyl-8-(N-oxy)aza-1,4-dihydroquinoxaline-2,3-dione (54)

To 30% of H$_2$O$_2$ (1 mL) was added trifluoroacetic anhydride (0.5 mL) at 0° C. dropwise with stirring. After the addition, the resulting solution was stirred at 0° C. for 30 min, then compound 19 (54 mg, 0.25 mmol) was added. The mixture was heated at 90° C. with stirring for 1 h. The resulting solution was cooled to room temperature, then EtOH (10 mL) was added and stirred for 5 min. The precipitate was filtered, washed with EtOH (2×5 mL), and dried to give 35 mg (60%) of 54 as a yellowish powder, mp 325°–7° C. (dec). $^1$H NMR (DMSO-$d_6$), 2.487 (s, 3H), 2.583 (s, 3H), 11.849 (bs, 2H). HRMS, Calcd. for $C_{10}H_8N_4O_3$: 232.0594; Found: 232.0602. Purity was 99.5% by HPLC.

Example 22

Preparation of 8-(N-Oxy)-6,8-diaza-1,4-dihydroquinoxaline-2,3-dione (55)

8-(N-Oxy)-6,8-diaza-1,4-dihydroquinoxaline-2,3-dione (55)

To 30% of $H_2O_2$ (4 mL) was added trifluoroacetic anhydride (2 mL) at 0° C. dropwise with stirring. After the addition, the resulting solution was stirred at room temperature for 30 min, then the diaza-QX 13 was added. The mixture was stirred at 90° C. for 14 h. The resulting solution was cooled to room temperature, then ethanol (30 mL) was added with stirring. The resulting mixture was filtered (the solid was starting material by NMR) and the filtrate was evaporated to dryness. The residual solid was washed with EtOH (2×2 mL), and dried to give 12 mg (8%) of 55 as a yellowish powder, mp >370° C. $^1$H NMR (DMSO-$d_6$), 8.077 (s, 1H), 8.640 (s, 1H), 12.017 (s, 1H), 12.800 (s, 1H). Purity was 97.8% by HPLC. LRMS, Calcd. for $C_6H_4N_4C)_3$: 180; Found: 180.

Example 23

Preparation of 8-Aza-5-methyl-1,4-dihydroquinoxaline-2,3-dione (57)

2,3-Diamino-4-methylpyridine (56)

A mixture of 2-amino-4-methyl-3-nitropyridine (919 mg, 6.0 mmol), ethanol (20 mL) and Raney Ni (about 200 mg) was shaken under $H_2$ (30–40 psi) for 1 h, then filtered. The filtrate was evaporated to dryness, giving 740 mg (100%) of the diamine 56, mp 114°–5° C. $^1$H NMR (DMSO-$d_6$), 1.997 (s, 3H), 4.359 (s, 2H), 5.250 (s, 2H), 6.264 (d, 1H, J=3), 7.173 (d, 1H, J=3).

5-Aza-8-methyl-1,4-dihydroquinoxaline-2,3-dione (57)

A mixture of the diamine 56 (710 mg, 5.77 mmol), oxalic acid (680 mg, 7.56 mmol), and 2N HCl (6 mL) was refluxed for 2 h, then cooled to room temperature. The precipitate was filtered, washed with water (2×3 mL), and dried to give 428 mg (42%) of 57, mp >360° C. $^1$H NMR (DMSO-$d_6$), 2.351 (s, 3H), 6.986 (d, 1H), 7.938 (d, 1H), 11.437 (s, 1H), 12.271 (s, 1H).

Example 24

Preparation of 5-Methyl-8-(N-oxy)aza-1,4-dihydroquinoxaline-2,3-dione (58)

5- Methyl-8-(N-oxy)aza-1,4-dihydroquinoxaline-2,3-dione (58)

A solution of 57 (149 mg, 0.84 mmol), mCPBA (958 mg, 3.0 mmol) in TFA (8 mL) was refluxed for 40 h. The resulting solution was rota-evaporated to dryness. The resulting solid was washed with EtOH (3×5 mL), and dried to give 76 mg (47%) of the N-oxide 58 as a brown-yellow powder, mp >370° C. $^1$H NMR (DMSO-$d_6$), 2.362 (s, 3H), 6.997 (d, 1H), 8.020 (d, 1H), 11.660 (bs, 2H). Purity was 97.4% by HPLC. HRMS, Calcd. for $C_8H_7N_3O_3$: 193.0485; Found 193.0485.

Example 25

Preparation of 7-Chloro-6-methyl-8-nitro-5-(N-oxy)aza-1,4-dihydroquinoxaline-2,3-dione (59)

7-Chloro-6-methyl8-nitro-5-(N-oxy)aza-1,4-dihydroquinoxaline-2,3-dione (59)

To a solution of the N-oxide 49 (1.00 g, 4.4 mmol) in TFA (20 mL) was added fuming nitric acid (1.0 mL) at room temperature. The resulting solution was stirred at 85° C. for 60 h. The resulting mixture was cooled to room temperature, then EtOH (20 mL) was added. The precipitate was filtered, washed with EtOH (2×5 mL) and dried to give 842 mg (70%) of 59 as a yellow powder, mp 295°–7° C. $^1$H NMR (DMSO-$d_6$): 2.544 (s, 3H), 12.536 (s, 1H). The purity was 98.4% by HPLC. HRMS, Calcd. for $C_8H_5ClN_4O_5$: 271.9946; Found: 271.9945. Elemental Analysis, Calcd. for $C_8H_5ClN_4O_5$: C, 35.25, H, 1.85, N, 20.55; Found: C, 35.04, H, 1.60, N, 20.11.

Example 26

Preparation of 5-Aza-7-chloro-6-methyl-8-nitro-1,4-dihydroquinoxaline-2,3-dione (60)

5-Aza-7-chloro-6-methyl-8-nitro-1,4-dihydroquinoxaline-2,3-dione (60)

To a suspension of the nitro N-oxide 59 (272 mg, 1.0 mmol) in $CHCl_3$ (10 mL) was added $PCl_3$ (1 mL) dropwise at 0° C. The resulting mixture was refluxed for 3 h, then cooled to room temperature. The acidic mixture was neutralized to pH 7 with 1N aq NaOH and filtered. The filtrate was concentrated at 60° C. by rota-evaporation to about 1 mL, then cooled in an ice-water bath. The precipitate was filtered, washed with cooled water (3×0.5 mL) and dried to give 98 mg (38%) of 60 as a yellow powder, mp >370° C. IR (KBr), 1692, 1608, 1539 cm$^{-1}$. The purity was 95.5% by HPLC. HRMS, Calcd. for $C_8H_5ClN_4O_4$: 255.9997; Found: 255.9989.

Example 27

Preparation of 5-Aza-7-nitro-1,4-dihydroquinoxaline-2,3-dione (63)

2-Amino-3,5-dinitropyridine (61)

To a mixture of 2-chloro-3,5-dinitropyridine (2.035 g, 10 mmol) in EtOH (15 mL) was added aq. $NH_4OH$ (6 mL) dropwise at room temperature with stirring over 20 min. The resulting mixture was stirred at room temperature for 15 min, then cooled to 0° C. The precipitate was filtered, washed with water (3×5 mL) and dried to give 1.64 g (89%) of 61 as a yellow powder, mp 190°–1° C. (lit. 190°–2° C., Chemical Abstracts 63:14876 (1965)). $^1$H NMR (DMSO-$d_6$): 8.697 (bs, 1H, $D_2O$ exchange), 8.947 (d, 1H, J=2.5), 9.164 (d, 1H, J=2.5), 9.224 (bs, 1H, $D_2O$ exchange).

2,3-Diamino-5-nitropyridine (62)

To a suspension of 61 (1.617 g, 8.79 mmol) in MeOH (75 mL) was added 20% aq. $(NH_4)_2S$ (15 mL, 44 mmol) dropwise at room temperature with stirring. The resulting dark-red solution was stirred at room temperature for 0.5 h, then refluxed for 0.5 h, then cooled to room temperature. The resulting mixture was filtered. The filtrate was concentrated to about 30 mL and cooled in ice-water. The precipitate was filtered, washed with cooled EtOH (2×5 mL), and dried to give 1.092 g (80%) of 62 as a deep red powder, mp 260°–2° C.(dec) (Lit., 260° C., Chemical Abstracts 65:3826 (1966)).

¹H NMR (DMSO-d₆): 5.311 (s, 2H), 6.984 (s, 2H), 7.342(d, 1H, J=2.2), 8.171 (d, 1H, J=2.2).

5-Aza-7-nitro-1,4-dihydroquinoxaline-2,3-dione (63)

A mixture of 62 (308 mg, 2.0 mmol), oxalic acid (270 mg, 3.0 mmol) and 2N aq HCl (3 mL) was refluxed for 4 h, then cooled to 0° C. The precipitate was filtered, washed with cooled water (3×1 mL), then dried to give 308 mg (74%) of 63 as a black powder, mp >370° C. IR (KBr) 1702, 1596, 1519, 1343 cm⁻¹. ¹H NMR (DMSO-d₆): 8.086 (d, 1H, J=2.4), 8.913 (d, 1H, J=2.4), 12.224 (bs, 2H). Purity was 99.5% by HPLC. HRMS, Calcd. for $C_7H_4N_4O_4$: 208.231; Found: 208.233.

Example 28

Preparation of 7-Nitro-5-(N-oxy)aza-1,4-dihydroquinoxaline-2,3-dione (64)

7-Nitro-5-(N-oxy)aza-1,4-dihydroquinoxaline-2,3-dione (64)

To 30% of $H_2O_2$ (2 mL) was added trifluoroacetic anhydride (1 mL) at 0° C. dropwise with stirring. After the addition, the resulting solution was stirred at room temperature for 30 min, then QX 63 (104 mg, 0.5 mmol) was added. The black suspension was stirred at 90° C. for 0.5 h (the suspension turned to a yellow solution, then turned to a yellow suspension), then cooled to room temperature, and EtOH (5 mL) was added. The precipitate was filtered, washed with EtOH (2×1 mL), then dried to give 86 mg (76%) of 64 as a yellow powder, mp 325° C.(dec.). IR (KBr) 1734, 1700, 1598, 1541, 1523, 1380, 1346 cm⁴. ¹H NMR (DMSO-d₆), 7.725 (d, 1H, J=2.1), 8.948 (d, 1H, J=2.1), 12.383 (bs, 2H). The purity was 97.4% by HPLC. HRMS, Calcd. for $C_7H_4N_4O_5$: 224.0180; Found: 224.0195.

Example 29

Preparation of 5-Aza-7-carbamoyl-1,4-dihydroquinoxaline-2,3-dione (67)

6-Amino-5-nitronicotinamide (65)

To a solution of 6-aminonicotinamide (524 mg, 3.82 mmol) in TFA (10 mL) was added KNO₃ (524 mg, 5.18 mmol) at room temperature with stirring. The resulting solution was stirred at 80° C. for 18 h, cooled to room temperature, then cooled water (100 mL) was added (no precipitate was formed). The resulting acidic aqueous solution was basified to pH 9 with 40% aq NaOH. The precipitate was filtered, washed with cooled water (2×5 mL), and dried to give 160 mg (23%) of 65 as a yellow powder, mp 289°–90° C. ¹H NMR (DMSO-d₆), 7.430 (s, 1H), 8.078 (s, 1H), 8.285 (bs, 2H, easily exchanged with D20), 8.840 (s, 2H).

5,6-Diaminonicotinamide (66)

A mixture of 65 (168 mg, 0.92 mmol), Raney Ni (about 200 mg) and EtOH (25 mL) was shaken under $H_2$ (40 psi) for 1 h, then filtered. The filtrate was evaporated to give 121 mg (86%) of the diamine 66 as a gray powder, mp 227°–9° C.(dec.). ¹H NMR (DMSO-d₆), 4.747 (s, 2H), 5.890 (s, 2H), 6.867 (bs, 1H), 7.102 (s, 1H), 7.530 (bs, 1H), 7.861 (s, 1H).

5-Aza-7-carbamoyl-1,4-dihydroquinoxaline-2,3-dione (67)

A mixture of 66 (120 mg, 0.8 mmol) in diethyl oxalate was stirred at 180° C. under $N_2$ for 40 h, then cooled to room temperature. The mixture was diluted with hexane (20 mL), filtered, washed with EtOH (2×1 mL). The black solid obtained was stirred with diluted aq. HCl (pH 4) (15 mL) for 10 min. at room temperature, then filtered, washed with $H_2O$ and dried to give 56 mg (39%) of 67 as a brown powder, mp >370° C. ¹H NMR (DMSO-d₆), 7.513 (s, 1H), 7.840 (d, 1H, J=1.6), 8.111 (s, 1H), 8.552 (d, 1H, J=1.6), 12.097 (s, 1H), 12.521 (s, 1H).

Example 30

Preparation of 7-Carbamoyl-5-(N-oxy)aza-1,4-dihydroquinoxaline-2,3-dione (68)

7-Carbamoyl-5-(N-oxy)aza-1,4-dihydroquinoxaline-2,3-dione (67)

A suspension of 58 (54 mg, 0.26 mmol) in 1 mL of $F_3CCO_3H$ reagent (made from 20 mL of 30% hydrogen peroxide and 10 mL of trifluoroacetic anhydride) was refluxed for 15 min, cooled to room temperature and EtOH (10 mL) was added. The mixture was filtered, washed with EtOH (2×1 mL), and dried to give 40 mg (69%) of 68 as a yellow powder, mp >370° C. ¹H NMR (DMSO-d₆), 7.457(s, 1H), 7.694 (s, 1H), 8.130 (s, 1H), 8.615 (s, 1H), 12.276 (s, 2H).

Example 31

Preparation of 5-Aza-7-(imidazol-1-yl)-6-nitro-1,4-dihydroquinoxaline-2,3-dione (69)

5-Aza-7-(imidazol-1-yl)-6-nitro-1,4-dihydroquinoxaline-2,3-dione (69)

A mixture of 15 (243 mg, 1.0 mmol), imidazole (140 mg, 2.0 mmol), NaI (50 mg, 0.3 mmol) in DMF (5 mL) was stirred at 160° C. for 18 h, cooled to room temperature and cold water (20 mL) was added. The precipitate was filtered, washed with $H_2O$ (2×5 mL) and EtOH (3×5 mL), and dried to give 153 mg (56%) of 69 as a yellow powder, mp >370° C. ¹H NMR (DMSO-d₆), 7.095 (s, 1H), 7.550 (s, 1H). 7.626 (s, 1H), 8.046 (s, 1H), 12.42 (bs, 2H).

Example 32

Preparation of 5-Aza-7-[(3-N-oxy)imidazol-1-yl]-6-nitro-1,4-dihydroquinoxaline-2,3-dione (70)

5-Aza-7-[(3-N-oxy)imidazol-1-yl]-6-nitro-1,4-dihydroquinoxaline-2,3-dione (70)

A mixture of 69 (69 mg, 0.25 mmol) in 1.5 mL of $F_3CCO_3H$ (see Example 30 above) was stirred at 90° C. for 40 min. The resulting orange-yellow solution was cooled in an ice-water bath, EtOH (10 mL) was added dropwise with stirring, then rota-evaporated to dryness. The residual viscous oil was stirred with EtOAc (15 mL). The resulting mixture was filtered, washed with EtOAc (2×2 mL) and EtOH (2×2 mL), dried to give 53 mg (73%) of 70 as a yellow powder, mp >370° C. ¹H NMR (DMSO-d₆), 7.119 (bs 1H), 7.568 (bs, 1H). 7.635 (bs, 1H), 8.080 (bs, 1H), 12.181 (bs, 1H). 12.649 (bs, 1H).

Example 33

Preparation of 7-(Imidazol-1-yl)-5-(N-oxy)aza-1,4-dihydroquinoxaline-2,3-dione (71)

7-(Imidazol-1-yl)-5-(N-oxy)aza-1,4-dihydroquinoxaline-2,3-dione (71)

A mixture of 7-chloro-5-(N-oxy)aza-1,4-dihydroquinoxaline-2,3-dione 32 (214 mg, 1.0 mmol), imidazole (140 mg, 2.0 mmol) and NaI (50 mg, 0.3 mmol) in DMF (5 mL) was stirred at 160° C. for 18 h, cooled to room temperature and cold water (20 mL) was added. The precipitate was filtered, washed with H$_2$O (2×5 mL) and EtOH (3×5 mL), and dried to give 113 mg (46%) of 71 as a yellowish powder, mp >370° C. 1H NMR (DMSO-d$_6$), 6.925 (bs, 1H), 7.436 (d, 2H, J=2). 8.096 (d, 1H, J=2), 8.116 (s, 1H), 12.191 (bs, 2H).

Example 34

Preparation of 7-Bromo-6-methyl-8-nitro-5-(N-oxy)aza-1,4-dihydroquinoxaline-2,3-dione (72)

7-Bromo-6-methyl-8-nitro-5-(N-oxy)aza-1,4-dihydroquinoxaline-2,3-dione (72)

A mixture of 7-bromo-6-methyl-5-(N-oxy)aza-1,4-dihydroquinoxaline-2,3-dione 35 (1.77 g, 6.5 mmol) in fuming HNO$_3$ (10 mL) was stirred at 55° C. for 40 h. The resulting solution was cooled to room temperature and cold H$_2$O (40 mL) was added. The precipitate was filtered, washed with water (2×10 mL) and dried to give 0.863 g (61%) of 72 as a yellow powder, mp 309°–10° C(dec). $^1$H NMR (DMSO-d$_6$), 2.609(s, 3H), 12.536 (s, 1H). HRMS, Calcd. for C$_8$H$_5$BrN$_4$O$_5$: 315.9441; Found: 315.9440.

Example 35

Characterization of 6-Chloro-8-(N-oxy)aza-1,4-dihydroquinoxaline-2,3-dione and 6-Chloro-7-methyl-8-(N-oxy)aza-1,4-dihydroquinoxaline-2,3-dione for Anticonvulsant Activity in the Maximum Electroshock Model in Mice Introduction The objectives of the studies were to determine the time of maximal effect and potency for compounds 6-chloro-8-(N-oxy)aza-1,4-dihydroquinoxaline-2,3-dione and 6-chloro-7-methyl-8-(N-oxy)aza-1,4-dihydroquinoxaline-2,3-dione in the inhibition of maximal electroshock (MES)-induced tonic clonic seizures following intravenous (i.v.) administration in mice.

Study Design and Methods

The time-course study involved a one-factor, between groups design in which animals were divided into groups based on the time between administration of 6-chloro-8-(N-oxy)aza-1,4-dihydroquinoxaline-2,3-dione and 6-chloro-7-methyl-8-(N-oxy)aza-1,4-dihydroquinoxaline-2,3-dione and the MES stimulus. Similarly, the potency study involved a one-factor, between group design in which animals were divided into groups based on drug dose. Each group in both studies consisted of 8 animals.

6-Chloro-8-(N-oxy)aza-1,4-dihydroquinoxaline-2,3-dione and 6-chloro-7-methyl-8-(N-oxy)aza-1,4-dihydroquinoxaline-2,3-dione were dissolved in 0.05M Tris (J. T. Baker) at concentrations of 5 mg/mL and 2.5 mg/mL, respectively.

Experiments were conducted with Swiss-Webster male mice (Simonsen Lab. Inc.). Mice were 5–6 weeks old and weighed 18–24 g upon arrival in the laboratory. In the time course study, mice were treated with an i.v. injection of 6-chloro-8-(N-oxy)aza-1,4-dihydroquinoxaline-2,3-dione (5 mg/kg) or 6-chloro-7-methyl-8-(N-oxy)aza-1,4-dihydroquinoxaline-2,3-dione(10mg/kg) or vehicle. Mice were tested at 2, 15, 30, or 60 minutes after vehicle or drug administration. In the potency studies mice were treated with either vehicle, 0.5, 1, 1.5, 2, or 3 mg/kg 6-chloro-8-(N-oxy)aza-1,4-dihydroquinoxaline-2,3-dione or vehicle, 4, 6, 7, 8, or 10 mg/kg 6-chloro-7-methyl-8-(N-oxy)aza-1,4-dihydroquinoxaline-2,3-dione and tested at 2 minutes post injection point. The electroshock device was a Ugo Basile ECT Unit 7801 (Varese, Italy; Model 24093). The electroshock characteristics were as follows: 50 mA, 60 pulses per second, 0.8 second pulse width, and a 0.2 second train length. Mice received a shock through saline wetted corneal electrodes following administration of vehicle or 6-chloro-8-(N-oxy)aza-1,4-dihydroquinoxaline-2,3-dione or 6-chloro-7-methyl-8-(N-oxy)aza-1,4-dihydroquinoxaline-2,3-dione and were observed for the presence of a tonic clonic seizure. Tonic seizures were defined as the tonic extension of the forelimbs and hindlimbs. Absence of a complete tonic convulsion immediately following the administration of the electroshock indicated that 6-chloro-8-(N-oxy)aza-1,4-dihydroquinoxaline-2,3-dione or 6-chloro-7-methyl-8-(N-oxy)aza-1,4-dihydroquinoxaline-2,3-dione inhibited MES-induced seizures. Therefore, the result from each animal was an all-or-none phenomenon with either a seizure present or absent following the shock administration. The time point at which 6-chloro-8-(N-oxy)aza-1,4-dihydroquinoxaline-2,3-dione and 6-chloro-7-methyl-8-(N-oxy)aza-1,4-dihydroquinoxaline-2,3-dione produced a maximal response was determinated by analyzing the graphical results. The dose at which 50% of the animals were protected against MES-induced seizures (ED$_{50}$) was calculated by Litchfield and Wilcoxon Method (Pharm/PCS R. J. Tallarida & R. B. Murray Version 4.2).

Results

Figure 2:
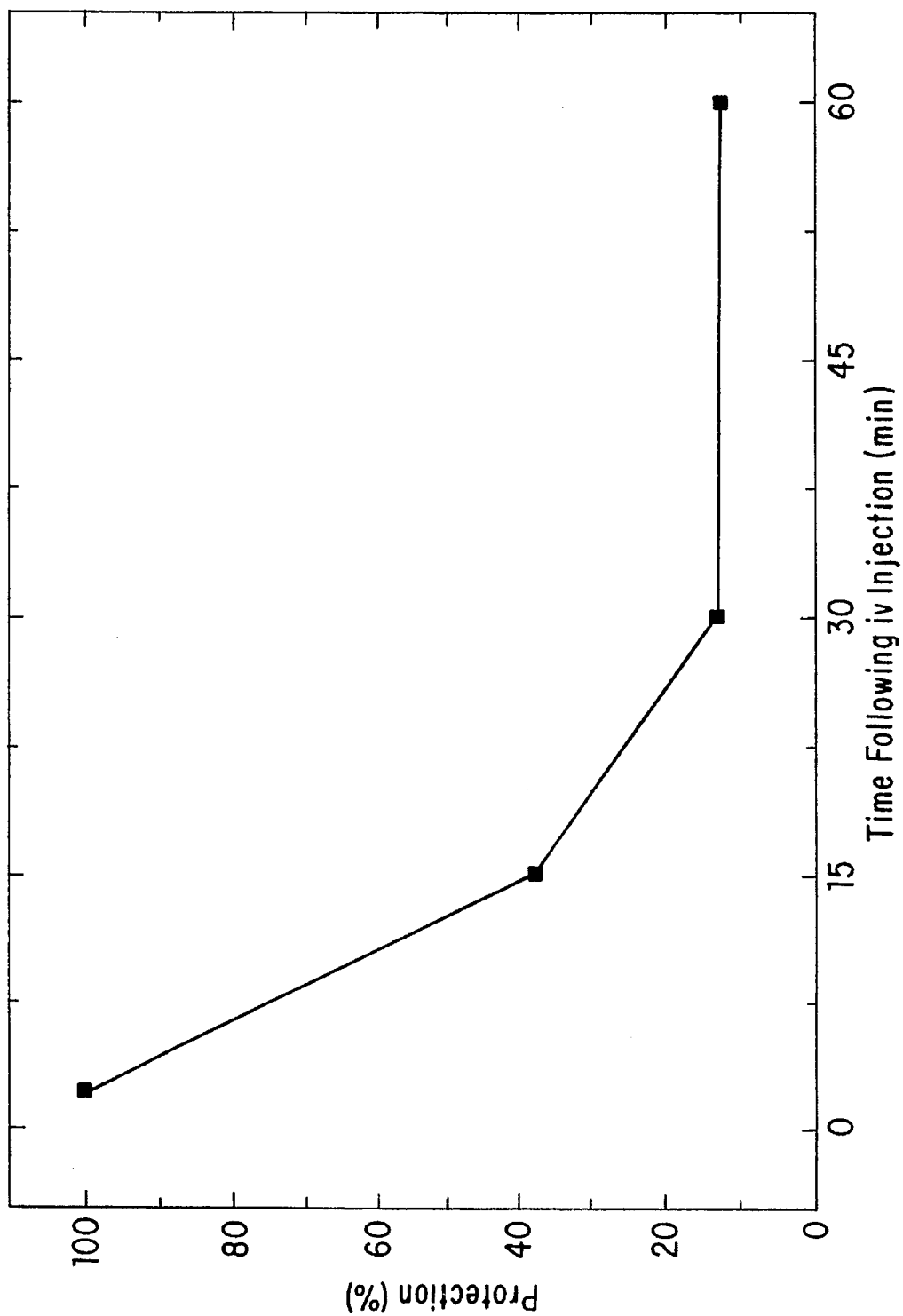
FIG. 2 depicts a graph showing the time course of 6-chloro-7-methyl-8-(N-oxy)aza-1,4-dihydroquinoxaline-2,3-dione (10 mg/kg, i.v.) in the inhibition of MES.

The efficacy of 6-chloro-8-(N-oxy)aza-1,4-dihydroquinoxaline-2,3-dione and 6-chloro-7-methyl-8-(N-oxy)aza-1,4-dihydroquinoxaline-2,3-dione in inhibiting MES-induced tonic seizures decreased over one hour as shown in FIGS. 1 and 2 respectively. Two minutes following administration of 6-chloro-8-(N-oxy)aza-1,4-dihydroquinoxaline-2,3-dione and 6-chloro-7-methyl-8-(N-oxy)aza-1,4-dihydroquinoxaline-2,3-dione, 8/8 mice showed no tonic seizures. When mice were subjected to electroshock 15 minutes after 6-chloro-8-(N-oxy)aza-1,4-dihydroquinoxaline-2,3-dione and 6-chloro-7-methyl-8-(N-oxy)aza-1,4-dihydroquinoxaline-2,3-dione, 4/8 and 3/8 mice were, respectively, protected against seizures. Thereafter, the maximal anti-MES effects of 6-chloro-8-(N-oxy)aza-1,4-dihydroquinoxaline-2,3-dione and 6-chloro-7-methyl-8-(N-oxy)aza-1,4-dihydroquinoxaline-2,3-dione were observed at 2 minutes post-injection.

Figure 3:
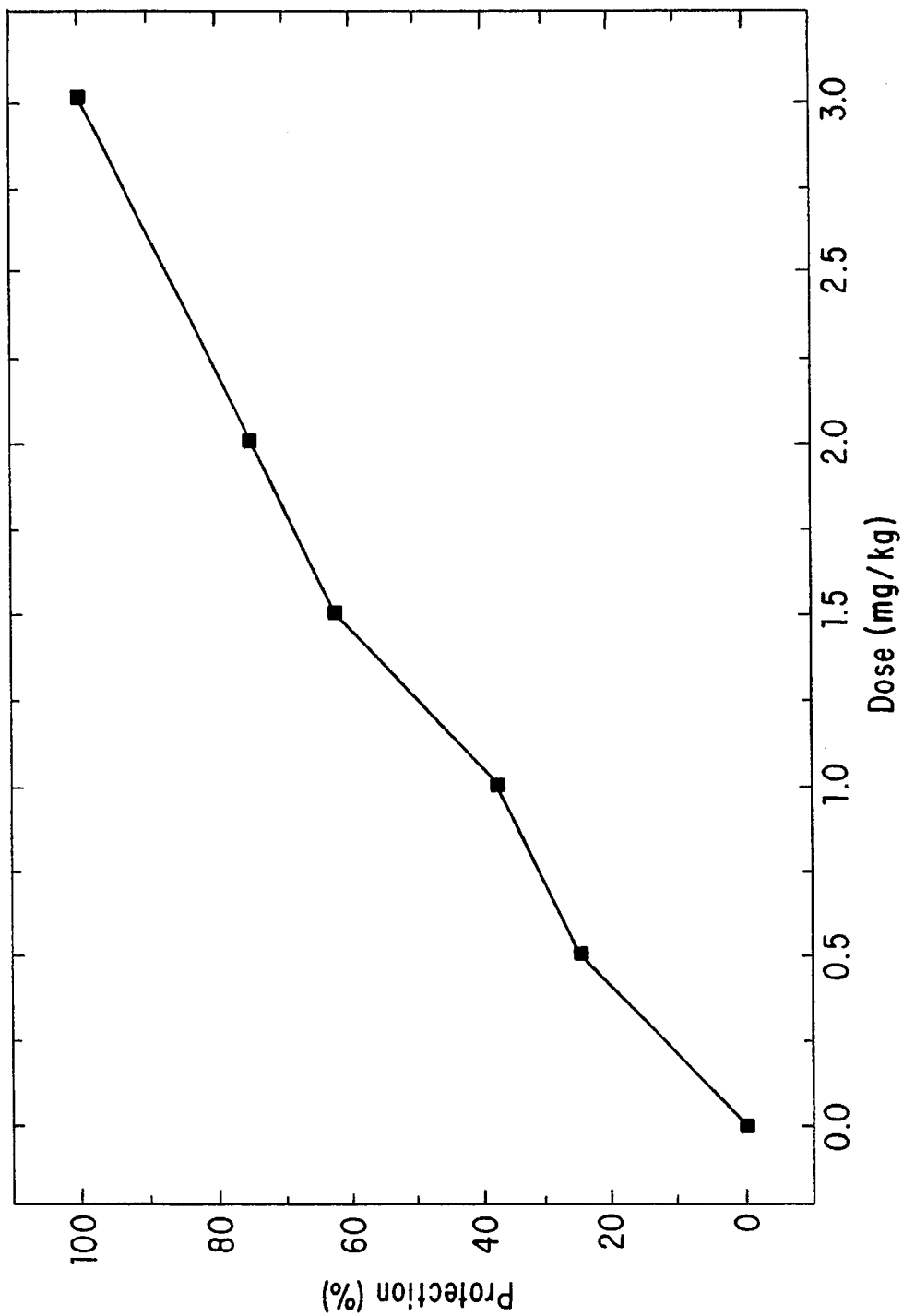
FIG. 3 depicts a graph showing the dose response of 6-chloro-8-(N-oxy)aza-1,4-dihydroquinoxaline-2,3-dione in the inhibition of MES.
Figure 4:
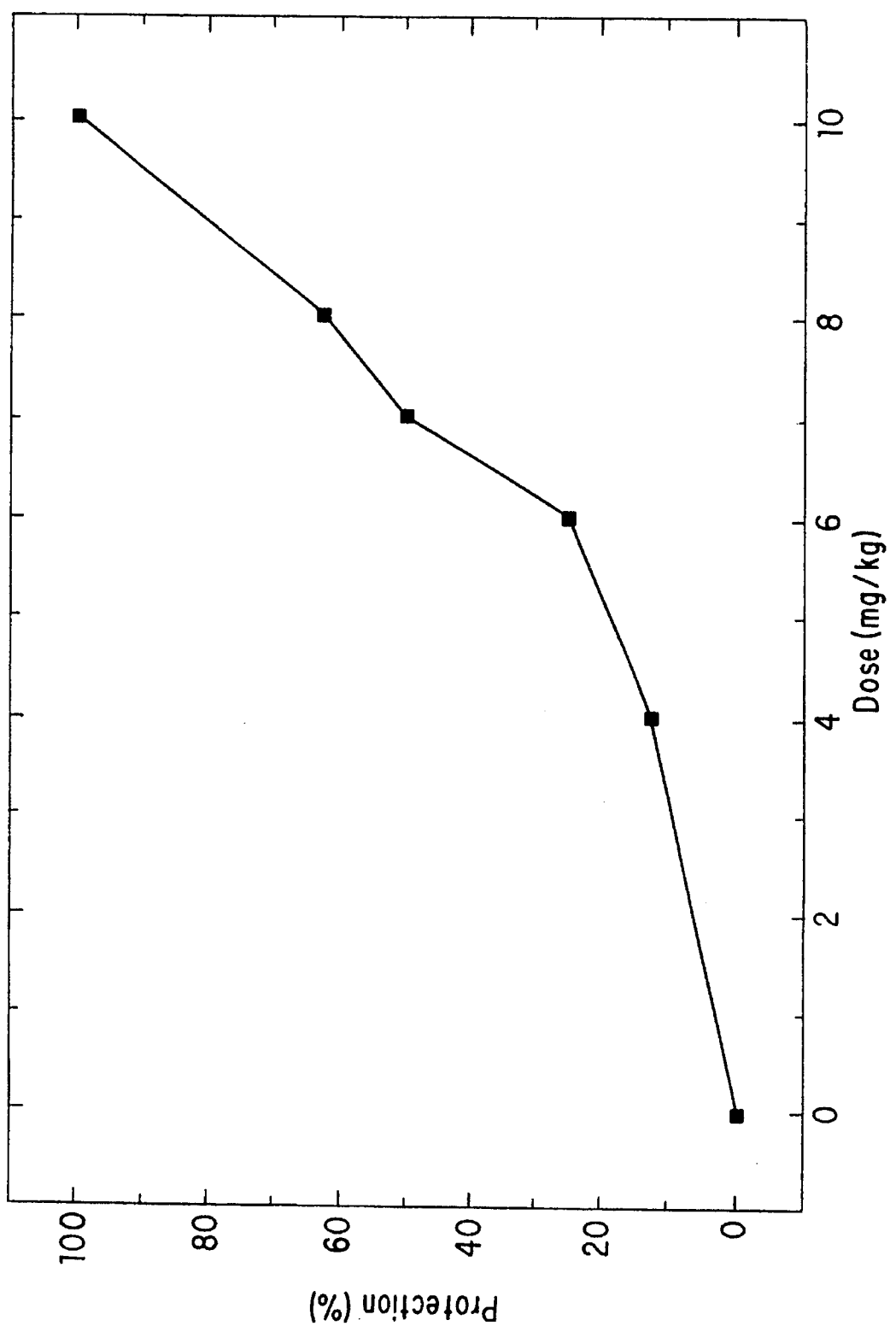
FIG. 4 depicts a graph showing the dose response of 6-chloro-7-methyl-8-(N-oxy)aza-1,4-dihydroquinoxaline-2,3-dione in the inhibition of MES.

A non-cumulative dose-response study was conducted with increasing doses of 6-chloro-8-(N-oxy)aza-1,4-dihydroquinoxaline-2,3-dione and 6-chloro-7-methyl-8-(N-oxy)aza-1,4-dihydroquinoxaline-2,3-dione in Tris 0.05M. Seizures were elicited at the time of maximal effect (2 minutes). The lowest dose of 6-chloro-8-(N-oxy)aza-1,4-dihydroquinoxaline-2,3-dione (0.5 mg/kg) produced protection for 25% of the mice (2/8 mice), the lowest does of 6-chloro-7-methyl-8-(N-oxy)aza-1,4-dihydroquinoxaline-2,3-dione (4 mg/kg) produced protection for 12.5% of the mice (1/8 mice) as shown in FIGS. 3 and 4 respectively. The calculated ED$_{50}$s were 1.26 mg/kg and 6.71 mg/kg, respectively, with 95% confidence limits ranging 0.94–1.67 mg/kg and 5.48–8.22 mg/kg, respectively.

Conclusion

The time of maximal effect for 6-chloro-8-(N-oxy)aza-1,4-dihydroquinoxaline-2,3-dione and 6-chloro-7-methyl-8-(N-oxy)aza-1,4-dihydroquinoxaline-2,3-dione to block MES-induced seizures was observed at 2 minutes when administered I.V. in male Swiss-Webster mice. In addition, 6-chloro-8-(N-oxy)aza-1,4-dihydroquinoxaline-2,3-dione and 6-chloro-7-methyl-8-(N-oxy)aza-1,4-dihydroquinoxaline-2,3-dione, dose dependently, inhibited MES-induced seizures. The $ED_{50}$s were 1.26 mg/kg and 6.71 mg/kg respectively.

Example 36

Evaluation of the Neuroprotective Effect of 6-Chloro-8-(N-oxy)aza-1,4-dihydroquinoxaline-2,3-dione in a Rat Model of Permanent Focal Cerebral Ischemia Using Continuous i.v. Drug Infusion Introduction The N-methyl-D-aspartate (NMDA) subtype of excitatory amino acid receptors appears to play a crucial role in neuronal degeneration induced by focal cerebral ischemia. A number of competitive and non-competitive NMDA receptor antagonists have been shown to provide significant protection against neuronal degeneration in different animal models of focal ischemia (Bullock, R. & Fujisawa, H., "The role of glutamate antagonists for the treatment of CNA injury," in J. Neurotrauma 9, Suppl. 2:S443–S462 (1992)). In the present study, we studied the neuroprotective effect of the NMDA receptor glycine site antagonist 6-chloro-8-(N-oxy)aza-1,4-dihydroquinoxaline-2,3-dione in the rat model of the focal ischemia.

Methods

1. Induction of focal ischemia

Male Sprague-Dawley rats (290–820 g) were intubated and maintained under anesthesia with ±2% of halothane. Body temperature was maintained at 37.5° C. during surgery by means of a warming pad and a rectal probe connected to the control unit. The common carotid arteries (CCA) were isolated and a loose silk ligature was placed around each CCA. A vertical skin incision was made between the left orbit and the auditory canal, posterior part of zygoma removed, and a small opening (2.0/2.5 mm) drilled dorsorostrally to the foramen ovale under constant saline irrigation. The dura was opened with a microsurgical hook and the brain gently retracted with a fine spatula to expose the bifurcation of the internal carotid artery and the middle cerebral artery. The ipsilateral CCA was ligated and the MCA coagulated from its origin to the olfactory tract. Two hours after MCA occlusion, the clip from the contralateral CCA was removed.

2. Drug administration

6-Chloro-8-(N-oxy)aza-1,4-dihydroquinoxaline-2,3-dione was dissolved in 0.05 Tris and 5% glucose and infused as a slow 10 or 20 mg/kg i.v. bolus (immediately after MCA occlusion) followed by 7 or 14 mg/kg/h infusion, respectively, for 22 hours.

3. Histology

Brains were sliced into 2 mm blocks and stained with tetrazolium red (2,3,5-triphenyl tetrazolium chloride). The areas of brain damage were assessed using an image analyzer (Image-1, Universal Imaging Corporation, Pa.) to determine the volume of cortical and subconical infarction by integration of areas and the distance between each level.

Results

6-Chloro-8-(N-oxy)aza-1,4-dihydroquinoxaline-2,3-dione given as 20 mg bolus followed by 14 mg/kg/h infusion for 22 hours produced a significant reduction (67%, $F_{1,20}=5.15$, $p<0.05$, ANOVA, FIG. 5) in cortical infarct volume, whereas the lower dose provided no protection.

Conclusion

6-Chloro-8-(N-oxy)aza-1,4-dihydroquinoxaline-2,3-dione provided significant neuroprotection in a rat model of focal ischemia.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A method of treating or preventing neuronal loss associated with stroke or ischemia, comprising administering to an animal in need of such treatment or prevention an effective amount of a compound of the formula:

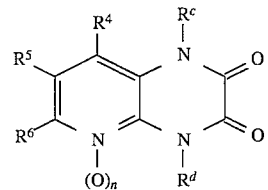

or a pharmaceutically acceptable salt thereof;
wherein n is 1;

$R^4$ is hydrogen or fluoro;

$R^5$ and $R^6$ are independently hydrogen, nitro, amino, halo, haloalkyl, cyano, alkyl, cycloalkyl, alkenyl, alkynyl, azido, acylamino, alkylsulfonyl, aryl, substituted aryl, heteroaryl, alkoxy, trialkylsilyl-substituted alkoxy, aryloxy, substituted aryloxy, heteroaryloxy, a heterocyclic group, a heterocyclicoxy group, aralkoxy, or haloalkoxy;

$R^c$ is hydrogen; and $R^d$ is hydrogen, hydroxy, amino, —$CH_2CONHAr$, —$NHCONHAr$, —$NHCOCH_2Ar$, or —$COCH_2Ar$, wherein Ar is an aryl group, or a radical having the Formula:

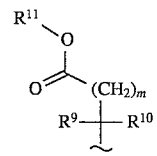

wherein $R^9$ is hydrogen, lower alkyl of 1–6 carbon atoms, or aryl; $R^{10}$ is hydrogen or lower alkyl of 1–6 carbon atoms; m is an integer from zero to 5; and $R^{11}$ is hydrogen, $C_{1-6}$ alkyl, or aralkyl.

2. The method of claim 1, wherein $R^5$ and $R^6$ are not hydrogen, and $R^c$, $R^d$ and $R^4$ are hydrogen.

3. The method of claim 1, wherein at least one of $R^5$ and $R^6$ is halo or haloalkyl.

4. The method of claim 1, wherein $R^5$ and $R^6$ are independently nitro, halo, haloalkyl, alkyl, or azido; and $R^c$ and $R^d$ are hydrogen.

5. The method of claim 1, wherein $R^5$ is not hydrogen; $R^4$ and $R^6$ are hydrogen; and $R^c$ and $R^d$ are hydrogen.

6. The method of claim 1, wherein said compound is one of:

6,7-dichloro-8-(N-oxy)aza-1,4-dihydroquinoxaline-2,3-dione;
6-chloro-8-(N-oxy)aza-1,4-dihydroquinoxaline-2,3-dione;
6-bromo-8-(N-oxy)aza-1,4-dihydroquinoxaline-2,3-dione;
6-bromo-7-methyl-8-(N-oxy)aza-1,4-dihydroquinoxaline-2,3-dione;
6-chloro-7-methyl-8-(N-oxy)aza-1,4-dihydroquinoxaline-2,3-dione;
6-chloro-7-bromo-8-(N-oxy)aza-1,4-dihydroquinoxaline-2,3-dione;

6-methyl-8-(N-oxy)aza-1,4-dihydroquinoxaline-2,3-dione;

6-trifluoromethyl-8-(N-oxy)aza-1,4-dihydroquinoxaline-2,3-dione;

6-nitro-8-(N-oxy)aza-1,4-dihydroquinoxaline-2,3-dione; or 6-carbamoyl-8-(N-oxy)aza-1,4-dihydroquinoxaline-2,3-dione.

7. The method of claim 1, wherein said compound crosses the blood-brain-barrier.

8. A method of treating or preventing neuronal loss associated with stroke or ischemia, comprising administering to an animal in need of such treatment or prevention an effective amount of a compound selected from the group consisting of 6-bromo-7-methyl-5-nitro-8-aza-1,4-dihydroquinoxaline-2,3-dione;

6,7-dichloro-8-aza-1,4-dihydroquinoxaline-2,3-dione; and 6-bromo-7-methyl-8-aza-1,4-dihydroquinoxaline-2,3-dione.

9. The method of any one of claims 1–8, wherein said neuronal loss occurs as a result of multiple strokes resulting in dementia.

10. The method of any one of claims 1–8, wherein said compound is administered as part of a pharmaceutical composition comprising a pharmaceutically acceptable carrier.

* * * * *